(12) United States Patent
Hadden et al.

(10) Patent No.: US 9,650,365 B2
(45) Date of Patent: May 16, 2017

(54) ITRACONAZOLE ANALOGUES AND METHODS OF USE THEREOF

(71) Applicant: UNIVERSITY OF CONNECTICUT, Farmington, CT (US)

(72) Inventors: Matthew Kyle Hadden, Ellington, CT (US); Upasana Banerjee, Houston, TX (US)

(73) Assignee: UNIVERSITY OF CONNECTICUT, Farmington, CT (US)

( * ) Notice: Subject to any disclaimer, the term of this patent is extended or adjusted under 35 U.S.C. 154(b) by 0 days.

(21) Appl. No.: 15/225,021

(22) Filed: Aug. 1, 2016

(65) Prior Publication Data

US 2016/0340346 A1    Nov. 24, 2016

Related U.S. Application Data

(63) Continuation-in-part of application No. PCT/US2015/013808, filed on Jan. 30, 2015.

(60) Provisional application No. 61/934,714, filed on Feb. 1, 2014.

(51) Int. Cl.
    *C07D 405/14*     (2006.01)
    *C07D 405/12*     (2006.01)

(52) U.S. Cl.
    CPC ......... *C07D 405/14* (2013.01); *C07D 405/12* (2013.01)

(58) Field of Classification Search
    CPC .......................... C07D 405/14; C07D 405/12
    USPC .................................................... 514/252.02
    See application file for complete search history.

(56) References Cited

U.S. PATENT DOCUMENTS

| 4,456,605 A | 6/1984 | Heeres et al. |
| 4,791,111 A * | 12/1988 | Heeres ................ C07D 231/12 514/254.07 |
| 2009/0203713 A1 | 8/2009 | Beachy et al. |
| 2012/0283194 A1 | 11/2012 | Atwood et al. |

FOREIGN PATENT DOCUMENTS

| EP | 1886695 A1 | 2/2008 |
| WO | 2013036866 A1 | 3/2013 |
| WO | 2015116947 | 8/2015 |

OTHER PUBLICATIONS

International Search Report and Written Opinion; International Application No. PCT/US15/13808; International Filing Date Jan. 30, 2015; Date of Mailing Apr. 9, 2015; 9 pages.
Chong et al.; "Inhibition of Angiogenesis by the Antifungal Drug Itraconazole"; ACS Chemical Biology; 2(4); pp. 263-270; (2007).
Chen et al.; "Posaconazole, a Second-Generation Triazole Antifungal Drug, Inhibits the Hedgehog Signaling Pathway and Progression of Basal Cell Carcinoma"; Molecular Cancer Therapeutics; 15(5); pp. 866-876; (2006).
Pace et al.; "Repurposing the Clinically Efficacious Antifungal Agent Itraconazole as an Anticancer Chemotherapeutic"; Journal of Medicinal Chemistry; 59; pp. 3635-3649; (2016).

* cited by examiner

*Primary Examiner* — Yevegeny Valenrod
(74) *Attorney, Agent, or Firm* — Cantor Colburn LLP

(57) ABSTRACT

Disclosed herein are analogs of itraconazole that are both angiogenesis and hedgehog signaling pathway inhibitors. The compounds are expected to be useful in the treatment of cancer, particularly cancers that are dependent upon the hedgehog signaling pathway such as basal cell carcinoma and medulloblastoma.

13 Claims, 6 Drawing Sheets

(A)

(B)

ITRACONAZOLE ANALOGUES AND METHODS OF USE THEREOF

CROSS-REFERENCE TO RELATED APPLICATIONS

This application is a Continuation in Part of PCT/US2015/013808 filed on Jan. 30, 2015, which claims priority to U.S. Provisional Application 61/934,714 filed on Feb. 1, 2104, which are incorporated herein by reference in their entirety.

STATEMENT REGARDING FEDERALLY SPONSORED RESEARCH & DEVELOPMENT

This invention was made with government support under 1R01CA190617-01 awarded by the National Institutes of Health. The government has certain rights in the invention.

FIELD OF THE DISCLOSURE

The present disclosure is related to novel compounds having utility as anti-cancer agents, specifically novel derivatives of azole antifungals.

BACKGROUND

Identifying novel biological activities of FDA-approved drugs has emerged as a viable strategy to expedite the drug discovery process. The pharmacokinetic and toxicological profiles of these compounds are well-understood and they are inherently "drug-like." To this end, drug development researchers have made a concerted effort to incorporate small molecule libraries containing approved drugs in their high-throughput screens. Recently, two such screens designed to repurpose FDA-approved compounds as anti-cancer chemotherapeutics identified the clinically efficacious antifungal itraconazole (ITZ) as both an inhibitor of the hedgehog (Hh) signaling pathway ($IC_{50}$=690 nM) and angiogenesis ($IC_{50}$=160 nM The Hh pathway is a developmental signaling pathway that plays a key role in directing growth and tissue patterning during embryonic development. Dysregulation of Hh signaling has been linked to the development of a variety of human tumors; most notably, basal cell carcinoma (BCC) and medulloblastoma (MB). Recent years have seen the development of numerous small molecule Hh pathway inhibitors, the majority of which directly bind Smoothened (SMO), a 7-transmembrane GPCR-like receptor and key regulator of pathway signaling. The most advanced of these compounds, the small molecule GDC-0449 (Vismodegib/Erivedge™), was approved by the FDA for the treatment of metastatic BCC, highlighting the clinical relevance of Hh pathway inhibition. The importance of angiogenesis in tumor formation, growth, and metastasis is well-documented and numerous small molecules and biologics that inhibit angiogenesis are clinically useful anti-cancer agents.

While itraconazole has anti-cancer activity, it can have serious detrimental interactions with other commonly taken medications such as anticoagulants, statins and calcium channel blockers. It is thus desirable to provide alternatives to itraconazole that maintain the anti-cancer properties, but that potentially do not have the side-effects observed for itraconazole.

BRIEF SUMMARY

In one aspect, included herein is a compound having the structure of Formula (I)

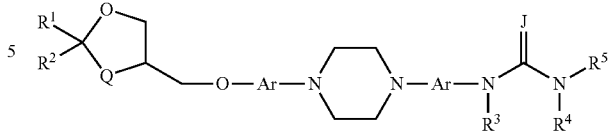

wherein

Q is O or $CH_2$;

each Ar is independently unsubstituted or substituted aryl;

J is O or S;

$R^1$ is $C_{1-6}$alkyl optionally substituted with an amino, a $C_{1-6}$ alkylamino, a $C_{1-6}$ dialkylamino, an N-acylamino, —COOH, an aryl, a heterocycloalkyl, pyrrolidine, pyrrole, or pyridinyl group;

$R^2$ is $C_{1-6}$ alkyl or unsubstituted or substituted aryl;

$R^3$ is H or unsubstituted or substituted $C_{1-6}$ alkyl;

$R^4$ is H or unsubstituted or substituted $C_{1-6}$ alkyl; or $R^3$ and $R^4$ join to form an unsubstituted or substituted 5- or 6-membered ring with the —N-(=J)-N— moiety where $R^3$ and $R^4$ form a unsubstituted or substituted $C_{2-3}$ carbohydryl group or a unsubstituted or substituted $C_{1-2}$ carbohydryl group linked via a nitrogen to a nitrogen of the —N-(=J)-N— moiety;

$R^5$ is H, substituted or unsubstituted $C_{1-6}$ alkyl, $C_{1-6}$ alkoxy, $C_{2-6}$ alkanoyl, $C_{1-6}$ alkoxcarbonyl, $C_{1-6}$ haloalkyl, wherein the substituted $C_{1-6}$alkyl is substituted with 1, 2, or 3 substituents, each substituent is independently $C_{1-6}$ alkyl, —OH, —COOH, cyano, nitro, $C_{1-6}$ monoalkylamine, $C_{1-6}$ dialkylamine, $C_{1-6}$ haloalkyl, $C_1$-6 haloalkoxy;

a pharmaceutically acceptable salt, a stereoisomeric form thereof, or a combination thereof.

In another aspect, included are pharmaceutical compositions including the disclosed compounds and a pharmaceutically acceptable excipient.

In yet another aspect, included herein are methods of treating cancer, particularly Hh-signaling pathway-dependent cancers, with the compounds disclosed herein, including posaconazole.

The above-described and other features will be appreciated and understood by those skilled in the art from the following detailed description, drawings, and appended claims.

DETAILED DESCRIPTION

Disclosed herein are itraconazole (ITZ) and posaconazole (PSZ) analogues with novel structures that were designed based on systematic exploration of the ITZ and PSZ scaffolds to identify structural modifications that enhance inhibition of Hh signaling and maintain this activity against SMO mutants that confer resistance against vismodegib or other Hh inhibitors. The ITZ and PSZ analogues are angiogenesis inhibitors and are thus particularly useful as anti-cancer agents, for example, to treat cancers that are dependent upon the Hh signaling pathway. In another aspect, the ITZ and PSZ analogs are useful to treat cancers that are resistant to Vismodegib. In another embodiment, PSZ is disclosed as useful to treat cancer, including for example, Hh signaling pathway-dependent cancers.

Figure 1:
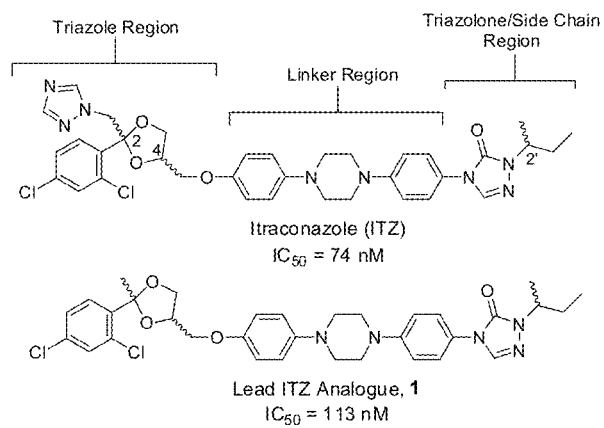
FIG. 1 shows the structure and regions of itraconazole and Analogue 1.

The anti-fungal activity of ITZ is a result of its inhibition of lanosterol 14α-demethylase (14LDM/CYP51), a cytochrome P450 enzyme that plays a crucial role in the biosynthesis of ergosterol, which is a major component of fungal cell membranes. The N4 of the ITZ triazole moiety interacts with the heme group in 14LDM, preventing coordination of the molecular oxygen required to initiate oxidation. This ability to coordinate the heme of CYP450s is also responsible for its most common detrimental side effect, inhibition of CYP3A4. CYP3A4 inhibition results in multiple drug-drug interactions and contraindications and requires careful monitoring of diet and drug regimens when ITZ is administered. In addition to the triazole containing "left-hand" portion of the scaffold, ITZ also contains a central phenyl-piperizine-phenyl linker region and a "right-side" triazolone/side chain region (FIG. 1). Within the context of its anti-fungal activity, the extended linker and triazolone/side chain regions are not essential for binding the active site of CYP51; however, they do interact with several amino acid residues in the substrate access channel. ITZ contains three chiral centers (2, 4, and 2'), and can potentially exist as a mixture of eight distinct stereoisomers; however, formation of the cis-configurations around the dioxolane ring predominates during its synthesis and pharmaceutical preparations of ITZ are typically administered as a 1:1:1:1 mixture of the cis racemates.

In one aspect, described herein are ITZ analogues in which the triazole moiety has been removed such as Analogue 1. FIG. 1 compares the structures of ITZ and Analogue 1. Analogue 1, for example, retains its Hh inhibitory activity and does not affect CYP3A4. In addition, also included herein are ITZ analogues in which the triazole ring has been replaced with various isosteres. Thus, a novel change to the ITZ scaffold has been identified that improves activity and reduces detrimental side effects. Additional analogues of ITZ and PSZ are also described herein.

Specifically, described herein are ITZ and PSZ analogues, wherein the ITZ and PSZ analogues are lacking the triazole moiety, or wherein the triazole moiety has been modified. In certain aspects, the ITZ and PSZ analogues are effective inhibitors of the Hh pathway, do not inhibit CYP3A4, and/or have anti-angiogenic activity. Overall, the strategy for the design of the ITZ and PSZ analogues was to make conservative and systematic modifications to separate regions of the ITZ and PSZ scaffolds. Because removal of the triazole functionality abrogates the off-target CYP3A4 inhibition and does not affect Hh inhibition, the analogues will not incorporate the triazole functionality.

The ITZ and PSZ analogues are compounds having the structure of Formula (I)

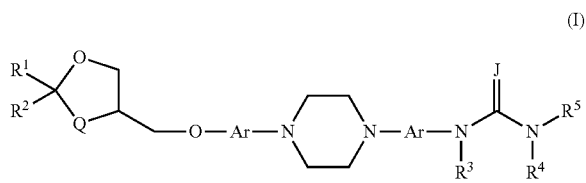

wherein
Q is O or $CH_2$, specifically O;
each Ar is independently unsubstituted or substituted aryl, specifically phenyl, pyridine, pyrazine, or pyridazine, and more specifically phenyl;
J is O or S, specifically O;
$R^1$ is $C_{1-6}$ alkyl optionally substituted with an amino, a $C_{1-6}$ alkylamino, a $C_{1-6}$ dialkylamino, an N-acylamino, —COOH, an aryl, a heterocycloalkyl, pyrrolidine, pyrrole, or pyridinyl group, specifically $R^1$ is methyl, optionally substituted with 1-pyrrole, 3-pyridine, 4-pyridine, phenyl, m-aminophenyl, p-aminophenyl, acetylamine, 1-pyrrolidine, amino, or dimethylamino, and more specifically $R^1$ is methyl;
$R^2$ is $C_{1-6}$ alkyl or unsubstituted or substituted aryl, specifically unsubstituted or substituted phenyl, and more specifically $R^2$ is 2,4-dichlorophenyl or 2,4-difluorophenyl;
$R^3$ is H or unsubstituted or substituted $C_{1-6}$ alkyl;
$R^4$ is H or unsubstituted or substituted $C_{1-6}$ alkyl; or $R^3$ and $R^4$ join to form an unsubstituted or substituted 5- or 6-membered ring with the —N-(=J)-N— moiety where $R^3$ and $R^4$ form a unsubstituted or substituted $C_{2-3}$ carbohydryl group or a unsubstituted or substituted $C_{1-2}$ carbohydryl group linked via a nitrogen to a nitrogen of the —N-(=J)-N— moiety;
$R^5$ is H, substituted or unsubstituted $C_{1-6}$ alkyl, $C_{1-6}$ alkoxy, $C_{2-6}$ alkanoyl, $C_{1-6}$ alkoxcarbonyl, $C_{1-6}$ haloalkyl, wherein the substituted $C_{1-6}$ alkyl is substituted with 1, 2, or 3 substituents, each substituent is independently $C_{1-6}$ alkyl, —OH, —COOH, cyano, nitro, $C_{1-6}$ monoalkylamine, $C_{1-6}$ dialkylamine, $C_{1-6}$ haloalkyl, $C_{1-6}$ haloalkoxy;
a pharmaceutically acceptable salt, a stereoisomeric form thereof, or a combination thereof.

Specifically, in certain embodiments, the compounds of Formula (I) exclude itraconazole (CAS registry no. 84625-61-6) and posaconazole (CAS registry no. 171228-49-2).

In an embodiment, $R^3$ and $R^4$ join to form an unsubstituted or substituted 5- or 6-membered ring with the —N-(=J)-N— moiety where $R^3$ and $R^4$ form a unsubstituted or substituted $C_{2-3}$ carbohydryl group such as —CH=CH—, —CH$_2$—CH$_2$—, —CH$_2$—CH$_2$—CH$_2$—, or a unsubstituted or substituted $C_{1-2}$ carbohydryl group linked via a nitrogen to a nitrogen of the —N-(=J)-N— moiety, e.g. —CH=N—.

In an embodiment, $R^5$ is propyl; 2'-sec-butyl, the R isomer, the S isomer, a racemate or any enantiomerically enriched form; 2-hydroxypentan-3-yl, the 2R,3R-isomer, the 2S,3S, isomer, the 2R,3S, isomer, the 2S,3R isomer, or any diastereomerically enriched form; 2-hydroxyprop-2-yl; or 2-hydroxyprop-1-yl, the R isomer, the S isomer, a racemate, or any enantiomerically enriched form.

Within Formula (I), the compounds can be prepared in racemic form, or any optically enriched form. Exemplary stereoisomers of Formula (I) include Formulae (I-1), (I-2), (I-3), or (I-4):

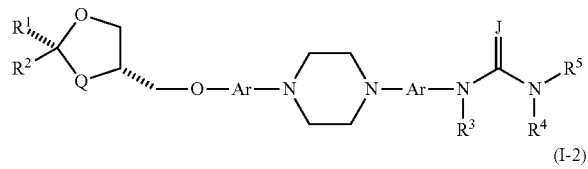
(I-1)

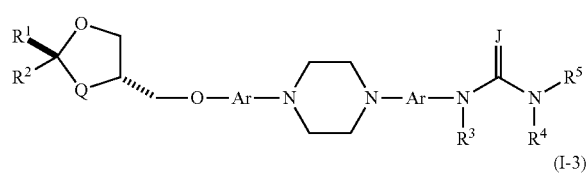
(I-2)

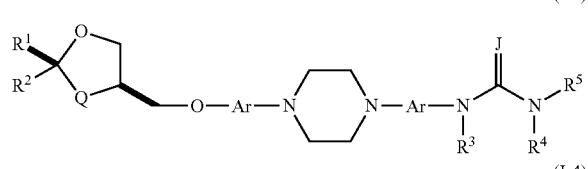
(I-3)

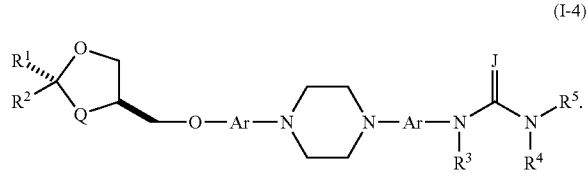
(I-4)

In another embodiment, the compounds have the structure of Formula (Ia)

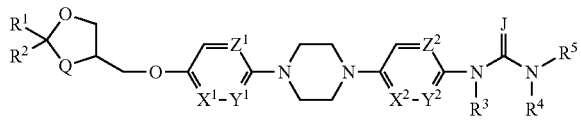
(Ia)

wherein
Q, J, $R^1$, $R^2$, $R^3$, $R^4$, and $R^5$ are as previously defined, and
wherein
each one of $X^1$, $X^2$, $Y^1$, $Y^2$, $Z^1$, and $Z^2$ independently is CH, CCH$_3$, or N.

Specifically, in certain embodiments, Formula (Ia) excludes itraconazole (CAS registry no. 84625-61-6) and posaconazole (CAS registry no. 171228-49-2). In several embodiments, a compound according to Formula (Ia) is included, wherein
$X^1$ is N and $Y^1$, $Z^1$, $X^2$, $Y^2$, and $Z^2$ are CH;
$Y^1$ is N and $X^1$, $Z^1$, $X^2$, $Y^2$, and $Z^2$ are CH;
$X^1$ and $Y^1$ are N and $Z^1$, $X^2$, $Y^2$, and $Z^2$ are CH;
$X^1$ and $Z^1$ are N and $Y^1$, $X^2$, $Y^2$, and $Z^2$ are CH;
$X^2$ is N and $X^1$, $Y^1$, $Z^1$, $Y^2$, and $Z^2$ are CH;
$Y^2$ is N and $X^1$, $Y^1$, $Z^1$, $X^2$, and $Z^2$ are CH;
$X^2$ and $Y^2$ are N and $X^1$, $Y^1$, $Z^1$, and $Z^2$ are CH; or
$X^2$ and $Z^2$ are N and $X^1$, $Y^1$, $Z^1$, and $Y^2$ are CH.

It will be understood that the corresponding chiral Formulae (Ia-1), (Ia-2), (Ia-3), and (Ia-4) are included.

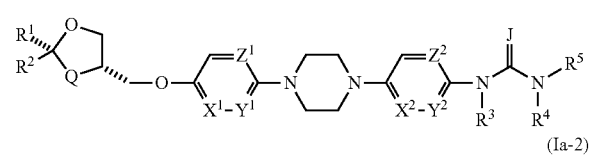
(Ia-1)

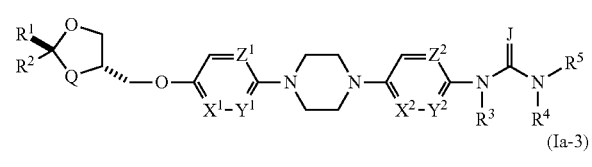
(Ia-2)

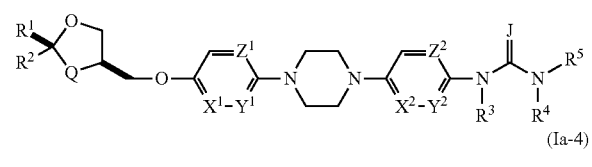
(Ia-3)

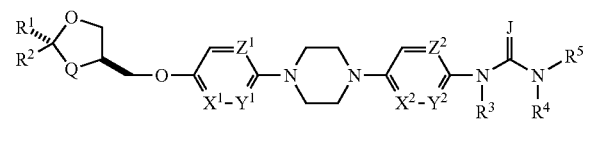
(Ia-4)

In another embodiment, the compounds have the structure of Formula (Ib)

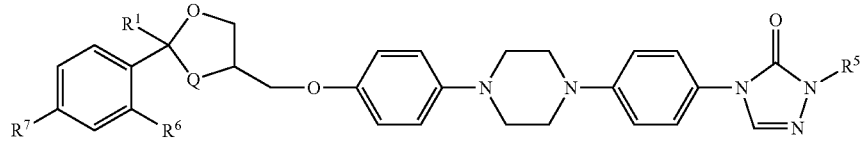
(Ib)

wherein

Q and $R^5$ are as previously defined, and wherein $R^6$ and $R^7$ are each independently H, halo, $C_{1-6}$ alkyl, $C_{1-6}$ alkoxy, $C_{2-6}$ alkanoyl, $C_{1-6}$ alkoxcarbonyl, —$NH_2$, —OH, —COOH, cyano, nitro, $C_{1-6}$ monoalkylamine, $C_{1-6}$ dialkylamine, $C_{1-6}$ haloalkyl, or $C_{1-6}$ haloalkoxy, specifically halo, and more specifically $R^6$ and $R^7$ are each independently Cl or F.

Specifically, in certain embodiments, Formula (Ib) excludes itraconazole (CAS registry no. 84625-61-6) and posaconazole (CAS registry no. 171228-49-2).

It will be understood that the corresponding chiral Formulae (Ib-1), (Ib-2), (Ib-3), and (Ib-4) are included.

the atom are replaced. When aromatic moieties are substituted by an oxo group, the aromatic ring is replaced by the corresponding partially unsaturated ring. For example a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent.

A dash ("-") that is not between two letters or symbols is used to indicate a point of attachment for a substituent. For example, —COOH is attached through the carbon atom.

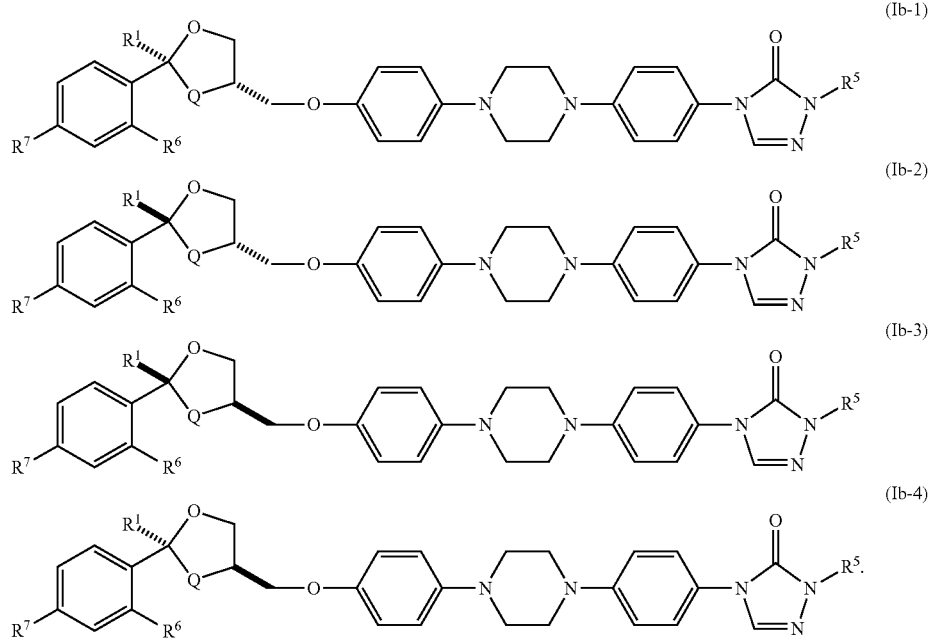

In certain situations, the compounds of Formulae I, Ia and Ib may contain one or more asymmetric elements such as stereogenic centers, stereogenic axes and the like, e.g., asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with double bonds may occur in Z- and E-forms, with all isomeric forms of the compounds being included in the present disclosure. In these situations, the single enantiomers, i.e., optically active forms, can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column.

The term "substituted", as used herein, means that any one or more hydrogens on the designated atom or group is replaced with a selection from the indicated group, provided that the designated atom's normal valence is not exceeded. When a substituent is oxo (i.e., =O), then 2 hydrogens on As used herein, "alkyl" is intended to include both branched and straight-chain saturated aliphatic hydrocarbon groups, having the specified number of carbon atoms. Thus, the term $C_1$-$C_6$ alkyl as used herein includes alkyl groups having from 1 to about 6 carbon atoms. When $C_0$-$C_n$ alkyl is used herein in conjunction with another group, for example, phenyl$C_0$-$C_4$ alkyl, the indicated group, in this case phenyl, is either directly bound by a single covalent bond ($C_0$), or attached by an alkyl chain having the specified number of carbon atoms, in this case from 1 to about 2 carbon atoms. Examples of alkyl include, but are not limited to, methyl, ethyl, n-propyl, isopropyl, n-butyl, t-butyl, n-pentyl, and sec-pentyl.

"Alkenyl" as used herein, indicates hydrocarbon chains of either a straight or branched configuration comprising one or more unsaturated carbon-carbon bonds, which may occur in any stable point along the chain, such as ethenyl and propenyl.

"Alkynyl" as used herein, indicates hydrocarbon chains of either a straight or branched configuration comprising one or more triple carbon-carbon bonds that may occur in any stable point along the chain, such as ethynyl and propynyl.

"Alkoxy" represents an alkyl group as defined above with the indicated number of carbon atoms attached through an oxygen bridge. Examples of alkoxy include, but are not limited to, methoxy, ethoxy, n-propoxy, propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy.

"Alkanoyl" indicates an alkyl group as defined above, attached through a keto (—(C═O)—) bridge. Alkanoyl groups have the indicated number of carbon atoms, with the carbon of the keto group being included in the numbered carbon atoms. For example a $C_2$alkanoyl group is an acetyl group having the formula $CH_3(C═O)$—.

The term "alkoxycarbonyl" indicates an alkoxy group, as defined above, having the indicated number of carbon atoms, attached through a keto linkage. The carbon of the keto linker is not included in the numbering, thus a $C_2$alkoxycarbonyl has the formula $CH_3CH_2O(C═O)$—.

The term "alkylcarboxamide" indicates an alkyl group, as defined above, having the indicated number of carbon atoms, attached through a carboxamide linkage, i.e., a —$CONH_2$ linkage, where one or both of the amino hydrogens is replaced by an alkyl group. Alkylcarboxamide groups may be mono- or di-alkylcarboxamide groups, such an ethylcarboxamide or dimethylcarboxamide.

As used herein, the term "mono- or di-alkylamino" indicates secondary or tertiary alkyl amino groups, wherein the alkyl groups are as defined above and have the indicated number of carbon atoms. The point of attachment of the alkylamino group is on the nitrogen. Examples of mono- and di-alkylamino groups include ethylamino, dimethylamino, and methyl-propyl-amino.

As used herein, the term "aryl" indicates aromatic groups containing only carbon in the aromatic ring or rings. Such aromatic groups may be further substituted with carbon or non-carbon atoms or groups. Typical aryl groups contain 1 to 3 separate, fused, or pendant rings and from 6 to about 18 ring atoms, without heteroatoms as ring members. Where indicated aryl groups may be substituted. Such substitution may include fusion to a 5 to 7-membered saturated cyclic group that optionally contains 1 or 2 heteroatoms independently chosen from N, O, and S, to form, for example, a 3,4-methylenedioxy-phenyl group. Aryl groups include, for example, phenyl, naphthyl, including 1-naphthyl and 2-naphthyl, and bi-phenyl.

In the term "(aryl)alkyl", aryl and alkyl are as defined above, and the point of attachment is on the alkyl group. This term encompasses, but is not limited to, benzyl, phenylethyl, and piperonyl. Likewise, in the term (aryl)carbhydryl, aryl and carbhydryl are as defined above and the point of attachment is on the carbhydryl group, for example a phenylpropen-1-yl group.

"Carbhydryl" as used herein, includes both branched and straight-chain hydrocarbon groups, which are saturated or unsaturated, having the specified number of carbon atoms.

"Cycloalkyl" as used herein, indicates saturated hydrocarbon ring groups, having the specified number of carbon atoms, usually from 3 to about 8 ring carbon atoms, or from 3 to about 7 carbon atoms. Examples of cycloalkyl groups include cyclopropyl, cyclobutyl, cyclopentyl, or cyclohexyl as well as bridged or caged saturated ring groups such as norbornane or adamantane.

"Haloalkyl" indicates both branched and straight-chain saturated aliphatic hydrocarbon groups having the specified number of carbon atoms, substituted with 1 or more halogen atoms, generally up to the maximum allowable number of halogen atoms. Examples of haloalkyl include, but are not limited to, trifluoromethyl, difluoromethyl, 2-fluoroethyl, and penta-fluoroethyl.

"Haloalkoxy" indicates a haloalkyl group as defined above attached through an oxygen bridge.

"Halo" or "halogen" as used herein refers to fluoro, chloro, bromo, or iodo.

As used herein, "heteroaryl" indicates a stable 5- to 7-membered monocyclic or 7- to 10-membered bicyclic heterocyclic ring which contains at least 1 aromatic ring that contains from 1 to 4, or preferably from 1 to 3, heteroatoms chosen from N, O, and S, with remaining ring atoms being carbon. When the total number of S and O atoms in the heteroaryl group exceeds 1, these heteroatoms are not adjacent to one another. It is preferred that the total number of S and O atoms in the heteroaryl group is not more than 2. Examples of heteroaryl groups include, but are not limited to, pyridyl, indolyl, pyrimidinyl, pyridizinyl, pyrazinyl, imidazolyl, oxazolyl, furanyl, thiophenyl, thiazolyl, triazolyl, tetrazolyl, isoxazolyl, quinolinyl, pyrrolyl, pyrazolyl, and 5,6,7,8-tetrahydroisoquinoline. In the term "heteroarylalkyl," heteroaryl and alkyl are as defined above, and the point of attachment is on the alkyl group. This term encompasses, but is not limited to, pyridylmethyl, thiophenylmethyl, and pyrrolyl(1-ethyl).

The term "heterocycloalkyl" is used to indicate saturated cyclic groups containing from 1 to about 3 heteroatoms chosen from N, O, and S, with remaining ring atoms being carbon. Heterocycloalkyl groups have from 3 to about 8 ring atoms, and more typically have from 5 to 7 ring atoms. A $C_2$-$C_7$heterocycloalkyl group contains from 2 to about 7 carbon ring atoms and at least one ring atom chosen from N, O, and S. Examples of heterocycloalkyl groups include morpholinyl, piperazinyl, piperidinyl, and pyrrolidinyl groups.

"Pharmaceutically acceptable salts" includes derivatives of the disclosed compounds wherein the parent compound is modified by making an acid or base salt thereof, and further refers to pharmaceutically acceptable solvates of such compounds and such salts. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional salts and the quaternary ammonium salts of the parent compound formed, for example, from inorganic or organic acids. For example, conventional acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like. The pharmaceutically acceptable salts of the present invention can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable.

Figure 2:
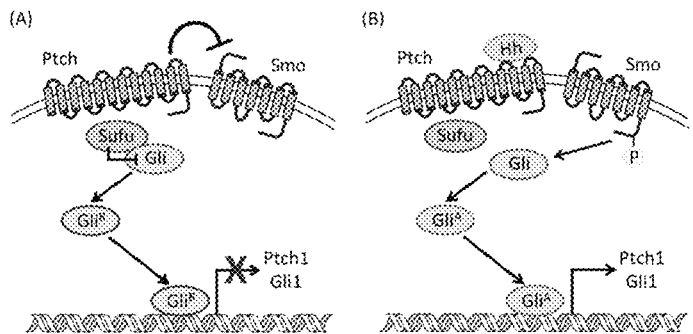
FIG. 2 illustrates the Hh signaling pathway.

The ITZ and PSZ analogues disclosed herein as well as PSZ are expected to have activity as angiogenesis inhibitors and thus to be useful in the treatment of cancer. In certain embodiments, the compounds disclosed herein and PSZ are inhibitors of the Hh signaling pathway and to be particularly useful in the treatment of cancers that are dependent upon the Hh signaling pathway. In cells regulated by the Hh pathway, signal transmission is controlled through a cascade that determines the balance between activator and repressor forms of the Gli family of transcription factors (FIG. 2). In the absence of Hh ligand, Patched (Ptch) suppresses the activity of Smoothened (Smo), a seven-transmembrane protein that is normally observed in endosomes. This inhibition ultimately results in the generation of N-terminal truncated Gli proteins, $Gli^R$, that act as repressors of Hh-responsive genes. Binding of an Hh ligand to Ptch abolishes its inhibition of Smo, leading to the production of full-length Gli activator ($Gli^A$) proteins and resulting in expression of Hh target genes that control proper cell fate determination. Dysregulation of the pathway causes constitutive activation, resulting in uncontrolled proliferation and tumor growth; most notably, in basal cell carcinoma (BCC) and MB. Other cancers that may be treated with Hh signaling pathway inhibitors include chronic myeloid leukemia, lung cancer, prostate cancer, pancreatic cancer and bone cancer.

BCC is the most commonly diagnosed form of cancer in persons of European ancestry (affecting approximately 1 million Americans annually). It has been estimated that approximately 30% of Caucasians living in areas of high sun exposure will develop a BCC during their lifetime and the incidence of BCC in younger populations (especially young females) is rising. While BCC is rarely fatal, it can result in significant morbidity and the large number of affected individuals presents an increasing health burden MB is the most common malignant central nervous system tumor in children, accounting for approximately 20% of pediatric brain tumors and most commonly occurring in children under the age of 8 (40% before the age of 5). Current therapy for pediatric MB patients includes surgery followed by radiation and high-dose chemotherapy. While survival rates for pediatric MB patients have improved over the last ten years, long-term side effects of this course of treatment can include neurocognitive and endocrine deficits as well as growth impairment. In addition, these patients are at an increased risk of developing secondary tumors later in life. Uncontrolled activation of Hh signaling, including both mutation and amplification of key pathway components, has been implicated in approximately 25% of MBs.

In certain embodiments, the compounds described herein are administered to a patient or subject. A "patient" or "subject", used equivalently herein, means mammals and non-mammals. "Mammals" means a member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

The phrase "effective amount," as used herein, means an amount of an agent which is sufficient enough to significantly and positively modify symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically-acceptable excipient(s)/carrier(s) utilized, and like factors within the knowledge and expertise of the attending physician. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

The amount of compound effective for any indicated condition will, of course, vary with the individual subject being treated and is ultimately at the discretion of the medical or veterinary practitioner. The factors to be considered include the condition being treated, the route of administration, the nature of the formulation, the subject's body weight, surface area, age and general condition, and the particular compound to be administered. In general, a suitable effective dose is in the range of about 0.1 to about 500 mg/kg body weight per day, preferably in the range of about 5 to about 350 mg/kg per day. The total daily dose may be given as a single dose, multiple doses, e.g., two to six times per day, or by intravenous infusion for a selected duration. Dosages above or below the range cited above may be administered to the individual patient if desired and necessary.

As used herein, "pharmaceutical composition" means therapeutically effective amounts of the compound together with a pharmaceutically acceptable excipient, such as diluents, preservatives, solubilizers, emulsifiers, and adjuvants. As used herein "pharmaceutically acceptable excipients" are well known to those skilled in the art.

Tablets and capsules for oral administration may be in unit dose form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavoring or coloring agents.

For topical application to the skin, the drug may be made up into a cream, lotion or ointment. Cream or ointment formulations which may be used for the drug are conventional formulations well known in the art. Topical administration includes transdermal formulations such as patches.

For topical application to the eye, the compounds may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The active ingredient may also be administered parenterally in a sterile medium, either subcutaneously, or intravenously, or intrasternally, or intrasternally, or by infusion techniques, in the form of sterile injectable aqueous or oleaginous suspensions. Depending on the vehicle and concentration used, the drug can either be suspended or dissolved in the vehicle. Advantageously, adjuvants such as a local anaesthetic, preservative and buffering agents can be dissolved in the vehicle.

Pharmaceutical compositions may conveniently be presented in unit dosage form and may be prepared by any of the methods well known in the art of pharmacy. The term "unit dosage" or "unit dose" means a predetermined amount of the active ingredient sufficient to be effective for treating an indicated activity or condition. Making each type of pharmaceutical composition includes the step of bringing the active compound into association with a carrier and one or more optional accessory ingredients. In general, the formulations are prepared by uniformly and intimately bringing the active compound into association with a liquid or solid carrier and then, if necessary, shaping the product into the desired unit dosage form.

The invention is further illustrated by the following non-limiting examples.

EXAMPLES

Example 1

Preparation of Analogue 1

The preparation of Analogue 1 predominantly utilized synthetic procedures that have been previously disclosed for the synthesis of ITZ and related azole anti-fungals. Ketalization of 2',4'-dichloroacetophenone with glycerol in the presence of para-toluenesulfonic acid provided dioxolane 3; the primary hydroxyl of which was subsequently tosylated to afford key des-triazole intermediate 4 (Scheme 1).

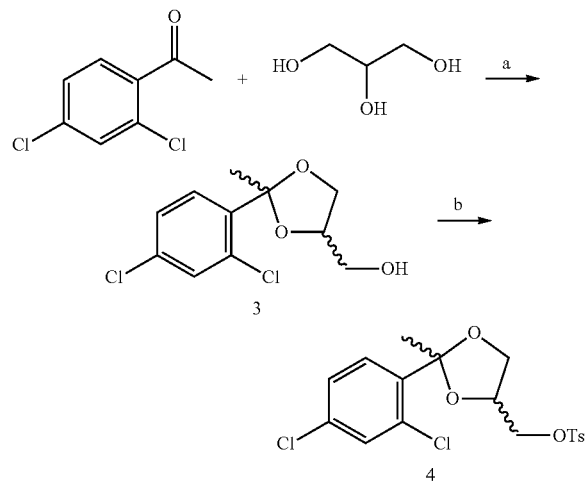

Scheme 1. Preparation of key des-triazole intermediate.[a]

[a]Reagents and conditions: (a) p-TsOH (0.016 eq), reflux, 24 h, 88%; (b) p-TsCl, TEA, DCM, 85%.

Reduction of the nitro functionality in 5 via palladium-catalyzed transfer hydrogenation with hydrazine monohydrate provided the aniline, which was converted to triazolone 9 through the well-characterized phenylcarbamate and semicarbazide intermediates (Scheme 2). Alkylation of the triazolone amine with 2-bromobutane followed by removal of the methyl moiety afforded phenol 11. Base-catalyzed displacement of the tosyl moiety in 4 by the phenol provided the final des-triazole Analogue 1.

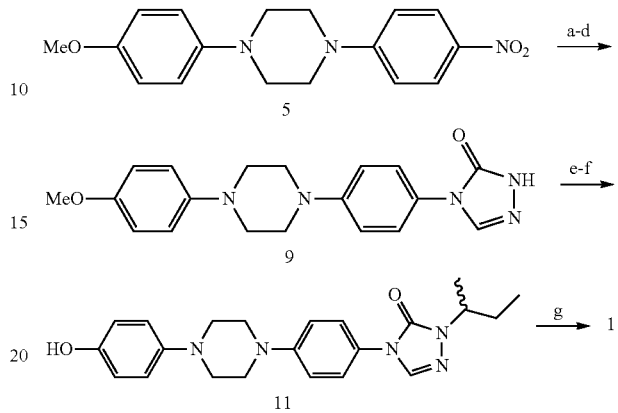

Scheme 2. Preparation of des-triazole ITZ analogue 1.[a]

[a]Reagents and conditions: (a) Pd/C, NH$_2$NH$_2$·H$_2$O (10 eq), reflux, 3.5 h, 71%; (b) Pyr (17 eq), ClCOOPh (1.1 eq), 3 h, 90%; (c) NH$_2$NH$_2$·H$_2$O (5.5 eq), reflux, 3 h, quant; (d) formamidine acetate (4.5 eq), reflux, 3 h, 86%; (e) 2-bromobutane (3.0 eq), 18-crown-6 (1.2 eq), 12 h, 67%; (f) HBr, overnight, 130° C., 83%; (g) intermediate 4 (0.9 eq), NaH (4.5 eq), DMSO, 50-90° C., 12 h, 34%.

Example 2

In Vitro Inhibition of Hh Signaling by Analogue 1

Figure 3:
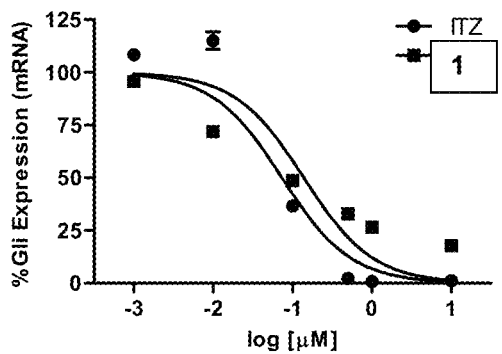
FIG. 3 shows the concentration-dependent down-regulation of endogenous Gli1 mRNA in Hh-dependent mouse embryonic fibroblasts.
Figure 4:
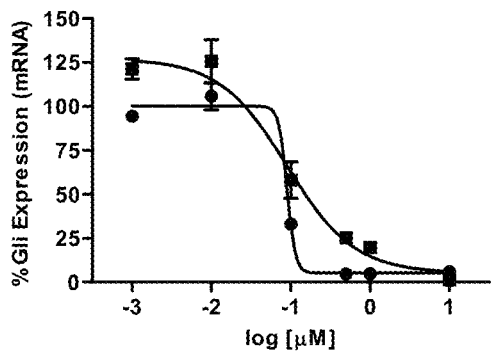
FIG. 4 shows the concentration-dependent down-regulation of endogenous Gli1 mRNA in Hh-dependent BCC.

To determine whether the triazole functionality was required for inhibition of Hh signaling, the ability of Analogue 1 to down-regulate the well-characterized Hh pathway target gene Gli1 in the Hh-dependent C3H10T1/2 cell line was determined. In this cellular model, activation of the pathway with exogenous recombinant Hh ligand results in a characteristic up-regulation of Gli1 mRNA, while concomitant administration of a pathway inhibitor reduces Gli1 expression. Analogue 1 maintained potent down-regulation of Gli1 in this cell line with an IC$_{50}$ value comparable to ITZ (140 and 74 nM, respectively), clearly demonstrating that the triazole functionality is not required for Hh inhibition (FIG. 3 and Table 1). In addition, both ITZ and Analogue 1 were evaluated for their ability to down-regulate endogenous Gli1 expression in ASZ cells, a murine BCC cell line that has been utilized previously by our lab and others as an early stage in vitro model of Hh-dependent cancer. Both ITZ and Analogue 1 reduced Gli1 expression in a concentration-dependent fashion with IC$_{50}$ values comparable to those determined in the C3H10T1/2 cell line (FIG. 4).

TABLE 1

Anti-Hh and anti-proliferative activity of ITZ and Analogue 1.

| Analogue | Hh pathway inhibition[a] | | HUVEC Anti-proliferation |
|---|---|---|---|
| | C3H10T1/2 | ASZ | |
| GDC-0449 | 0.082 ± 0.02[b] | 0.040 ± 0.01 | — |
| ITZ | 0.074 ± 0.02 | 0.14 ± 0.02 | 0.45 ± 0.14 |
| Analogue 1 | 0.14 ± 0.04 | 0.17 ± 0.04 | 23.8 ± 6.7 |

[a]Measured as down-regulation of endogenous Gli1 mRNA.
[b]Values are in μM and represent Mean ± SEM for at least three separate experiments performed in triplicate.

Example 3

Anti-Angiogenic Activity of Analogue 1

Figure 5:
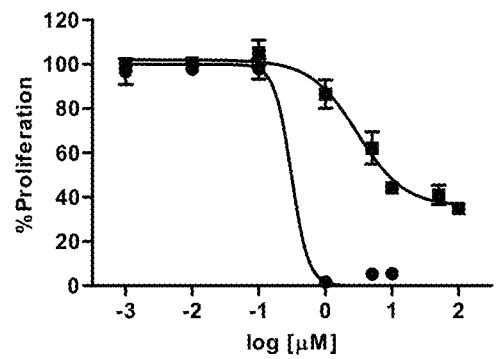
FIG. 5 shows the concentration-dependent inhibition of HUVEC proliferation.

To assess the anti-angiogenic activity of Analogue 1 compared to ITZ, their ability to inhibit proliferation in human umbilical vein epithelial cells (HUVECs) was evaluated. In vivo angiogenesis is dependent on endothelial cell proliferation; therefore, the inhibition of HUVEC proliferation is commonly utilized as an early stage in vitro model of anti-angiogenic activity. In addition, identification of ITZ as an anti-angiogenic compound was established through its ability to inhibit the in vitro proliferation of HUVECs. Interestingly, while ITZ demonstrated potent inhibition of HUVEC proliferation at levels comparable to those previously reported ($GI_{50}$=0.45 µM), Analogue 1 was significantly less active in this assay ($GI_{50}$=23.8 µM) (FIG. 5). To further explore the anti-angiogenic properties of both ITZ and Analogue 1, their ability to inhibit tube formation in HUVECs grown on Matrigel was evaluated. Under normal conditions, HUVECs plated and grown on Matrigel migrate towards each other, align, and form tubes that resemble in vivo capillary beds. This assay is generally considered a more robust model of angiogenesis as it requires several aspects of proper vessel formation, including adhesion, migration, and tube formation. Both ITZ and Analogue 1 significantly inhibited tube formation in this model at 0.1 and 1 µM (FIGS. 10, 11); however, only Analogue 1 demonstrated significant inhibition at 10 nM. Neither compound demonstrated significant anti-proliferative activity at these concentrations at the 24 hour time point utilized for the tube formation assay (data not shown). Taken together, these results indicate that removal of the triazole does not affect the anti-angiogenic activity of the ITZ scaffold while also suggesting an additional mechanism of general toxicity for ITZ in endothelial cells.

Example 4

Effect of Analogue 1 on CYP3A4 Activity

Figure 8:
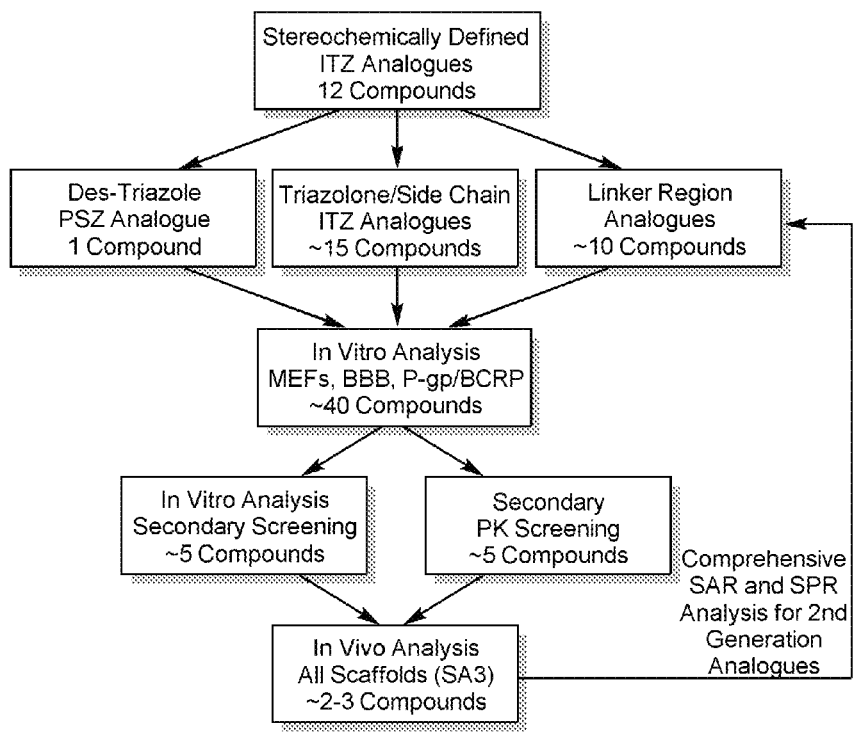
FIG. 8 shows the SAR/SPR generation protocol for itraconazole analogues.

As noted above, a major side-effect of ITZ and other members of the azole class of anti-fungals is potent inhibition of the key metabolic enzyme Cyp3A4. As expected, removal of the triazole moiety completely abolished the anti-CYP3A4 activity of the scaffold. While ITZ significantly inhibited CYP3A4 activity, Analogue 1 was completely inactive ($IC_{50}$ values 50.4 nM and >10 µM, respectively, FIG. 8).

Discussion of Validation of Analogue 1

Analogue 1 is an improved lead compound based on the ITZ scaffold for development as an anti-cancer agent. While removal of the triazole functionality had no effect on the ability of Analogue 1 to inhibit Hh signaling or angiogenesis, it completely abolished its inhibitory effects on CYP3A4. This is of particular importance for cancer patients who are routinely administered drug regimens that may contain multiple drugs whose circulating concentrations are affected by inhibition of CYP3A4. In addition, the results verify that the known target of ITZ, 14LDM, is not responsible for its intriguing anti-cancer properties.

Example 5

Figure 9:
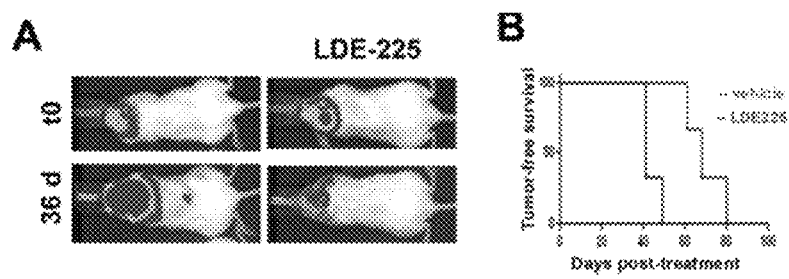
FIG. 9 shows that Hh antagonists increase survival. (A) SHh driven human MB xenografts infected with luciferase virus were transplanted into NSG mice. Bioluminescence images were taken prior to treatment (t0) and after 36-day treatment with vehicle or LDE-225 (20 mg/kg daily). (B) Xenograft-bearing mice treated with vehicle or LDE-225 (20 mg/kg).

Ability of Related Antifungals to Inhibit the Pathway Signaling in C3H10T1/2 Cells at 1 µM In addition to Analogue 1, a series of related azole anti-fungals have been studied for their ability to inhibit pathway signaling in C3H10T1/2 cells at 1 µM. The results from these studies have informed the design and preparation of the analogues described herein (FIG. 9). First, the only compound that demonstrated Hh inhibition comparable to ITZ was Posaconazole (PSZ, % Hh inhibition=96% and 95%, respectively). PSZ a structurally-related, FDA approved triazole antifungal that contains each general structural region of ITZ (triazole, linker, triazolone, and side chain). Second, the structural differences between the triazole regions of ITZ and PSZ suggest that this region is amenable to modification beyond truncation to remove the triazole ring. Third, while removal of the side chain of ITZ had minimal effects on Hh inhibition (analogue 17a), removal of the phenyl/triazolone/side chain region of the scaffold, as in terconazole and ketoconazole, results in a significant reduction in Hh inhibitory activity, suggesting these moieties are required for potent Hh inhibition. Further analysis demonstrated that PSZ inhibited Hh signaling in a concentration-dependent fashion similar to ITZ in C3H10T1/2 cells ($IC_{50}$=10 nM).

Example 6

Preparation of a Des-Triazole PSZ Analogue

A des-triazole PSZ analogue (39, Scheme 5) that is designed to provide additional SAR and stability information for the ITZ/PSZ scaffold will be prepared. First, this analogue will provide evidence as to whether the triazole functionality is non-essential for the anti-Hh activity of the PSZ scaffold. Second, in combination with the data from the cis-2R,4R dioxolane ITZ analogues (25, 29, and 33), this analogue will help determine the optimal orientation around the dioxolane/tetrahydrofuran (THF) moieties in the triazole region. Finally, oxidation at C-5 of the dioxolane moiety in ITZ and subsequent ring opening was shown to be a major metabolic fate of the parent compound. By contrast, significant metabolism of the THF moiety in PSZ has not been identified; therefore, the evaluation of 39 will provide important stability comparisons between the dioxolane and THF moieties of the des-triazole analogues.

Scheme 5. Synthesis of des-triazole PSZ analogue 39

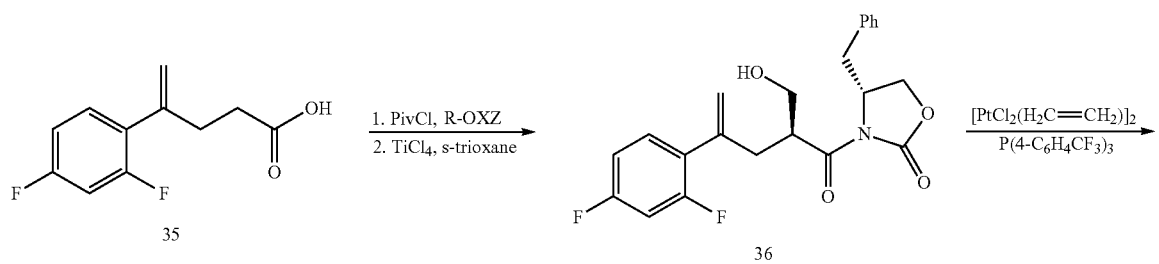

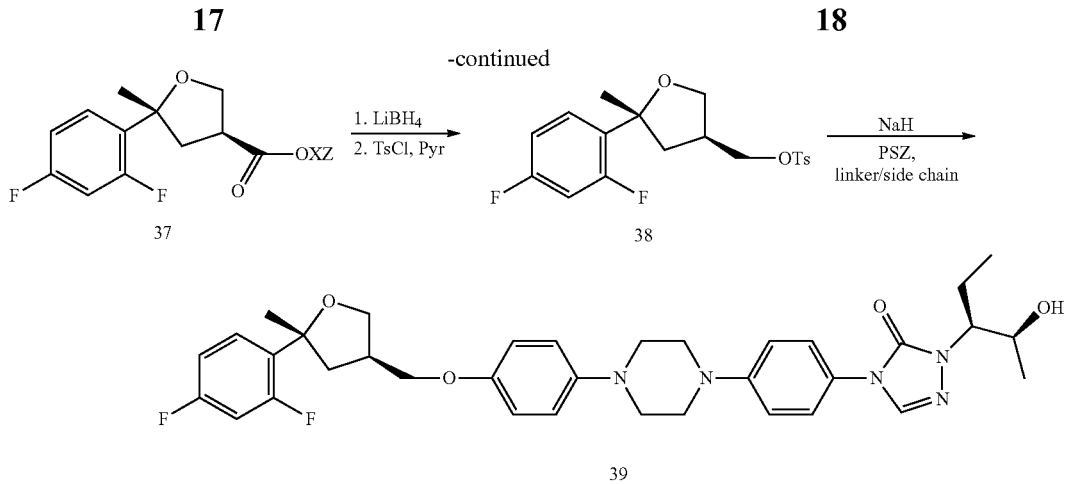

Carboxylic acid 35 is readily available in two synthetic steps from 1,3-difluorobenzene and succinic anhydride. Activation of 35 with pivaloyl chloride followed by derivatization of the resulting anhydride with (R)-4-benzyl-2-oxazolidinone (R-OXZ) provides the chiral imide that can be hydroxymethylated in a diastereoselective fashion to yield 36. Cyclization to the THF moiety can be accomplished in the presence of a platinum(II) complex and tris(4-trifluoromethylphenyl)phosphine to provide 37 as the desired cis imide. It is important to note that similar cyclizations on 36 have afforded an approximately 9:1 mixture of the cis:trans THF imide, suggesting the sterics around the THF ring predispose formation of the cis regioisomer. If significant formation of the trans imide does occur, we will separate the isomers and proceed with both to determine whether the orientation around the THF moiety affects the anti-Hh activity of this scaffold. Lithium borohydride reduction of 37 to the primary alcohol, followed by tosylation will afford key intermediate 38. The PSZ linker/side chain region will be prepared as described and coupled with 38 to provide the final des-triazole PSZ analogue 39.

Example 7

Preparation of Triazolone/Side Chain Region ITZ Analogues a. ITZ analogues with a modified triazolone ring. ITZ analogues incorporating both cyclic and acyclic triazolone mimics designed to probe the sterics, hydrogen bonding, and electronics associated with this region of the scaffold will be prepared. First, the triazolone will be substituted with an acyclic urea moiety to determine whether this region is amenable to increased flexibility (42). Treatment of intermediate amine 40 with sec-butyl isocyanate provides the corresponding urea 41 (Scheme 6). Deprotection of the methyl ether and coupling to des-triazole intermediate 4 will follow standard protocols to yield acyclic analogue 42.

Several cyclic analogues will be prepared to address whether modifications that maintain the more rigid structure of the triazolone improve Hh inhibitory activity. First, the N-1 of the triazolone will be substituted with a carbon to probe the necessity of a hydrogen bond acceptor in this location. Conversion of 40 to the phenyl carbamate and subsequent cyclization in the presence of N-(2,2-dimethoxyethyl)butan-2-amine will provide the cyclized intermediate 43 (Scheme 7, top). Standard protocols will be utilized to unmask the terminal alcohol and couple with 4 to provide analogue 44. In addition, the alkene of the triazolone mimic in 44 will be reduced to yield 46, an analogue that will provide information as to whether saturation of this region has an effect on the Hh inhibitory activity of ITZ (Scheme 6, top). Finally, an analogue that incorporates a six-membered triazolone mimic will be prepared to evaluate how the size of the heterocyclic ring affects Hh inhibition. This compound will be prepared by condensing 1,3-dichloropropane with urea 41 (Scheme 7, bottom). Coupling of 47 and 4 will provide the final 6-membered triazolone mimic 48 for evaluation.

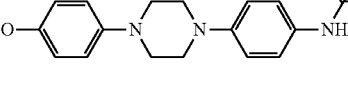

Scheme 7. Preparation of ITZ analogues with 5-and 6-membered triazolone mimics.

Scheme 6. Acyclic triazolone analogue

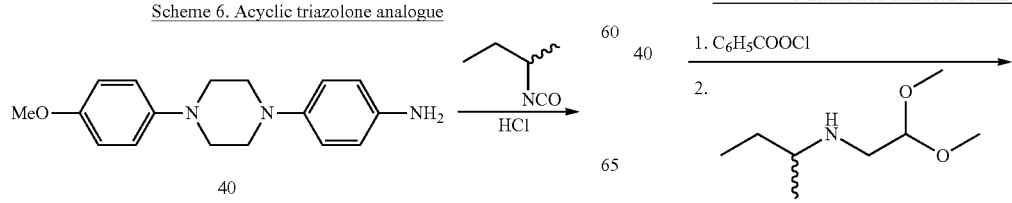

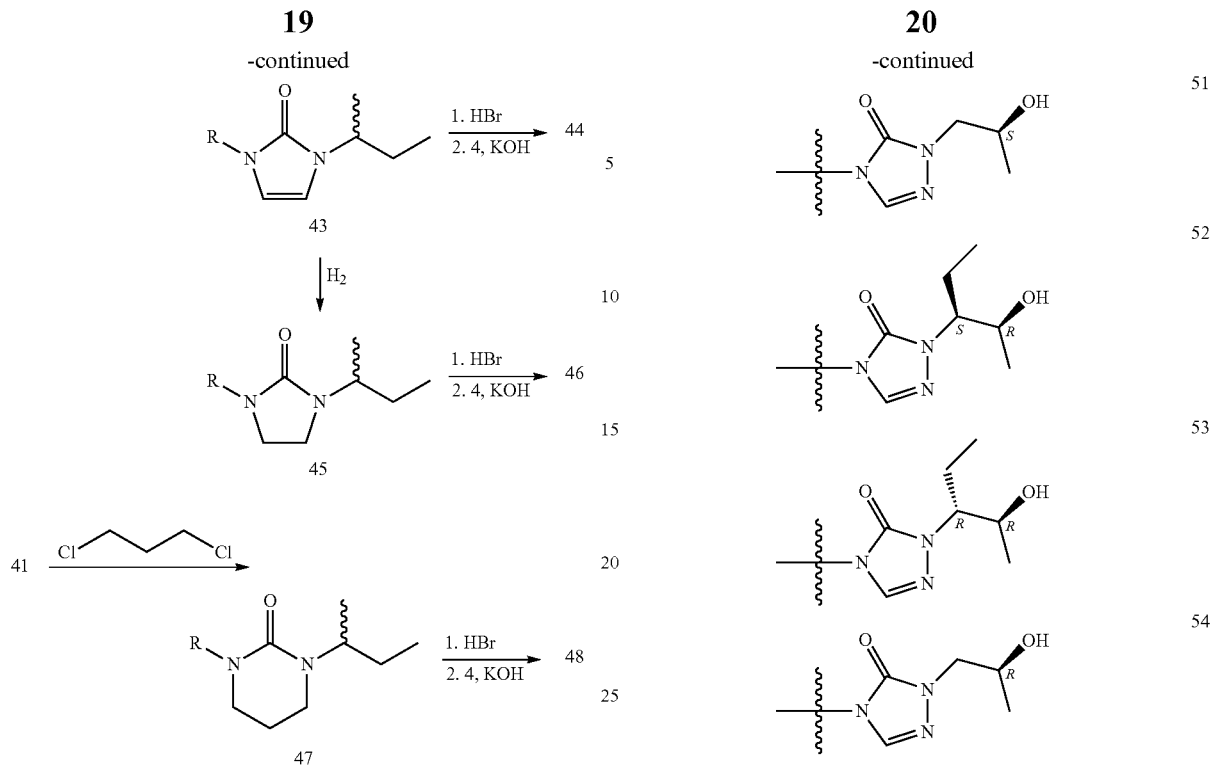

b. Side Chain Region Analogues. Analogues that incorporate stereochemically defined side chains that mimic the PSZ side chain (49-54) will be prepared. (Scheme 8) These analogues will provide further SAR information as to how defined stereochemistry of the side chain affects Hh inhibition. In addition, they will help determine whether the enhanced Hh inhibitory activity of PSZ in the C3H10T1/2 cells is mediated through the hydroxylated side chain. Finally, incorporation of the hydrophilic hydroxyl moiety is predicted to enhance water solubility compared to Analogue 1. Each of these analogues will be prepared using the standard methodology utilized to synthesize either ITZ or PSZ as described above and as is known in the art.

Scheme 8: Side chain reaction analogues

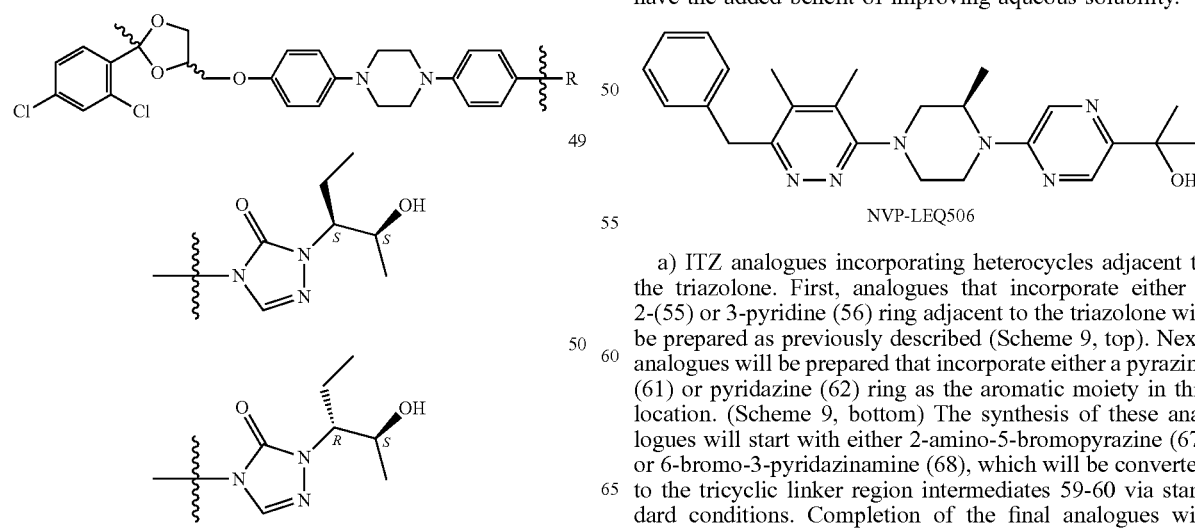

Example 8

Preparation of Linker Region ITZ Analogues

A recent report from a research group at Novartis detailed the optimization of a series of piperizines that ultimately resulted in the generation of NVP-LEQ506 as a potent inhibitor of Hh signaling. Based on the structural similarities between the linker region of ITZ and the central core of NVP-LEQ506 (aryl ring—piperizine—aryl ring), and without being held to theory, it is hypothesized that these two compounds share a similar binding site. For this reason, the linker region ITZ analogues will focus on incorporating pyridine, pyrazine, or pyridazine rings into the scaffold to mimic these moieties in NVP-LEQ506. Not only will these analogues provide key SAR for the linker region of the ITZ scaffold, but incorporation of the heterocycles should also have the added benefit of improving aqueous solubility.

NVP-LEQ506 a) ITZ analogues incorporating heterocycles adjacent to the triazolone. First, analogues that incorporate either a 2-(55) or 3-pyridine (56) ring adjacent to the triazolone will be prepared as previously described (Scheme 9, top). Next, analogues will be prepared that incorporate either a pyrazine (61) or pyridazine (62) ring as the aromatic moiety in this location. (Scheme 9, bottom) The synthesis of these analogues will start with either 2-amino-5-bromopyrazine (67) or 6-bromo-3-pyridazinamine (68), which will be converted to the tricyclic linker region intermediates 59-60 via standard conditions. Completion of the final analogues will follow those synthetic steps previously established herein.

Scheme 9. ITZ analogues incorporating heterocycles adjacent to the des-triazole region.

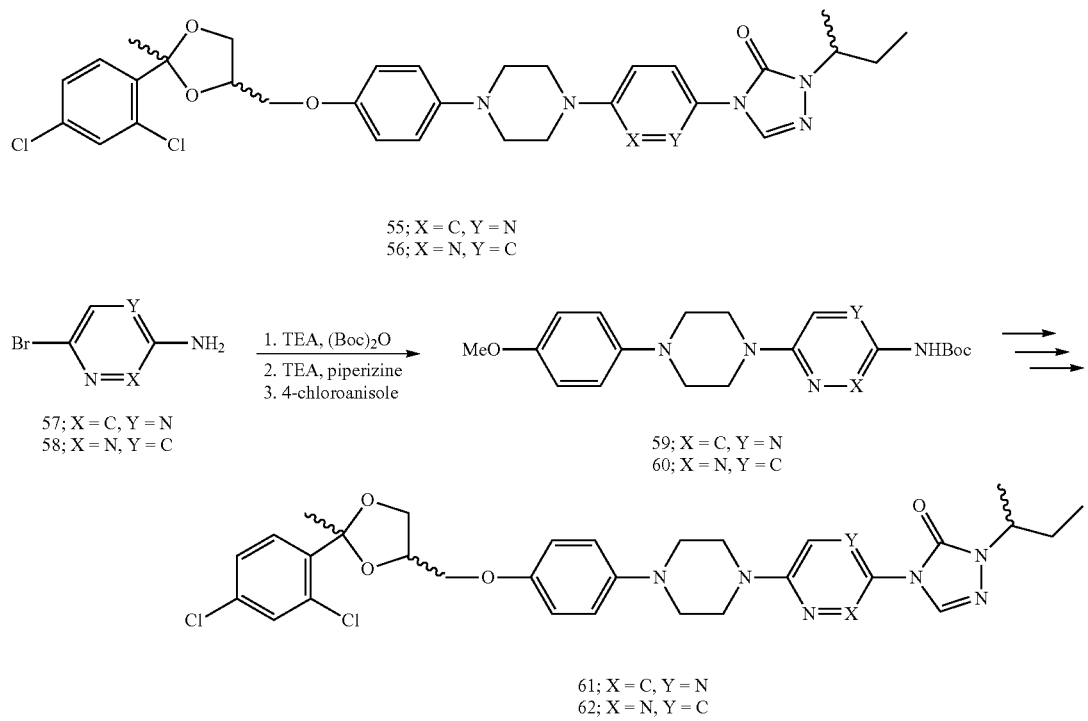

b. ITZ analogues incorporating heterocycles adjacent to the triazole region. Next, analogues that incorporate either a pyridine (71-72), pyridazine (73), or pyrazine (74) ring as the aromatic moiety adjacent to the triazole region will be prepared (Scheme 10). The synthesis of the analogues will start with the requisite commercially available chloromethoxy heterocycles (63-66), which can be converted to the tricylic linker region intermediates 67-70 via a two-step sequence. Completion of the final analogues will be as described herein.

Example 9

Second Generation Analogues

Based on the SAR and SPR results for the analogues described above, optimal substitutions from each region will be incorporated into a single scaffold to generate second generation ITZ analogues. Representative examples of compounds that can be explored based on our SAR/SPR are included below.

Scheme 10. ITZ analogues incorporating heterocycles adjacent to the triazole region.

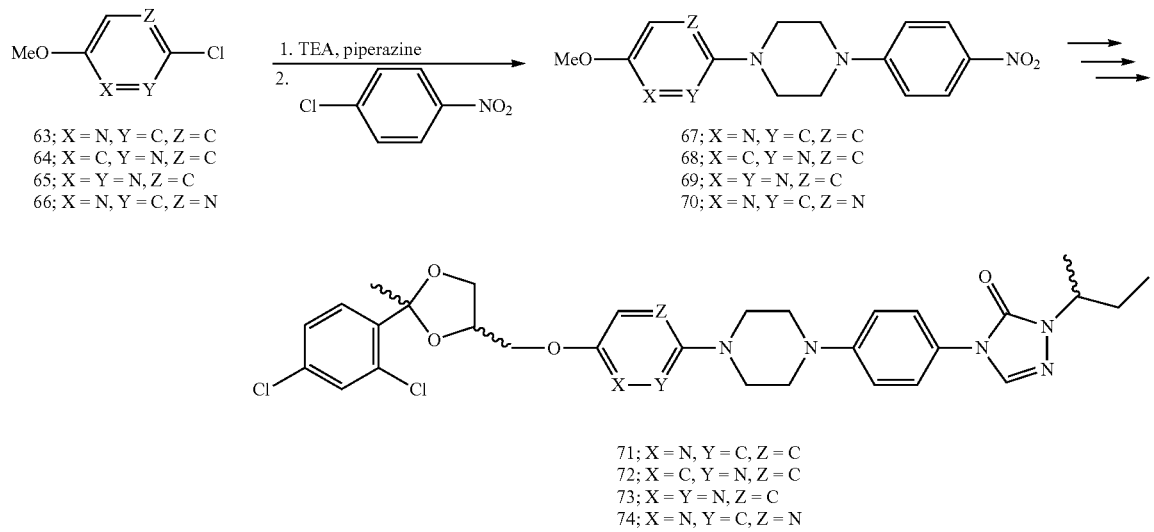

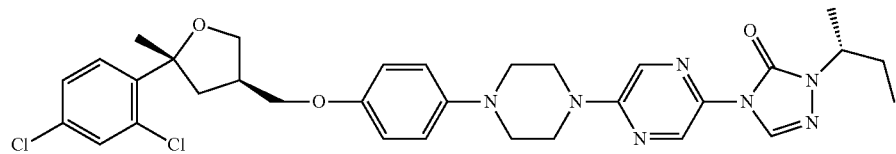

73

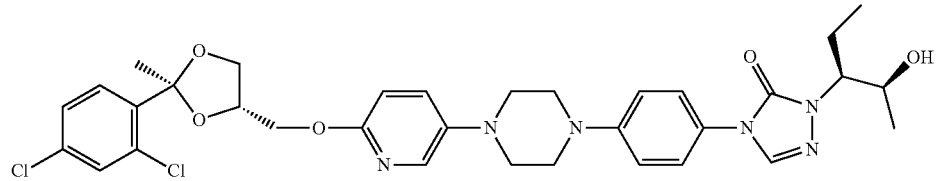

74

Example 10

Triazole Region ITZ Analogues

This series of ITZ analogues will focus on replacing the triazole ring with a suitable bioisostere to probe whether modifications to this moiety enhance the inhibitory effects of ITZ on the Hh pathway while concomitantly decreasing CYP3A4 inhibition (Scheme 11). These compounds will include several analogues (75-80) that incorporate aromatic triazole mimics designed to maintain the general size and shape associated with the triazole while modifying or removing the N-4 associated with the detrimental side effects. In addition, several analogues (81-84) that incorporate non-aromatic moieties will be prepared and evaluated to probe whether an aromatic functionality in this region is essential for Hh inhibition. Synthetic routes to each of these intermediates in Scheme 12 have been extensively characterized in the literature on large scale (>100 g) with minimal chromatographic separations. To date, multigram quantities of each intermediate have been prepared.

Scheme 11: ITS analogues with triazole mimics

75

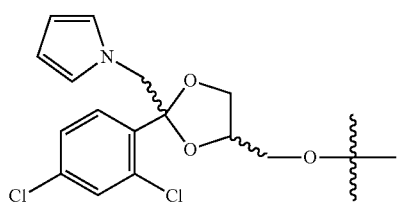

76

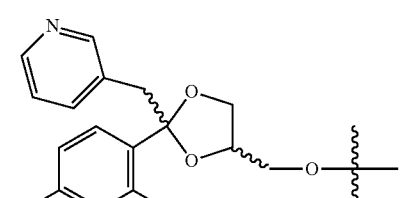

77

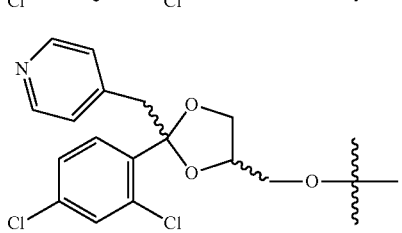

-continued

78

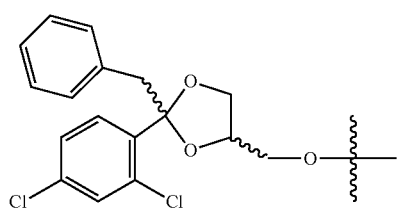

79

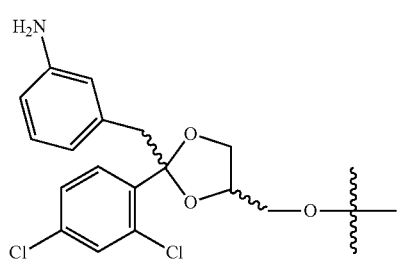

80

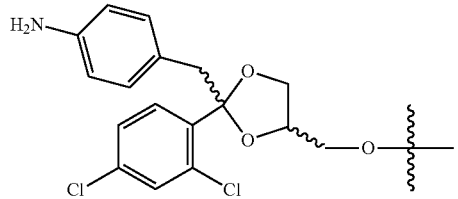

81

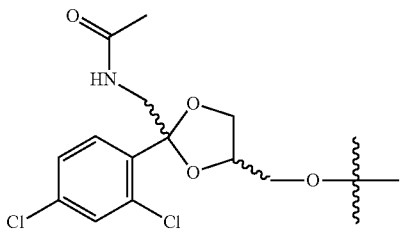

82

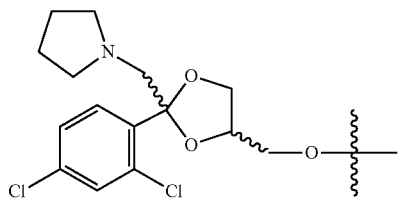

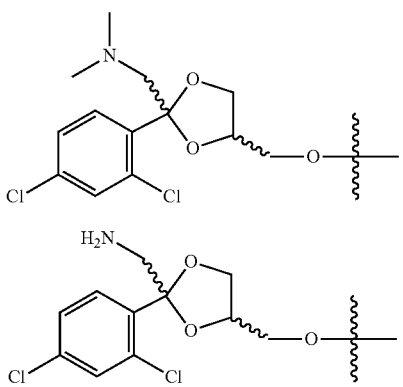

Scheme 12: Key Intermediates for analogue preparation

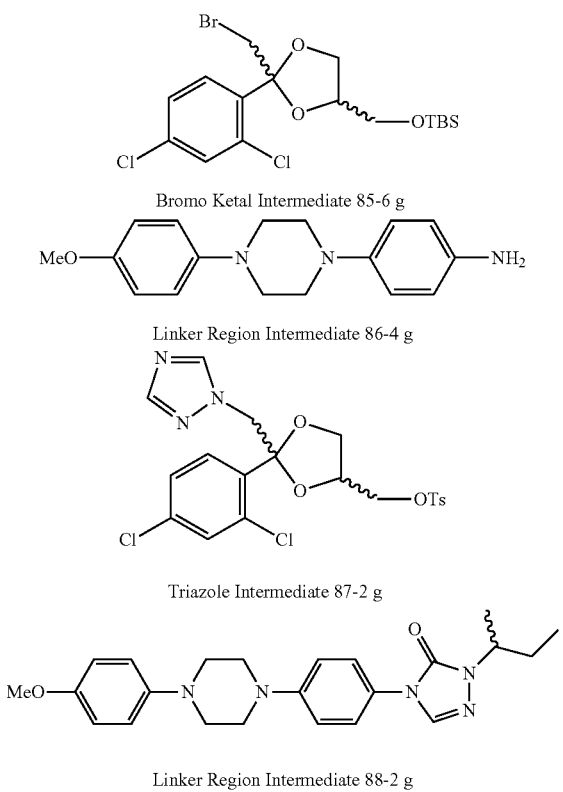

Bromo Ketal Intermediate 85-6 g

Linker Region Intermediate 86-4 g

Triazole Intermediate 87-2 g

Linker Region Intermediate 88-2 g

Analogues 75 and 81-84 that are appended to the central carbon via nitrogen will be prepared by direct displacement of the bromine in intermediate 85 with the requisite nitrogen nucleophile per the standard synthesis of ITZ (Scheme 12). By contrast, incorporating the triazole mimics in analogues 76-80 into intermediate 85 is not as straightforward. Initially, we will explore standard Suzuki and Negishi type cross couplings, to directly append the triazole mimics to 85. In addition, we will also explore coupling the corresponding aryl Grignard reagents to 85 in the presence of catalytic quantities of a copper salt. In the event that direct coupling to the bromo ketal is unsuccessful, a different synthetic route will be utilized to prepare these analogues (Scheme 13). Commercially available 2,4-dichlorobenzaldehyde, 89, will be converted to the corresponding epoxide, 90, through recently published protocols. Epoxide opening at the less substituted carbon with an aryl magnesium bromide followed by reduction of the secondary alcohol will provide the ketone intermediate 91 that can be directly converted to ketal 92 via standard ITZ synthesis conditions. Coupling of these triazole region fragments to intermediate 88 will provide final ITZ analogues 75-84 for evaluation.

Scheme 13: Alternate route to ITZ analogues 76-80

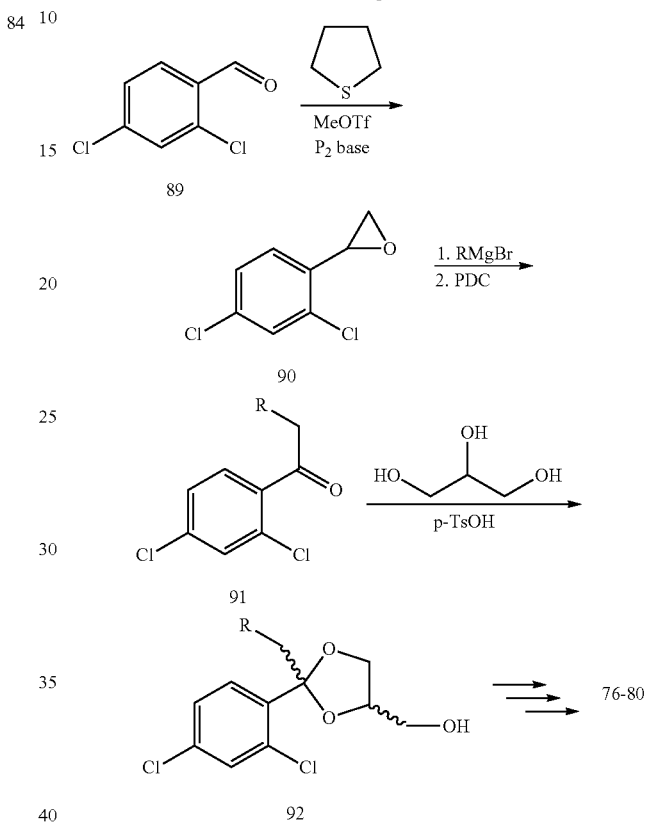

The second series of triazole region ITZ analogues that will be prepared focuses on truncating the triazole region to determine the essential pharmacophore for this portion of the compound. We will take a conservative and systematic approach to modifying this region to provide a better understanding of how each functionality contributes to Hh inhibition (Scheme 14). Analogues that will be prepared include a non-substituted phenyl analogue (93), a des-phenyl analogue (94), a des-triazole analogue (95), and an analogue that removes both the phenyl and triazole rings (96). In addition, intermediate 88 will be evaluated to determine the general necessity of the triazole region.

Scheme 14. Truncated triazole region ITZ analogues

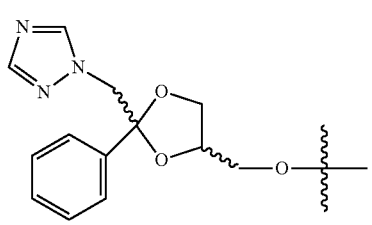

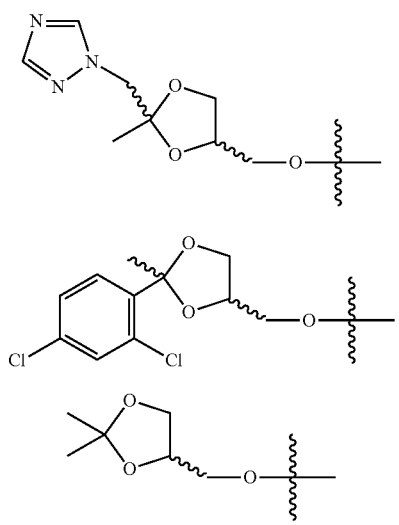

Example 11

In Vitro Hh Inhibitory Activity of ITZ Analogues

Figure 10:
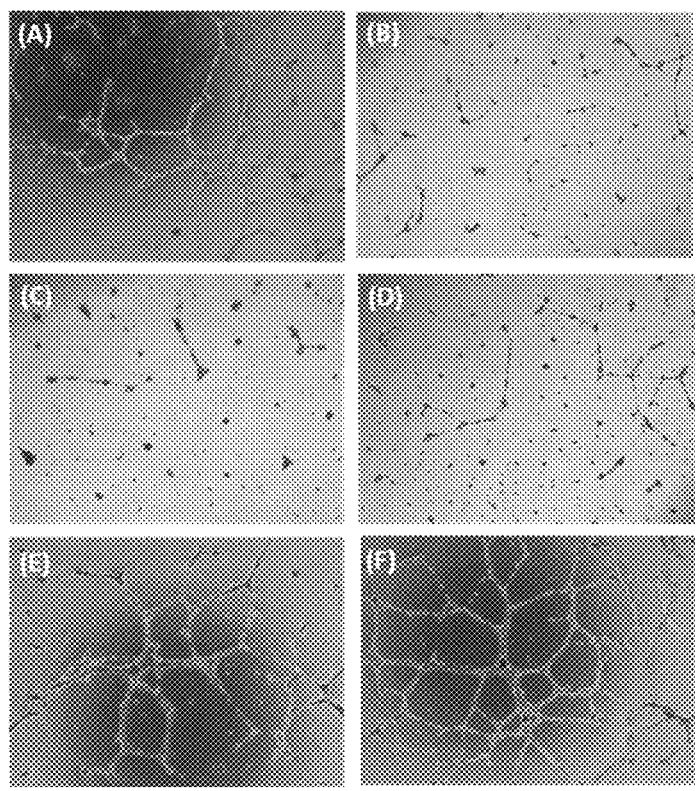
FIG. 10 shows tube formation assays for ITZ and its analogues. (A) DMSO, (B) Suramin, (C) ITZ, (D) 2a, (E) 18a, (F) 21a. All compounds were evaluated at 10 μM and each image is a representative visual field from a single assay. Each assay was repeated at least three distinct times.
Figure 11:
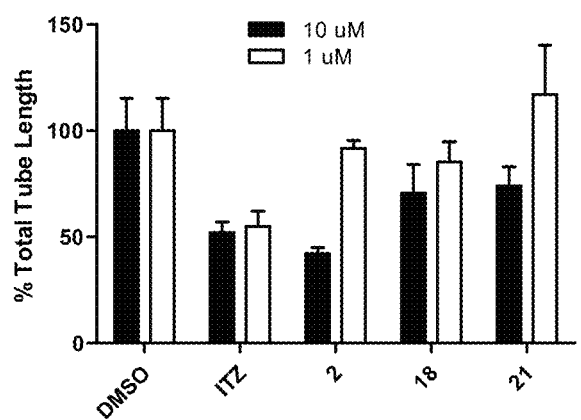
FIG. 11 shows a comparison of total tube length (A) and total tube junctions (B) for ITZ, 2a, 18a, and 21a. DMSO (negative control) was set as 100% tube formation for analysis purposes. Suramin (10 μM) was used as the positive control for each experiment and its ability to inhibit tube length (51.9±7.8%) and tube junctions (57.6±6.1%) was consistent. Data represent the Ave±SEM of at least 3 separate experiments in which ≥5 fields of vision were quantified using ImageJ software.
Figure 11:
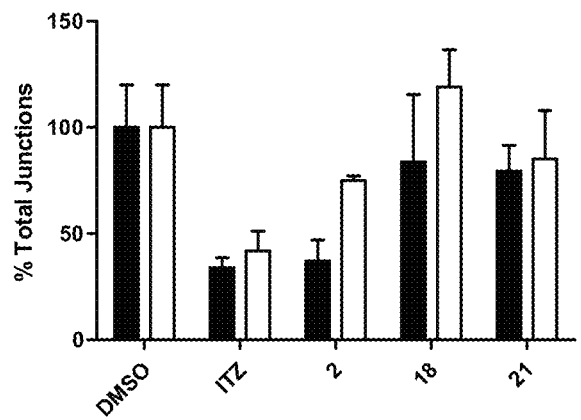

The ITZ analogues will be screened in a panel of biochemical and cell-based assays to evaluate their potential as anti-MB agents that target Hh signaling (FIG. 10). Initially, the analogues will be screened in the following three assays (1) down-regulation of endogenous Gli mRNA in C3H10T1/2 cells at 1 and 0.5 µM, (2) a BBB-PAMPA (Parallel Artificial Membrane Permeability Assay) to predict CNS penetration, and (3) P-gp/BCRP substrate assays. These assays will not only provide an early stage description of SAR for Hh inhibition, but they will also provide valuable information as to how the structural modifications affect essential PK properties for the ITZ scaffold. Compounds that reduce Gli expression below 10% at 1.0 µM and 35% at 0.5 µM will be assessed for their ability to inhibit Hh signaling in a concentration-dependent fashion in multiple, distinct cellular models, including C3H10T1/2 and Hh-dependent MB cells. (Example 13). ITZ analogues that advance to the studies described in Example 13 will also be evaluated in a parallel series of assays to generate a preliminary pharmacokinetic profile for these compounds (Example 14). As these assays are well-established in the literature, only brief descriptions will be provided herein. Where appropriate, ITZ, PSZ, and/or GDC-0449 will be used as positive controls. GraphPad Prism software is used for all graphing and statistical analysis. Specifically, $IC_{50}$ and $GI_{50}$ values are calculated via non-linear regression analysis and values represent mean±SEM for at least two separate experiments performed in triplicate. Two-sided Student's t-tests are utilized to determine significance between treated and non-treated samples when a single concentration is evaluated. One-way ANOVA followed by Tukey's test is utilized to determine significance related to the following: (1) response to multiple concentrations of the same analogue and (2) response to multiple analogues (including controls) at a single concentration.

Background: The last twenty years have seen a concerted effort to develop computational models and statistical equations that can be utilized during the early stages of drug design to accurately predict whether a small molecule will penetrate the BBB. Common parameters associated with these models include molecular weight (MW), lipophilicity (logP or logD), total polar surface area (tPSA), H-bonding properties, and 3D molecular interaction fields. While many of these equations have proven useful at predicting BBB permeability, none of them is absolute and all demonstrate several shortfalls. On average, the correlations between predicted BBB penetration and experimentally determined brain concentrations are good, but not absolute ($r^2$ values=0.72-0.92) and correct classifications are generally approximately 85%. These models predict the probability that a small molecule will passively diffuse through the BBB, but they cannot account for compounds that are actively transported into the CNS or those that are actively effluxed from the brain. In addition, statistical equations can only predict total drug concentration and not the free drug concentration after plasma protein binding. Finally, many disease states are known to affect BBB integrity and can actually result in enhanced permeability that would not be predicted from any of the standard computational models.

As noted above, ITZ increased survival in an orthotopic model of Hh-dependent MB following oral administration, providing strong evidence that it accumulates in the brain in efficacious concentrations within the context of murine models of intracranial MB. Another parameter that must be considered for developing drugs that target intracranial tumors is to what extent they are actively effluxed from the brain. Currently, there are two multidrug transporters that are recognized as the major efflux pumps in the BBB; P-glycoprotein (P-gp, ABCB1 or MDR1) and breast cancer resistance protein (BCRP, ABCG2). Two separate studies evaluating brain accumulation of ITZ demonstrated that concentrations of the drug in the brain were significantly increased in mdr 1a knockout mice or when a P-gp inhibitor (verapamil) was co-administered, suggesting ITZ is a substrate for P-gp efflux. While ITZ has been identified as a modest inhibitor of BCRP ($IC_{50}$ approximately 1 µM), studies to determine whether it is a substrate for BCRP-mediated efflux have not been reported.

With all of this as context, it is clear that BBB penetration and brain accumulation are highly dependent on multiple factors, many of which are specific to the individual scaffold of the drug. Determining the factors that contribute both to BBB penetration and efflux of the ITZ scaffold is of equal importance to Hh inhibitory ability with respect to designing and developing analogues that exhibit improved activity against intracranial tumors. For this reason, we will determine both SAR for Hh inhibition and SPR for brain penetration and accumulation during the early stages of in vitro analysis for the ITZ analogues.

Initial in vitro assays for Hh inhibition and BBB penetration and accumulation. With respect to Hh inhibition, all analogues will be evaluated for their ability to down-regulate endogenous Gli mRNA in the Hh-dependent C3H10T1/2 cell line at two concentrations (1 µM and 0.5 µM). Hh inhibition for both ITZ and 1 are comparable at these two concentrations (approximately 98% and 70%, respectively) and they will provide an appropriate measure of the inhibitory activity of the additional analogues. This assay will be performed as known in the art and in the same manner utilized for the preliminary data reported for 1.

Each analogue will also be evaluated in assays to develop SPR for the ability of the scaffold to penetrate the BBB and accumulate in the brain. First, a standard BBB-PAMPA assay will be used to predict the ability to passively diffuse across the BBB. In this method, an artificial membrane that has been designed to mimic the BBB is immobilized on a filter between a donor and acceptor compartment. ITZ or analogue (10 µM) is added to the donor compartment and following a 30 min incubation period, compound concentrations in both compartments are quantified via LC/MS/MS and this data will be utilized to determine the apparent permeability (Papp) as a predictor of BBB penetration. Standard P-gp/BCRP transporter assays are also performed to determine to what extent the ITZ analogues are actively effluxed from the brain. For these assays, Madin Darby canine kidney cells (MDCK) are transfected with either P-gp or BCRP and grown to confluence on filter inserts in in a transwell apparatus analogous to that used for the PAMPA assay. Analogue (10 µM) is added to either the donor or acceptor compartment and following a 60 min incubation period, compound concentrations in both compartments are quantified via LC/MS/MS. These data will be utilized to calculate an efflux ratio. Should the results suggest an analogue is a substrate for either transporter, the assay will be repeated in the presence of a P-gp (verapamil) or BCRP (Elacridar) inhibitor to determine whether efflux is suppressed. The fluorescent dye lucifer yellow will be utilized to ensure membrane integrity in the transporter assays. The BBB-PAMPA assay and both transporter assays will be performed in collaboration with the Sanford-Burnham Exploratory Pharmacology Core Facility.

In preliminary studies with PSZ in the BBB-PAMPA assay, an apparent permeability (Pap) of 46 was measured, suggesting that PSZ is moderately permeable. For reference, verapamil is considered highly permeable with a Papp of 170; corticosterone is moderately permeable with a Papp of 15, and theophylline is impermeable with a Papp of 0.15.

In addition, it was tested whether posaconazole is a substrate of P-gp or BRCP, and posaconazole was not a substrate of either, suggesting that if it gets in the brain, it is not actively removed by known mechanisms.

Example 12

Secondary In Vitro Assays for Concentration-Dependent Inhibition of Hh Signaling Analogues that reduce Gli mRNA expression comparably to ITZ and 1 at 1 (<10%) and 0.5 (<35%) µM and effectively penetrate the BBB-PAMPA filter will be further evaluated for their ability to down-regulate endogenous Gli and Ptch in C3H10T1/2 cells in a dose-dependent fashion to establish an $IC_{50}$ value for Hh inhibition in this cell line. These analogues will also be evaluated for their effects on Hh pathway signaling in the presence of a mutated form of SMO (D477G) that confers resistance to multiple Hh pathway inhibitors including GDC-0449. For this assay, the wild-type and D477G Smo constructs will be transiently transfected into C3H10T1/2 cells and inhibition of pathway signaling assessed as previously described. Compounds that exhibit $IC_{50}$ values less than 200 nM and retain potent Hh inhibition in the presence of mutant Smo will be considered for further evaluation in the secondary analyses described below. Of note, the benchmarks that have been set for advancing compounds to the next phase are primarily based on the activity of ITZ and 1; however, these benchmark metrics will be continually evaluated to ensure that an appropriate number of analogues are being advanced to the next stage.

ITZ analogues that exhibit Hh inhibition in C3H10T1/2 cells per the guidelines established above will be further evaluated for their ability to modulate Hh signaling in a dose-dependent fashion in cells from Hh-dependent models of MB, using protocols previously established in the art. MB cells will be isolated from conditional patched knockout (Math1-CreER$^{T2}$; Ptch$^{flox/flox}$) mice and cultured as described in the art. ITZ analogues will be evaluated for their ability to down-regulate endogenous Gli expression and for their effects on cell proliferation ($^3$H-thymidine incorporation and cell cycle analysis), differentiation (expression of Math1, TuJ1 and MEF2D) and survival (cleaved caspase expression, Annexin V/propidium iodide staining).

To further explore the efficacy of ITZ analogues against human MB, compounds will be evaluated in patient-derived xenograft (PDX) cells, which represent unique tools to study Hh pathway inhibitors for their anti-MB activity. PDX lines are created by isolating cells from surgically-resected human MB tissue and directly implanting them into the cerebellum of immunocompromised (NOD-SCID-IL2Rgamma or NSG) mice. Cells are passaged from mouse to mouse, and are never grown in culture except for short-term experiments. Tumor cells propagated in this manner retain many of the molecular and cellular properties of the tumors from which they were derived. A panel of MB PDX lines has been established in the art, including several that exhibit Hh pathway activation. For these experiments, tumor bearing mice will be sacrificed and tumor cells dissociated and plated in vitro. The effect of ITZ analogues on Gli expression, proliferation, and survival of the PDX cells will be evaluated using the assays described above. It is important to note that while the PDX cells were directly isolated from human medulloblastoma tumors, we have no information that would allow us to identify the individuals from whom the samples were obtained.

Example 13

Preliminary Pharmacokinetic Studies

Understanding the pharmacokinetic (PK) profile of a potential drug candidate during the early stages of its development has become a key strategy for improving its drug-like properties. The final in vitro studies that will be performed will provide an evaluation of the following key PK parameters: solubility, stability (metabolic and chemical), and intestinal permeability. The results from these studies will provide an overall PK profile for each class of analogues, aid in developing formulations for IP and oral dosing, and predict oral bioavailability.

a. Solubility. ITZ was initially available in several capsule formulations; however, the plasma and tissue concentrations following administration of these capsules were highly variable and dependent on numerous patient-specific parameters. Studies on inclusion complexes between ITZ and 2-hydroxypropyl-β-cyclodextrin (2β-CD) demonstrated that these complexes significantly enhanced both solubility and oral bioavailability of ITZ. These initial results led to the development of an oral solution of ITZ (Sporanox®) containing ITZ (10 mg/mL) and 2β-CD (400 mg/mL) with a pH of 2, which demonstrates an improved oral bioavailability and more consistent tissue distribution and plasma concentrations. Many of the modifications of the ITZ scaffold will also affect the logP and aqueous solubility of the ITZ scaffold (i.e., removal of the triazole, incorporation of hydroxyl(s) in the side chain and pyridine rings in the linker region). First, standard protocols will be utilized to determine kinetic solubility, a common early stage measure of aqueous solubility. The standard benchmark for kinetic solubility is >60 µg/mL as compounds that obtain this value generally demonstrate enhanced bioavailability following both oral and systemic dosing. ITZ analogues with promising potency that do not reach this solubility threshold in water will be prepared as inclusion complexes with 2β-CD per previously published protocols to enhance solubility in preparation for the in vivo studies.

b. Chemical and metabolic stability. Next, a series of in vitro assays will be performed to assess the chemical and metabolic stability of the optimal ITZ analogues. Standard procedures will be utilized to evaluate chemical stability in simulated gastric fluid (pH 1.2), simulated intestinal fluid (pH 7.4), and water. In addition, if complexation is necessary to achieve the benchmark solubility, chemical stability will also be assessed in this solution. Standard assays to characterize the overall metabolic stability and identify major metabolites for our ITZ analogues will also be performed. Numerous HPLC and LC/MS assays for analyzing clinical samples containing ITZ and its metabolites have been developed. For this reason, these previously optimized conditions (HPLC method, concentration, incubation time, detection method, etc.) will be utilized as a basis for these assays. ITZ analogues will be incubated in pooled human or rat liver microsomes (BD Biosciences) and samples analyzed at various time points for metabolic stability. Resulting metabolites will be characterized via LC/MS and NMR and major metabolites will be synthesized and characterized via the methods described for Analogue 1 to determine their biological activity with respect to the Hh signaling pathway. Each ITZ analogue will also be evaluated for its ability to inhibit a panel of major hepatic drug-metabolizing CYP450 enzymes (1A2, 2A6, 2C9, 2C19, 2D6, and 3A4). Several of these enzymes are known to be inhibited by various azoles including ITZ (2A6, 2C9, and 3A4). For this assay, ITZ or analogue will be incubated with human CYP450 Supersomes™ (BD Biosciences) as described in the art and evaluation of inhibitory activity will be assessed with the P450-Glo™ Assay Kit (Promega) via the manufacturer's protocols.

c. Intestinal permeability. Finally, Caco-2 cell monolayers will be utilized as a predictor of intestinal absorption and oral bioavailability. Technological advances in assays for oral permeability have led to the development of commercially available assay kits that allow for drug transport studies in a 96-well plate format (MultiScreen® Caco-2 Assay System). For these assays, analogues will be evaluated at 10 μM following the manufacturer's suggested protocol. Following incubation, analogue quantification in both the apical and basolateral chambers will be analyzed via LC/MS/MS and this data will be utilized to determine the apparent permeability (Papp) as a predictor of intestinal absorption. The small molecule mannitol will be used as a control for monolayer integrity.

It is anticipated that the in vitro studies will result in the identification of SAR for several regions of the ITZ scaffold with respect to selective inhibition of Hh signaling in C3H10T1/2 and Hh-dependent MB cells. In addition, the solubility, stability, and permeability studies will provide essential early stage PK parameters for developing the ITZ scaffold as an anti-MB chemotherapeutic. Taken together, these results will identify ITZ analogues with potent anti-Hh activity and improved drug-like properties for in vivo studies. Based on our identification of Analogue 1 as a potent analogue of ITZ and the inherent activity of ITZ in many of these assays, it is anticipated that multiple analogues will meet the potency benchmarks. In addition, the fact that ITZ increased survival in an orthotopic model of MB strongly suggests that these analogues will be able to cross the BBB at effective doses, irrespective of the in vitro results.

Example 14

Evaluation of ITZ Analogues in Murine Models of Hh-Dependent MB

The compounds selected on the basis of the in vitro assays of Examples 12-14 will first be evaluated for their ability to inhibit the growth of Hh-dependent MBs in flank allografts (Example 15). This allograft model will not only allow for determination of the anti-Hh and anti-MB activity of ITZ and its analogues irrespective of brain penetration, but will also provide preliminary information for the treatment of other Hh-dependent peripheral cancers. Analogues that exhibit activity in flank allografts will be evaluated for their ability to cross the BBB and accumulate in the brain (Example 16). Compounds that reach efficacious concentrations in the brain will then be evaluated for their efficacy in intracranial tumors (Example 17). Finally, ITZ analogues that exhibit potent in vivo activity will be evaluated in a series of studies to determine their propensity to induce resistance as a prospective step to improve the overall drug discovery process of ITZ analogues as anti-MB agents that target the Hh signaling pathway (Example 18).

Background and Preliminary Studies. Mouse models are invaluable tools for studying tumor biology and developing novel therapeutics. Mice with mutations in Ptch have been utilized to develop tumors that closely mimic human Hh-associated MB. These animals have been used to study many aspects of Hh tumor biology, including the cell of origin, the early stages of tumorigenesis, and the genetic lesions that cooperate with loss of Ptch to induce tumor formation. In addition, Ptch mutant mice have been used as a platform for preclinical testing of Hh pathway inhibitors and other therapeutic agents. Most importantly for the purposes of the proposed studies, the tumors that develop in Ptch$^{-/-}$ mice harbor mutations upstream of Smo. As ITZ has been proposed to inhibit Hh signaling via direct binding to Smo, these mice represent an excellent model to study the anti-Hh and anti-cancer properties of ITZ analogues in vivo.

Mouse models of MB, including genetically engineered mouse (GEM) and patient-derived xenograft (PDX) models, have been used for preclinical studies of therapeutic agents and treating MB in vivo. As a proof of principle experiment for evaluating Hh pathway inhibitors in these models, a recent study was conducted using LDE-225, a small molecule Hh pathway inhibitor currently in multiple clinical trials for the treatment of several types of human cancer. For these studies, tumor cells from a PDX line (with a mutation in PTCH1) were infected with luciferase viruses and implanted into the cerebellum of immunocompromised NSG mice. After four weeks, daily oral gavage was initiated with LDE-225 or vehicle and animals were monitored by bioluminescent imaging. LDE-225 caused tumor regression and prolonged survival (FIGS. 11A and 11B). The results from these studies verify that this model is suitable for analysis of Hh pathway inhibitors and demonstrate that the investigators have the expertise necessary to conduct the proposed experiments.

Anti-MB studies in flank allograft models of Hh-dependent MB. Evaluating the ITZ analogues in flank allografts is an important first step to probing the in vivo activity of the compounds. These studies will provide information as to the ability of the analogues to inhibit pathway signaling and decrease tumor growth in an Hh-dependent murine model of MB, irrespective of their ability to cross the BBB and accumulate in the brain. In addition, comparing the effects of the ITZ analogues after IP and oral dosing will provide preliminary information with respect to the oral bioavailability of the analogues. Finally, tumors that do not respond to ITZ or analogue treatment will be a valuable source of information for determining the potential resistance mechanisms that are induced for this particular scaffold (see Example 17). It is important to note that the initial doses chosen for the in vivo studies are based on the doses for which ITZ has demonstrated potent anti-Hh and anti-MB activity in vivo. These doses will be modified as needed should the analogues prove more or less active than ITZ in vivo.

For the flank allografts, Math1-CreER$^{T2}$; Ptch$^{flox/flox}$ tumor cells will be infected with viruses encoding a GFP-luciferase fusion protein (pGreenFire, System Biosciences) that allows FACS sorting as well as bioluminescent imaging of tumor cells. Infected (FACS-sorted GFP+) cells will be mixed 1:1 with growth factor-reduced matrigel and implanted into the flanks of Nu/Nu mice ($2 \times 10^6$ cells/host). Tumor growth will be monitored using calipers as well as bioluminescence imaging. When tumors reach a volume of approximately 100 mm$^3$, animals with comparably sized tumors will be segregated into treatment groups (ITZ, ITZ analogue, or vehicle) and treatment will be initiated. Based on survival power analysis, assuming the analog inhibitors work at least as well as other Hh antagonists, 20 mice per group will be needed for 80% power (p-value=0.05). Animals will be given daily intraperitoneal (i.p. 50 mg/kg) or oral (100 mg/kg) doses and sacrificed when the largest tumor in the treatment group reaches 2 cm in any dimension. After sacrifice, tumors will be collected, weighed, and photographed to determine the effects of compounds on overall tumor size. For a subset of animals from each group, tumor tissue will be processed for RNA isolation, and Gli1 levels will be assessed by qPCR. For an additional set of animals, tissue will be fixed, sectioned, and stained with markers of proliferation (Ki67), differentiation (Math1, TuJ1, MEF2D) and apoptosis (cleaved caspase).

Example 15

In Vivo Blood Brain Barrier Penetration

Analogues that exhibit anti-Hh and anti-MB effects in flank allografts will be evaluated to determine their ability to cross the BBB and accumulate in the brain. Initially ITZ, analogue, or fluconazole (an azole antifungal known to cross the BBB) will be administered via either i.p. injection or oral gavage to tumor-bearing mice to identify how the structural modifications affect BBB penetration and accumulation. The dose to be used for these studies will be determined based on the results of the allograft studies in Example 15. Animals (4 mice per time point) will be sacrificed 1, 3, 6, and 12 hrs post-injection, and plasma and brain tissue will be frozen and submitted to the EPC for analysis. Drug concentrations in plasma and brain will be measured by LC/MS/MS and ratios between the two determined. If analogues achieve brain concentrations corresponding to those determined to be effective in the in vitro studies, these compounds will immediately move to intracranial tumor studies described below. In the event that BBB accumulation is low, the study will be repeated and the analogues will be coadministered with either verapamil (5 mg/kg), an inhibitor of P-gp previously shown to significantly enhance brain concentrations of ITZ, or Elacridar (10 mg/kg), a dual inhibitor of both P-gp and BCRP. Comparing the results from both transport inhibitors will determine whether ITZ efflux is mediated by one or both of the major multi-drug transporters in vivo.

Example 16

Anti-MB Studies in Intracranial Tumors

Agents that are determined to be effective in flank allografts and accumulate at therapeutic concentrations in the brain will be evaluated for their effect on the growth of intracranial tumors. For these studies, GFP-luciferase infected Math1-CreER$^{T2}$; Ptch$^{flox/flox}$ tumor cells will be sorted and implanted into cerebella of NSG mice. When tumors are detectable by bioluminescence (approximately 4 weeks after transplantation), animals with comparably sized tumors will be segregated into treatments groups (ITZ, ITZ analogues, or vehicle) and treatment will be initiated. Animals (20 mice per treatment group) will be given daily i.p. (50 mg/kg) or oral (100 mg/kg) doses of each compound. One cohort of mice will be sacrificed after 30 days and tumor tissue analyzed as described above to evaluate the effects of ITZ and analogues of Gli1 expression, proliferation, differentiation, and apoptosis. A second cohort of mice will be followed until onset of symptoms to assess the effects of analogues on animal survival.

Example 17

Prospective Resistance Studies

As noted above, resistance has developed for each of the small molecule Hh pathway inhibitors that have been extensively studied in preclinical murine models of MB; therefore, it is useful to explore the potential of both ITZ and its analogues to promote tumor resistance. These studies will be performed in combination with the in vivo tumor analyses described in Examples 15 and 16 above. Specifically, tumors from both studies that do not respond to therapeutic treatment will be assessed for the resistance mechanisms previously identified for GDC-0449, NVP-LDE225, and IPI-926 following the protocols used for these compounds. Genomic DNA will be extracted from the tumors, amplified via PCR, and all Smo exons will be sequenced to identify missense point mutations. In addition, mRNA and protein samples will be isolated from the tumors and analyzed for mutation or amplification of key Hh pathway components downstream of Smo (Sufu, Gli1, Gli2, Gli3, etc.) that could potentially contribute to the development of resistance. Finally, tumor samples will be evaluated for the up-regulation of P-gp and BCRP (mRNA and protein) to determine whether developed resistance could be linked to increased analogue efflux.

The studies described in Examples 15-18 will provide essential data regarding the potential of ITZ analogues to inhibit Hh-dependent MB in vivo. First, they will identify to what extent ITZ and its analogues cross the BBB in animal models of MB and determine whether addition of a transport inhibitor may increase uptake. Second, by directly comparing the analogues in flank allografts and intracranial tumors we will gain additional insight into whether the BBB affects the anti-Hh and anti-MB properties of the compounds. Finally, we will learn whether resistance to the ITZ scaffold develops in a fashion similar to that seen for the other Hh pathway inhibitors that have entered clinical trials for MB.

Example 18

Angiogenesis Inhibition Assays

HUVEC Cell Viability and Proliferation. HUVEC cell viability and proliferation will be assessed by measuring cellular metabolic activity using MTT (viability) or MTS (proliferation) according to the manufacturer's instructions.

HUVECs (3000 cells/well) are seeded in a 96-well plate and allowed to attach overnight. Cells are treated with varying concentrations of ITZ or Analogue; viability is assessed after 24 h with MTT and proliferation was assessed after 72 h with MTS. For viability, the final value is a corrected optical density (570 nm-690 nm). All viability and GI50 values are from a minimum of three separate experiments performed in triplicate.

Tube Formation Assay. Matrigel (BD Biosciences) is diluted with DMEM to 3 mg/ml and used to coat the wells of a 24-well tissue culture dish. Plates are incubated at room temperature for 30 min until the matrigel solidifies. HUVECs are suspended in M199 media with 1% FBS and penicillin/streptomycin and 40,000 cells are added to each well. Plates are incubated at 37° C. for 1 h to allow HUVECs to attach to the matrigel. Cells are treated with 100 ng/ml VEGF (R&D systems) and control (DMSO) or varying doses of ITZ and Analogue and incubated for 12 h. Phase contrast images of each well (3/well) are taken on an inverted microscope and quantified using Image J software (NIH).

Example 19

Preliminary Testing of Additional Analogues

Additional analogues have been synthesized and characterized in the assays described above.

The data from these compounds demonstrates that modifications to the triazole region of ITZ and PSZ, as well as the side chain region do not affect the ability of the scaffold to inhibit Hh signaling. Each of these compounds demonstrates potent in vitro activity in Hh-dependent mouse embryonic fibroblasts and cultured MB (DAOY) and BCC (ASZ) cell lines.

Example 20

Identification of Key ITZ Features Required for Hh Signaling and Angiogenesis Materials and Methods General Information. Starting materials were purchased from Sigma-Aldrich or Fisher Scientific. ACS grade methanol, ethyl acetate, toluene, anhydrous DMF, NMP, and DMSO were purchased from Fisher Scientific or Sigma-Aldrich. ITZ analogue 9a was purchased from Toronto Research Chemicals. All reactions were run under an argon atmosphere. NMR data was collected on a Bruker AVANCE 500 MHz spectrometer and analysis performed using MestReNova. HRMS data was analyzed at the Mass Spectrometry Facility at the University of Connecticut by Dr. You-Jun Fu. FT-IR analysis was performed on a Bruker Alpha Platinum ATR instrument using OPUS software (v 7.2). The preparation of previously characterized ITZ intermediates followed known procedures with minor modifications. X-ray crystals were prepared using vapor diffusion

| Name | Structure | $IC_{50}$ ($\mu$M) Gli1-C3Hs | $IC_{50}$ ($\mu$M) Ptch1-C3Hs | $IC_{50}$ ($\mu$M) Gli1-DAOYs | $IC_{50}$ ($\mu$M) Gli1-ASZs | $IC_{50}$ ($\mu$M) Gli1-M2s |
|---|---|---|---|---|---|---|
| ITZ | [structure] | 0.07 ± 0.02 | 0.20, 0.33 | 0.6 ± 0.08 | 0.14 ± 0.02 | 0.30, 0.52 |
| PSZ | [structure] | 0.01 ± 0.005 | ND | 0.89 ± 0.1 | 0.54 ± 0.05 | ND |
| Amd5-54 (Analogue 1) | [structure] | 0.14 ± 0.04 | ND | ND | 0.17 ± 0.04 | ND |
| Itz-psz #1 (S-) | [structure] | 0.45 ± 0.09 | ND | ND | 0.15 ± 0.01 | ND |
| Itz-psz #2 (R-) | [structure] | 0.18 ± 0.02 | ND | ND | 0.10 ± 0.01 | ND | techniques (pentanes:chloroform) and analysis performed by Dr. Victor Day at the Small-Molecule X-ray Crystallography Lab at the University of Kansas on a Bruker MicroStar microfocus Cu rotating anode generator with two CCD detectors or a Bruker Apex II CCD detector equipped with Helios multilayer optics instruments. Mercury (v3.0) software was used to visualize X-ray structural analysis. All ITZ analogues evaluated in the biological assays (1a-25a) were greater than 95% pure based on the HPLC methods described below.

Purity Analysis of Final Analogues. It is important to note that final ITZ analogues 1a-11a were synthesized and evaluated as stereoisomeric mixtures. For this initial series, we did not separate individual stereoisomers nor did we determine the ratios of cis:trans dioxolanes produced in the ketalization reaction. These mixtures are reflected in the $^1$H and $^{13}$C NMR characterization data described below. Purity analysis for all final analogues was determined via one of the methods described below.

Method A. ITZ analogues were dissolved in HPLC grade MeCN and injected (20 µl of a 1 mM soln) into an Agilent Manual FL-Injection Valve (600 bar) on an Agilent 1100/1200 Series HPLC equipped with an Agilent Eclipse Plus C18 (4.6×100 mm) column and Agilent 1100 Series Photodiode Array Detector. The mobile phase consisted of 60% MeCN:40% $H_2O$ for analogues containing the triazole moiety and 70% MeCN:30% $H_2O$ for des-triazole analogues. All analogues were run at a flow rate of 1.0 mL/min for 20 mins and purity was assessed at 254 nm.

Method B. ITZ analogues were dissolved in HPLC grade MeCN and injected (20 µl of a 1 mM soln) into an Agilent HPLC system coupled to an Agilent ESI single quadrupole mass spectrometer equipped with a Kinetix C18 (150×4.6 mm) column and an Agilent G1315 diode array detector. The mobile phase consisted of 70% MeCN:30% $H_2O$. All analogues were run at a flow rate of 0.7 mL/min for 30 mins and purity was assessed at 254 nm.

Previously Characterized ITZ Intermediates. Common ITZ linker region (28a-32a and 68a), dioxolane region (53a-56a, 59a, 62a-63a), side chain (35a-36a), and coupled intermediates were prepared primarily as described previously for the ITZ scaffold with the minor modifications. Procedures and characterization for newly reported key intermediates and all final analogues is provided below.

First Generation ITZ Intermediates and Final Analogues (1a-11a).

1-(1H-1,2,4-triazol-1-yl)propan-2-one (51a). A solution of chloroacetone (47a) (1.72 mL, 21.6 mmol), 1H-1,2,4-triazole (50a) (2.98 g, 43.2 mmol), NaHCO$_3$ (2.89 g, 34.5 mmol), and toluene (100 mL) were heated to reflux (110-120° C.) for 3 h. The reaction vessel was cooled to −20° C. for 12 h. The resulting precipitate was filtered, dissolved in H$_2$O, and extracted with EtOAc (50 mL×3). The organic layer was collected, washed with saturated sodium chloride (100 mL), and dried (Na$_2$SO$_4$). The solvent was evaporated and the crude product was purified via column chromatography (SiO$_2$, 0-3% MeOH in DCM) resulting in a yellow oil (600 mg, 22.2%). $^1$H NMR (500 MHz, CDCl$_3$) δ 8.01 (s, 1H), 7.76 (s, 1H), 4.90 (s, 2H), 2.00 (s, 3H). $^{13}$C NMR (126 MHz, CDCl$_3$) δ 199.58, 151.41, 144.15, 57.52, 26.63. DART-HRMS: m/z calcd. for C$_5$H$_7$N$_3$O [MH]$^+$, 126.0667. Found: 126.0691. IR (solid) vmax: 3122, 2935, 2241, 1728, 1507, 1352, 1273, 1137, 1115, 727, 677, 646.

1-phenyl-2-(1H-1,2,4-triazol-1-yl)ethanone (52a). A solution of 2-bromoacetophenone (48) (2.0 g, 10.0 mmol), 1H-1,2,4-triazole (50a) (1.4 g, 20.1 mmol), NaHCO$_3$ (1.3 g, 16.1 mmol), and toluene (100 mL) were heated to reflux (110-120° C.) for 3 h. The reaction vessel was cooled to −20° C. for 12 h. The resulting precipitate was filtered, dissolved in H$_2$O, and extracted with EtOAc (3×50 mL). The organic layer was collected, washed with saturated sodium chloride, and dried over sodium sulfate. The solvent was evaporated and the crude product was purified via column chromatography (SiO$_2$, 0-3% MeOH in DCM) resulting in a yellow solid (1.2 g, 64.1%). $^1$H NMR (500 MHz, CDCl$_3$) δ 8.28 (s, 1H), 8.04 (s, 3H), 7.70 (s, 1H), 7.57 (s, 2H), 5.71 (s, 2H). $^{13}$C NMR (126 MHz, CDCl$_3$) δ 190.84, 152.02, 145.07, 134.69, 129.30, 128.25, 55.19. DART-HRMS: m/z calcd. for C$_{10}$H$_9$N$_3$O [MH]$^+$, 188.0824. Found: 188.0822. IR (solid) vmax: 3113, 3062, 2992, 2953, 1697, 1596, 1504, 1450, 1345, 1225, 1207, 1135, 1021, 888, 752, 687, 675, 656, 634.

(2-((1H-1,2,4-triazol-1-yl) methyl)-2-methyl-1,3-dioxolan-4-yl) methyl 4-methylbenzenesulfonate (57a). Ketone 51a (1.4 g, 11.9 mmol) and 56a (2.8 g, 11.5 mmol) were added to a dry round bottom flask. Anhydrous toluene (10 mL) was added and the mixture was cooled to 0° C. at which time TfOH (4.0 mL, 45.9 mmol) was added dropwise with a glass syringe. The solution was stirred at RT for 60 h. The mixture was diluted with 50 mL of EtOAc and slowly added to a solution of K$_2$CO$_3$ (5 g) in water (40 mL). The aqueous layer was washed with EtOAc (3×50 mL) and the organic layers were combined, dried (Na$_2$SO$_4$), filtered, and concentrated. The crude product was purified via column chromatography (SiO$_2$, 0-10% MeOH in DCM) (200 mg, <10%). $^1$H NMR (500 MHz, CDCl$_3$) δ 8.10 (d, J=8.3 Hz, 1H), 7.86 (s, 1H), 7.81-7.75 (m, 2H), 7.37 (m, 2H), 4.39-4.24 (m, 3H), 4.06 (m, 1H), 4.03-3.92 (m, 1H), 3.86 (m, 1H), 3.83-3.74 (m, 1H), 3.69 (m, 1H), 3.53 (m, 1H), 2.46 (d, J=5.7 Hz, 3H), 1.32 (d, J=5.9 Hz, 3H). $^{13}$C NMR (126 MHz, CDCL$^3$) δ 152.04, 151.89, 145.75, 144.96, 132.89, 130.45, 130.39, 128.40, 74.56, 74.07, 68.83, 68.68, 67.17, 67.03, 55.93, 55.88, 23.77, 22.66, 22.09. DART-HRMS: m/z calcd. for C$_{15}$H$_{19}$N$_3$O$_5$S [MH]$^+$, 354.1124. Found: 354.1124. IR (solid) vmax: 3007, 2989, 2916, 2894, 1594, 1557, 1359, 1172, 1093, 1035, 961, 873, 724, 662, 563.

(2-((1H-1,2,4-triazol-1-yl)methyl)-2-phenyl-1,3-dioxolan-4-yl)methyl 4-methylbenzenesulfonate (58a). Crude dioxolane 58a was prepared through a procedure analogous to that described above for 57a. Following extraction with EtOAc, the combined organic layers were dried (Na$_2$SO$_4$), filtered, and concentrated to ~70 mL EtOAc. A solution of TsOH monohydrate (2.0 g) in EtOAc (13 mL) was slowly added at RT. The product precipitated as a salt and was filtered (3.9 g). The salt was dissolved in aqueous saturated K$_2$CO$_3$ (100 mL) and washed with DCM (3×100 mL). The organic layers were combined, dried (Na$_2$SO$_4$) and used without further purification (62%). $^1$H NMR (500 MHz, CDCl$_3$) δ 8.02 (s, 1H), 7.77-7.70 (m, 3H), 7.40-7.27 (m, 8H), 4.42 (d, J=1.4 Hz, 2H), 4.22-4.13 (m, 1H), 3.75 (m, 2H), 3.61 (m, 1H), 3.47 (m, 1H), 2.42 (s, 3H). $^{13}$C NMR (126 MHz, CDCl$_3$) δ 151.12, 145.23, 138.05, 132.33, 129.98, 129.27, 128.62, 127.94, 125.64, 108.44, 73.42, 68.52, 66.55, 55.71, 21.65. DART-HRMS: m/z calcd. for C$_{20}$H$_{21}$N$_3$O$_5$S [MH]$^+$, 416.1280. Found: 416.1263. IR (solid) vmax: 3311, 3111, 2992, 2953, 2893, 1596, 1509, 1448, 1349, 1336, 1232, 1172, 1043, 968, 811, 736, 699, 611, 551.

(2-(2,4-dichlorophenyl)-2-methyl-1,3-dioxolan-4-yl) methyl 4-methylbenzenesulfonate (61a). To a solution of 2',4'-dichloroacetophenone (60a) (20 g, 0.1 mol) in toluene (80 mL) was added glycerol (11 g, 0.12 mol) followed by a catalytic amount of p-toluenesulfonic acid monohydrate (475 mg, 2.5 mmol). A Dean-Stark trap (10 mL trap filled with 8 mL toluene) and condenser were fitted atop the reaction flask. The solution was refluxed for 48 h. Upon cooling, the mixture was diluted with EtOAc and washed sequentially with saturated sodium bicarbonate (3×100 mL), water (2×100 mL), and saturated sodium chloride (100 mL). The organic layer was dried (MgSO$_4$), filtered, concentrated, and purified by column chromatography (SiO$_2$, 3:1 Hex: EtOAc) to yield 61a as a clear oil in excellent yield (88%). $^1$H NMR (500 MHz, CDCl$_3$) δ 7.78 (d, J=8.2 Hz, 1H), 7.47 (m, 1H), 7.36-7.31 (m, 2H), 7.31-7.27 (m, 1H), 7.18-7.14 (m, 1H), 4.16 (m, 1H), 4.10-4.00 (m, 2H), 3.89-3.77 (m, 1H), 3.68 (m, 1H), 2.43 (s, 1H), 2.42 (s, 2H), 1.66 (d, J=1.0 Hz, 3H). $^{13}$C NMR (126 MHz, CDCl$_3$) δ 144.98, 13 7.50, 134.44, 132.50, 130.95, 130.69, 129.80, 129.74, 128.58, 128.11, 127.81, 127.71, 126.64, 126.56, 109.26, 109.23, 73.62, 72.69, 69.32, 68.53, 66.32, 65.98, 25.46, 25.38, 21.48. DART-HRMS: m/z calcd. for C$_{18}$H$_{18}$Cl$_2$O$_5$S [MH]$^+$, 417.0330. Found: 417.0306. IR (solid) vmax: 2988, 2941, 2889, 1586, 1556, 1464, 1364, 1188, 1174, 1095, 1035, 979, 809, 662, 552.

4-(4-(4-(4-((2-((1H-1,2,4-triazol-1-yl)methyl)-2-(2,4-dichlorophenyl)-1,3-dioxolan-4-yl)methoxy)phenyl)piperazin-1-yl)phenyl)-2-(sec-butyl)-2,4-dihydro-3H-1,2,4-triazol-3-one (1a). To a solution of 45a (50 mg, 0.127 mol) in DMSO (2 mL) was added dioxolane tosylate 59a (67 mg, 0.139 mmol) followed by Cs$_2$CO$_3$ (0.41 mg, 1.27 mmol). The mixture was warmed to 80° C. and stirred for 16 h. The mixture was cooled to RT and water was added slowly (6 mL) with vigorous stirring to form a precipitate. The precipitate was filtered, washed with water, and determined to be the product with only DMOS as an impurity. The precipitate was dissolve in EtOAc (60 mL) and washed with water (50 mL). The aqueous layer was washed with EtOAc (1×50 mL) and the combined organic layers were dried (Na$_2$SO$_4$), filtered, and concentrated. The crude residue was purified by column chromatography (SiO$_2$, 0-80% acetone in hexanes) and sonicated in pentanes to produce 1a as a white solid (62 mg, 69%). $^1$H NMR (500 MHz, CDCl$_3$) δ 8.20 (d, J=8.2 Hz, 1H), 7.91 (d, J=10.6 Hz, 1H), 7.64-7.55 (m, 2H), 7.50-7.39 (m, 3H), 7.06-6.99 (m, 2H), 6.94 (d, J=9.1 Hz, 1H), 6.88 (d, J=8.9 Hz, 1H), 6.84-6.77 (m, 1H), 6.69-6.61 (m, 1H), 4.88-4.70 (m, 2H), 4.40-4.19 (m, 2H), 3.96-3.87 (m, 1H), 3.85-3.76 (m, 2H), 3.54-3.44 (m, 1H), 3.36 (m, 4H), 3.23 (m, 4H), 1.87 (m, 1H), 1.72 (m, 1H), 1.39 (dd, J=6.7, 1.4 Hz, 3H), 0.91 (m, 3H). $^{13}$C NMR (126 MHz, CDCl$_3$) δ 152.52, 152.43, 151.94, 151.49, 151.31, 150.45, 145.94, 145.89, 144.81, 144.60, 135.98, 135.70, 134.97, 133.97, 133.81, 133.04, 132.89, 131.35, 131.06, 129.52, 129.42, 127.15, 126.98, 125.87, 123.46, 118.37, 118.27, 116.58, 115.19, 115.08, 74.62, 67.57, 67.37, 54.30, 53.53, 52.58, 50.49, 49.15, 28.35, 19.17, 10.70. DART-HRMS: m/z calcd. for C$_{35}$H$_{38}$Cl$_2$N$_8$O$_4$ [MH]$^+$, 705.2471. Found: 705.2474. IR (solid) vmax: 3125, 2966, 2832, 1698, 1585, 1551, 1510, 1450, 1379, 1228, 1184, 1139, 1042, 976, 944, 824, 736. Purity: 98.0% (Method A).

1-(sec-butyl)-4-(4-(4-(4-((2-(2,4-dichlorophenyl)-2-methyl-1,3-dioxolan-4-yl)methoxy)phenyl)piperazin-1-yl)phenyl)-1H-1,2,4-triazol-5(4H)-one (2a). To a solution of 45a (64 mg, 0.163 mmol) in DMSO (10 mL) was added sodium hydride (1.14 mmol). The mixture was warmed to 50° C. and stirred for 2 h. To this solution was added 61a (62 mg, 0.148 mmol in DMSO, 5 mL). The solution was warmed to 90° C. and stirred for 12 h. The mixture was cooled to RT and H$_2$O (30 mL) was added slowly with vigorous stirring. The mixture was washed with EtOAc (3×100 mL), and the organic layers were combined, dried (Na$_2$SO$_4$), filtered, and concentrated. The crude residue was purified by column chromatography (SiO$_2$, 0-5% MeOH in DCM) to afford 2a as a reddish-brown solid in modest yield (34%). A portion of 2a was dissolved in chloroform and slow evaporation provided off-white crystals that were utilized for the biological assays. $^1$H NMR (500 MHz, CDCl$_3$) δ 7.66-7.59 (m, 2H), 7.46-7.36 (m, 3H), 7.21 (m, 1H), 7.06-7.00 (m, 2H), 7.01-6.71 (m, 4H), 4.37-4.25 (m, 2H), 4.12 (m, 1H), 4.01 (m, 1H), 3.96 (m, 1H), 3.79 (m, 1H), 3.36 (d, J=6.2 Hz, 4H), 3.31-3.17 (m, 4H), 1.89-1.82 (m, 1H), 1.82 (s, 3H), 1.78 (s, 1H), 1.72 (m, 1H), 1.39 (d, J=6.7 Hz, 3H), 0.90 (t, J=7.4 Hz, 3H). $^{13}$C NMR (126 MHz, CDCl$_3$) δ 152.0, 150.5, 138.1, 134.5, 133.8, 132.8, 131.1, 128.8, 128.5, 126.7, 126.6, 125.9, 123.5, 118.4, 116.6, 115.5, 109.0, 73.9, 69.2, 66.9, 52.7, 50.6, 49.2, 28.4, 25.8, 25.7, 19.2, 10.7. DART-HRMS: m/z calcd. for C$_{33}$H$_{38}$Cl$_2$N$_5$O$_4$ [MH]$^+$, 638.2301. Found: 638.2298. IR (solid) vmax 2960, 2922, 2874, 2850, 1696, 1552, 1509, 1462, 1449, 1376, 1226, 1192, 1149, 1076, 1034, 870, 734. Purity: 98.0% (Method A).

4-(4-(4-(4-((2-((1H-1,2,4-triazol-1-yl)methyl)-2-phenyl-1,3-dioxolan-4-yl)methoxy)phenyl)piperazin-1-yl)phenyl)-1-(sec-butyl)-1H-1,2,4-triazol-5(4H)-one (3a). ITZ analogue 3a was prepared using the general method described above for analogue 1a utilizing the requisite linker/side chain and dioxolane intermediates (23 mg, 47%). $^1$H NMR (500 MHz, CDCl$_3$) δ 8.20 (s, 1H), 7.91 (s, 1H), 7.61 (s, 1H), 7.57-7.51 (m, 2H), 7.46-7.34 (m, 5H), 7.06-7.00 (m, 2H), 6.96-6.90 (m, 2H), 6.82-6.76 (m, 2H), 4.54 (d, J=1.6 Hz, 2H), 4.39-4.25 (m, 2H), 3.90 (dd, J=8.4, 6.7 Hz, 1H), 3.77 (m, 2H), 3.44 (m, 1H), 3.39-3.33 (m, 4H), 3.26-3.16 (m, 4H), 1.93-1.80 (m, 1H), 1.78-1.65 (m, 1H), 1.39 (d, J=6.8 Hz, 3H), 0.90 (t, J=7.4 Hz, 3H). $^{13}$C NMR (126 MHz, CDCl$_3$) δ 152.45, 151.61, 145.20, 139.21, 134.33, 129.63, 129.08, 126.23, 123.97, 118.89, 117.09, 115.69, 74.96, 68.39, 67.73, 56.33, 53.09, 51.03, 49.65, 28.86, 19.67, 11.21. DART-HRMS: m/z calcd. for C$_{35}$H$_{40}$N$_8$O$_4$ [MH]$^+$, 637.3251. Found: 637.3271. IR (solid) vmax 3122, 3058, 2961, 2825, 1693, 1602, 1551, 1508, 1448, 1388, 1327, 1296, 1226, 1180, 1135, 1939, 944, 823, 736, 701, 676. Purity: 97.1% (Method A).

4-(4-(4-(4-((2-((1H-1,2,4-triazol-1-yl)methyl)-2-methyl-1,3-dioxolan-4-yl)methoxy)phenyl)piperazin-1-yl)phenyl)-2-(sec-butyl)-2,4-dihydro-3H-1,2,4-triazol-3-one (4a). ITZ analogue 4a was prepared using the general method described above for analogue 1a utilizing the requisite linker/side chain and dioxolane intermediates. (45%) $^1$H NMR (500 MHz, CDCl$_3$) δ 8.30-8.10 (m, 1H), 7.94 (s, 1H), 7.62 (s, 1H), 7.43 (d, J=8.5 Hz, 2H), 7.03 (d, J=8.9 Hz, 2H), 6.97-6.87 (m, 2H), 6.84 (t, J=9.9 Hz, 2H), 4.49 (t, J=5.8 Hz, 1H), 4.39 (s, 1H), 4.36-4.24 (m, 2H), 4.15 (m, 1H), 4.03-3.84 (m, 1H), 3.79 (m, 1H), 3.69-3.59 (m, 1H), 3.42-3.33 (m, 4H), 3.24 (t, J=5.0 Hz, 4H), 1.92-1.81 (m, 1H), 1.72 (m, 1H), 1.44 (s, 1H), 1.43-1.36 (m, 5H), 0.90 (t, J=7.4 Hz, 3H). $^{13}$C NMR (126 MHz, CDCl$_3$) δ 152.7, 152.0, 151.4, 150.5, 145.9, 144.6, 133.9, 125.9, 123.5, 118.5, 118.4, 116.6, 115.3, 115.2, 108.0, 75.4, 74.8, 68.5, 67.7, 67.5, 67.1, 55.7, 55.6, 52.6, 50.6, 49.2, 28.4, 23.5, 22.5, 19.2, 10.7. IR (solid) vmax 3121, 3053, 2930, 2850, 2809, 1702, 1683, 1548, 1510, 1471, 1452, 1336, 1251, 1134, 1106, 1068, 1050, 940, 883, 735. DART-HRMS: m/z calcd. for C$_{30}$H$_{39}$N$_8$O$_4$ [MH]$^+$, 575.3094. Found: 575.3090. IR (solid) vmax: 2967, 2934, 2878, 2837, 1701, 1554, 1510, 1450, 1382, 1225, 1181, 1136, 1042, 1017, 942, 826, 784. Purity: 95.1% (Method A).

1-(sec-butyl)-4-(4-(4-(4-((2,2-dimethyl-1,3-dioxolan-4-yl)methoxy)phenyl)piperazin-1-yl)phenyl)-1H-1,2,4-triazol-5(4H)-one (5a). ITZ analogue 5a was prepared using the general method described above for analogue 2a utilizing the requisite linker/side chain and dioxolane intermediates. The crude residue was purified via column chromatography (SiO$_2$, 0-5% MeOH in DCM) to afford 5a in modest yield (14 mg, 21%) $^1$H NMR (500 MHz, CDCl$_3$) δ 7.61 (d, J=7.2 Hz, 1H), 7.43 (d, J=8.4 Hz, 2H), 7.03 (d, J=8.5 Hz, 2H), 6.94 (s, 1H), 6.89 (d, J=8.4 Hz, 2H), 4.46 (m, 1H), 4.29 (m, 1H), 4.16 (t, J=7.4 Hz, 1H), 4.04 (m, 1H), 3.90 (m, 2H), 3.37 (s, 2H), 3.24 (s, 2H), 1.86 (m, 1H), 1.71 (m, 1H), 1.46 (s, 3H), 1.39 (d, J=7.8 Hz, 6H), 0.91 (t, J=7.4 Hz, 3H). $^{13}$C NMR (126 MHz, CDCl$_3$) δ 152.44, 134.28, 124.08, 123.96, 118.93, 117.14, 115.81, 110.13, 74.49, 69.77, 67.32, 53.11, 51.11, 49.62, 33.08, 28.86, 27.22, 25.79, 19.66, 11.20. DART-HRMS: m/z calcd. for C$_{28}$H$_{37}$N$_5$O$_4$ [MH]$^+$, 508.2924. Found: 508.2909. IR (solid) vmax: 3126, 3060, 2967, 2926, 2878, 2828, 2212, 1681, 1584, 1556, 1510, 1452, 1380, 1226, 1149, 1037, 941, 819, 736. Purity: 97.5% (Method B).

4-(4-(4-(4-((2-((1H-1,2,4-triazol-1-yl)methyl)-2-(2,4-dichlorophenyl)-1,3-dioxolan-4-yl)methoxy)phenyl)piperazin-1-yl)phenyl)-2-((S)-sec-butyl)-2,4-dihydro-3H-1,2,4-triazol-3-one (6a). ITZ analogue 6a was prepared using the general method described above for analogue 1a utilizing the requisite linker/side chain and dioxolane intermediates (55%). $^1$H NMR (500 MHz, CDCl$_3$) δ 8.20 (s, 1H), 7.89 (s, 1H), 7.61 (s, 1H), 7.57 (d, J=8.3 Hz, 1H), 7.47 (d, J=2.1 Hz, 1H), 7.43 (d, J=8.9 Hz, 2H), 7.03 (d, J=9.0 Hz, 2H), 6.94 (m, 2H), 6.80 (m, 2H), 4.80 (m, 2H), 4.36 (m, 1H), 4.28 (m, 1H), 3.92 (m, 1H), 3.81 (m, 2H), 3.48 (m, 1H), 3.36 (m, 4H), 3.23 (m, 4H), 1.86 (m, 1H), 1.72 (m, 1H), 1.39 (d, J=6.7 Hz, 3H), 0.90 (t, J=7.4 Hz, 3H). $^{13}$C NMR (126 MHz, CDCl$_3$) δ 152.6, 151.4, 150.5, 146.0, 144.8, 136.0, 134.0, 133.8, 133.1, 131.4, 129.6, 127.2, 125.9, 123.5, 118.4, 116.6, 115.2, 109.9, 107.6, 74.7, 67.6, 67.4, 53.6, 52.6, 50.5, 49.2, 28.4, 19.2, 10.7. DART-HRMS: m/z calcd. for C$_{35}$H$_{39}$Cl$_2$N$_8$O$_4$ [MH]$^+$, 705.2471. Found: 705.2465. IR (solid) vmax: 2967, 2930, 2878, 1695, 1586, 1552, 1509, 1451, 1378, 1226, 1183, 1130, 1038, 947, 816, 736. Purity: 97.9% (Method A).

4-(4-(4-(4-((2-((1H-1,2,4-triazol-1-yl)methyl)-2-(2,4-dichlorophenyl)-1,3-dioxolan-4-yl)methoxy)phenyl)piperazin-1-yl)phenyl)-2-((R)-sec-butyl)-2,4-dihydro-3H-1,2,4-triazol-3-one (7a). ITZ analogue 7a was prepared using the general method described above for analogue 1a utilizing the requisite linker/side chain and dioxolane intermediates (77%). $^1$H NMR (500 MHz, CDCl$_3$) δ 8.20 (s, 1H), 7.89 (s, 1H), 7.64-7.54 (m, 2H), 7.50-7.40 (m, 3H), 7.03 (d, J=8.6 Hz, 2H), 6.95 (s, 1H), 6.81 (d, J=8.4 Hz, 2H), 4.84 (d, J=14.7 Hz, 1H), 4.76 (d, J=14.7 Hz, 1H), 4.39-4.25 (m, 2H), 3.92 (m, 1H), 3.86-3.77 (m, 2H), 3.50 (m, 1H), 3.38 (s, 2H), 3.25 (s, 3H), 1.87 (m, 1H), 1.72 (m, 1H), 1.39 (d, J=6.7 Hz, 3H), 0.91 (t, J=7.4 Hz, 3H). $^{13}$C NMR (126 MHz, CDCl$_3$) δ 152.5, 152.0, 151.3, 150.5, 146.0, 136.0, 134.0, 133.8, 133.1, 131.4, 129.5, 127.2, 125.9, 123.5, 118.4, 116.6, 115.2, 107.6, 77.2, 74.7, 67.6, 67.4, 53.6, 52.6, 50.5, 49.2, 28.4, 19.2, 10.7. DART-HRMS: m/z calcd. for C$_{35}$H$_{39}$Cl$_2$N$_8$O$_4$ [MH]$^+$, 705.2471. Found: 705.2468. IR (solid) vmax: 3067, 2966, 2934, 2878, 2832, 1695, 1585, 1551, 1509, 1450, 1379, 1225, 1180, 1136, 1039, 944, 820, 794. Purity: 95.0% (Method A).

4-(4-(4-(4-((2-((1H-1,2,4-triazol-1-yl)methyl)-2-(2,4-dichlorophenyl)-1,3-dioxolan-4-yl)methoxy)phenyl)piperazin-1-yl)phenyl)-1-propyl-1H-1,2,4-triazol-5(4H)-one (8a). ITZ analogue 8a was prepared using the general method described above for analogue 2a utilizing the requisite linker/side chain and dioxolane intermediates (50 mg, 68%). $^1$H NMR (500 MHz, CDCl$_3$) δ 8.20 (s, 1H), 7.89 (s, 1H), 7.59 (d, J=21.6 Hz, 2H), 7.48 (s, 1H), 7.41 (s, 2H), 7.04 (s, 2H), 6.93 (s, 2H), 6.81 (s, 2H), 4.80 (d, J=23.3 Hz, 2H), 4.36 (s, 1H), 3.92 (s, 1H), 3.82 (s, 4H), 3.52 (s, 1H), 3.37 (s, 4H), 3.24 (s, 5H), 1.84 (s, 2H), 0.98 (s, 3H). $^{13}$C NMR (126 MHz, CDCl$_3$) δ 152.60, 136.48, 134.30, 133.55, 131.85, 130.02, 127.65, 123.98, 117.08, 115.73, 108.05, 75.13, 68.11, 54.05, 51.01, 49.60, 47.62, 22.43, 11.50. DART-HRMS: m/z calcd. for C$_{34}$H$_{36}$Cl$_2$N$_8$O$_4$ [MH]$^+$, 691.2315. Found: 691.2329. IR (solid) vmax: 3068, 2960, 2925, 2873, 2835, 1696, 1585, 1553, 1510, 1452, 1379, 1225, 1160, 1136, 1045, 944, 823, 794. Purity: 95.2% (Method A).

1-(4-((2-((1H-1,2,4-triazol-1-yl)methyl)-2-(2,4-dichlorophenyl)-1,3-dioxolan-4-yl)methoxy)phenyl)-4-(4-nitrophenyl)piperazine (10a). To a solution of 68a (100 mg, 0.336 mmol) in DMSO (4 mL) was added Cs$_2$CO$_3$ (1.1 g, 3.36 mmol) and 59a (0.29 g, 0.604 mmol). The solution was warmed to 90° C. and stirred for 12 h. The mixture was cooled to room temperature and water was added slowly with vigorous stirring (~6 mL). A yellow precipitate formed, which was filtered and recrystallized in EtOH to yield 10a (150 mg, 73%). a$^1$H NMR (500 MHz, CDCl$_3$) δ 8.22-8.12 (m, 3H), 7.90 (s, 1H), 7.58 (d, J=8.5 Hz, 1H), 7.48 (d, J=2.1 Hz, 1H), 6.95-6.86 (m, 4H), 6.86-6.78 (m, 2H), 4.84 (d, J=14.8 Hz, 1H), 4.76 (d, J=14.7 Hz, 1H), 4.36 (m, 1H), 3.92 (m, 1H), 3.85-3.75 (m, 3H), 3.61-3.55 (m, 4H), 3.48 (m, 1H), 3.26-3.20 (m, 4H). $^{13}$C NMR (126 MHz, CDCl$_3$) δ 154.79, 152.90, 151.42, 145.67, 144.94, 138.79, 136.14, 134.08, 133.17, 131.49, 129.63, 127.28, 125.99, 118.58, 115.39, 112.90, 107.69, 74.72, 67.71, 67.45, 53.63, 50.33, 47.29. DART-HRMS: m/z calcd. for C$_{29}$H$_{28}$Cl$_2$N$_6$O$_5$ [MH]$^+$, 611.1577. Found: 611.1601. IR (solid) vmax: 3116, 2923, 2852, 1589, 1557, 1506, 1456, 1377, 1318, 1226, 1136, 1029, 975, 942, 896, 823, 737, 691. Purity: 95.0% (Method A).

4-(4-(4-((2-((1H-1,2,4-triazol-1-yl)methyl)-2-(2,4-dichlorophenyl)-1,3-dioxolan-4-yl)methoxy)phenyl)piperazin-1-yl)aniline (11a). 10% palladium on carbon (1.04 mg, 5% mole ratio) was added to a dry round bottom flask. Ethanol (25 mL) was added followed by slow addition of 10a (120 mg, 0.196 mmol). Hydrazine monohydrate (0.06 mL, 1.96 mmol) was added dropwise and the mixture was stirred at reflux for 2 h. Upon cooling to RT, the mixture was filtered through celite. The celite was washed with ethanol (100 mL) and chloroform (250 mL) to ensure complete elution of the aniline. The filtrate was concentrated to afford a yellow solid, which was recrystallized in EtOH to afford 11a (70 mg, 61%). $^1$H NMR (500 MHz, CDCl$_3$) δ 8.20 (s, 1H), 8.15 (d, J=9.4 Hz, 2H), 7.89 (s, 1H), 7.57 (d, J=8.4 Hz, 1H), 7.47 (m, 1H), 7.25 (m, 1H), 6.92 (m, 2H), 6.88 (d, J=9.5 Hz, 2H), 6.80 (d, J=9.0 Hz, 2H), 4.80 (m, 2H), 4.36 (m, 1H), 3.91 (m, 1H), 3.80 (m, 2H), 3.58 (m, 4H), 3.47 (m, 1H), 3.22 (m, 4H). $^{13}$C NMR (126 MHz,) δ 154.7, 152.8, 151.3, 145.6, 144.9, 138.7, 136.1, 134.0, 133.1, 131.4, 129.6, 127.2, 125.9, 118.5, 115.3, 112.8, 107.6, 74.6, 67.6, 67.4, 53.6, 50.3, 47.2. DART-HRMS: m/z calcd. for C$_{29}$H$_{31}$Cl$_2$N$_6$O$_3$ [MH]$^+$, 581.1835. Found: 581.1818. IR (solid) vmax: 3084, 2886, 2827, 1558, 1504, 1313, 1224, 113, 1030, 942, 821, 749. Purity: 96.1% (Method A).

Second Generation ITZ Intermediates and Final Analogues (12a-25a).

(2-(2,4-dichlorophenyl)-2-methyl-1,3-dioxolan-4-yl)methyl 4-methylbenzenesulfonate (61a') and (2-(2,4-dichlorophenyl)-2-methyl-1,3-dioxolan-4-yl)methyl 4-methylbenzenesulfonate (61a"). The defined trans (61a') and cis (61a") mixtures of des-triazole dioxolane tosylates were prepared by extensive column chromatography (SiO$_2$, 0-20% EtOAc in Hex) on the complete mixture of tosylate stereoisomers 61a. Fraction 1 (R$_f$~0.7 in 3:1 Hex:EtOAc) was characterized as 2,4-anti-substituted dioxolanes (61a') and Fraction 2

($R_f$~0.6 in 3:1 Hex:EtOAc) was characterized as the 2,4-syn-substituted dioxolanes (61a") [Combined yield=90%; Fraction 1 (61a')=60%; Fraction 2 (61a")=35%]. Fraction 1 crystallized over time whereas Fraction 2 remained a clear oil.

61a'. $^1$H NMR (500 MHz, CDCl$_3$) δ 7.82 (d, J=8.2 Hz, 2H), 7.49 (d, J=8.3 Hz, 1H), 7.39-7.32 (m, 3H), 7.20 (m, 1H), 4.21-4.14 (m, 1H), 4.10 (m, 1H), 4.03 (m, 1H), 3.87 (m, 1H), 3.72 (m, 1H), 2.46 (s, 3H), 1.70 (s, 3H). $^{13}$C NMR (126 MHz, CDCl$_3$) δ 145.11, 137.59, 134.67, 132.69, 132.66, 131.17, 129.92, 128.67, 128.00, 126.78, 109.43, 72.80, 69.36, 66.22, 25.55, 21.65. DART-HRMS: m/z calcd. for $C_{18}H_{18}Cl_2O_5S$ [MH]$^+$, 417.0330. Found: 417.0345. IR (solid) vmax: 3007, 2989, 2937, 2894, 1585, 1557, 1465, 1359, 1186, 1172, 1093, 1036, 811, 751, 663, 552, 492.

61a". $^1$H NMR (500 MHz, CDCl$_3$) δ 7.76-7.61 (m, 2H), 7.46 (d, J=8.5 Hz, 1H), 7.36-7.29 (m, 3H), 7.11 (m, 1H), 4.52-4.38 (m, 1H), 4.20 (m, 1H), 3.92 (m, 1H), 3.80 (m, 1H), 3.57 (m, 1H), 2.47 (s, 3H), 1.70 (d, J=1.1 Hz, 3H). $^{13}$C NMR (126 MHz, CDCl$_3$) δ 145.10, 138.65, 134.45, 132.59, 132.38, 130.92, 129.87, 128.21, 127.90, 126.72, 109.48, 73.73, 68.57, 66.60, 25.63, 21.67. DART-HRMS: m/z calcd. for $C_{18}H_{18}Cl_2O_5S$ [MH]$^+$, 417.0330. Found: 417.0347. IR (solid) vmax: 2988, 2939, 2888, 1586, 1556, 1464, 1364, 1188, 1174, 1095, 1034, 979, 808, 662, 522.

((2R,4S)-2-(2,4-dichlorophenyl)-2-methyl-1,3-dioxolan-4-yl)methyl 4-methylbenzenesulfonate (64) and (2S,4S)-2-(2,4-dichlorophenyl)-2-methyl-1,3-dioxolan-4-yl)methyl 4-methylbenzenesulfonate (65a). Stereochemically-defined tosylated des-triazole intermediates 64a and 65a were prepared from 60a and tosylated glycerol 62a using the general method described above for 61a. Following initial column chromatography, ~740 mg of the 64a:65a mixture was loaded on a preparative TLC plate (Analtech Uniplate, 20×20 cm, 2000 mm coating thickness, Silica G). The plate was developed repeatedly (8× in 8:1 Hex:EtOAc). Following development and separation, the two bands were stripped from the TLC plate and the compounds removed from the silica beads by gentle stirring (5% MeOH in DCM, 200 mL, 12 h).

(64a). White solid, 45%. $R_f$=0.7 in 3:1 Hex:EtOAc. $^1$H NMR (500 MHz, CHCl$_3$) 7.78 (m, 3H), 7.48 (d, J=8.4 Hz, 1H), 7.34 (m, 3H), 7.17 (m, 1H), 4.18 (m, 1H), 4.08 (m, 1H), 4.02 (m, 1H), 3.84 (m, 1H), 3.69 (m, 1H), 2.43 (s, 3H), 1.67 (s, 3H). $^{13}$C NMR (126 MHz, CDCl$_3$) δ 145.0, 143.7, 138.9, 137.5, 134.5, 132.5, 132.5, 131.0, 129.8, 129.7, 129.7, 128.6, 127.8, 127.3, 126.6, 109.2, 72.7, 69.3, 66.0, 25.4, 21.5, 21.3. DART-HRMS: m/z calcd. for $C_{18}H_{18}Cl_2O_5S$ [MH]$^+$, 417.0330. Found: 417.0327. IR (solid) vmax: 3093, 3007, 2989, 2916, 2894, 1585, 1556, 1359, 1186, 1172, 1093, 1035, 960, 940, 861, 751, 662, 551, 492.

(65a). Clear oil, 25%. $R_f$=0.6 in 3:1 Hex:EtOAc. $^1$H NMR (500 MHz, CHCl$_3$) 7.69 (d, J=8.2 Hz, 2H), 7.46 (d, J=8.4 Hz, 1H), 7.31 (m, 3H), 7.10 (m, 1H), 4.44 (m, 1H), 4.19 (m, 1H), 3.91 (m, 1H), 3.80 (m, 1H), 3.56 (m, 1H), 2.46 (s, 3H), 1.70 (s, 3H). $^{13}$C NMR (126 MHz, CDCl$_3$) δ 145.0, 138.6, 134.4, 132.5, 132.3, 130.9, 129.8, 128.2, 127.8, 126.7, 109.4, 73.7, 68.5, 66.5, 29.6, 25.6, 21.6. DART-HRMS: m/z calcd. for $C_{18}H_{18}Cl_2O_5S$ [MH]$^+$, 417.0330. Found: 417.0325. IR (solid) vmax: 3117, 3054, 2955, 2822, 1687, 1551, 1353, 1229, 1187, 1173, 1095, 1033, 967, 943, 824, 809, 663, 552, 531.

((2S,4R)-2-(2,4-dichlorophenyl)-2-methyl-1,3-dioxolan-4-yl)methyl 4-methylbenzenesulfonate (66) and ((2R,4R)-2-(2,4-dichlorophenyl)-2-methyl-1,3-dioxolan-4-yl)methyl 4-methylbenzenesulfonate (67a). Stereochemically-defined tosylated des-triazole intermediates 66a and 67a were prepared from 60a and tosylated glycerol 63a using the general method described above for 61a and purified as described for 64a and 65a.

(66a). Crystalline, 55%. $R_f$=0.6 in 3:1 Hex:EtOAc). $^1$HNMR (500 MHz, CHCl$_3$) 7.81 (m, 3H), 7.49 (d, J=8.4 Hz, 1H), 7.36 (m, 3H), 7.19 (m, 1H), 4.18 (m, 1H), 4.09 (m, 1H), 4.02 (m, 1H), 3.86 (m, 1H), 3.70 (m, 1H), 2.45 (s, 3H), 1.69 (s, 3H). $^{13}$C NMR (126 MHz, CDCl$_3$) δ 145.1, 137.5, 134.6, 132.6, 132.6, 131.1, 129.9, 128.6, 127.9, 127.9, 126.7, 109.4, 72.7, 69.3, 66.1, 25.5, 21.6. DART-HRMS: m/z calcd. for $C_{18}H_{18}Cl_2O_5S$ [MH]$^+$, 417.0330. Found: 417.0358. IR (solid) vmax: 3094, 3008, 2989, 2957, 2936, 2917, 2894, 1593, 1557, 1359, 1186, 1172, 1094, 1036, 961, 940, 862, 752, 662, 552, 493.

(67a). Clear oil, 30%. $R_f$=0.5 in 3:1 Hex:EtOAc. $^1$H NMR (500 MHz, CHCl$_3$) 7.69 (m, 2H), 7.46 (d, J=8.4 Hz, 1H), 7.31 (m, 3H), 7.10 (m, 1H), 4.45 (m, 1H), 4.20 (m, 1H), 3.91 (m, 1H), 3.80 (m, 1H), 3.56 (m, 1H), 2.46 (s, 3H), 1.70 (s, 3H). $^{13}$C NMR (126 MHz, CDCl$_3$) δ 145.1, 138.6, 134.4, 132.5, 132.3, 130.9, 129.8, 128.2, 127.9, 126.7, 109.4, 73.7, 68.5, 66.6, 25.6, 21.6. DART-HRMS: m/z calcd. for $C_{18}H_{18}Cl_2O_5S$ [MH]$^+$, 417.0330. Found: 417.0356. IR (solid) vmax: 3094, 3007, 2989, 2957, 2917, 2894, 1585, 1557, 1358, 1185, 1172, 1093, 1036, 961, 939, 862, 751, 662, 551, 492.

General protocol for tosylate/phenol coupling and final analogue purification. To a solution of alkyl-substituted phenol (43a-46a) (40 mg, 0.102 mmol) in DMSO (2.0 mL) was added des-triazole-tosylate (61a'-61a'", 64a-67a) (46 mg, 0.110 mmol) followed by Cs$_2$CO$_3$ (0.82 mmol). The mixture was warmed to 80° C. and stirred for 16 h. The mixture was then cooled to RT and water was added slowly (6 mL) with vigorous stirring, which resulted in formation of a precipitate. The mixture was transferred to a separatory funnel, diluted with EtOAc (60 mL) and washed with water (50 mL). The aqueous layer was washed with EtOAc (1×60 mL). The organic layers were combined, dried (MgSO$_4$), filtered, and concentrated. The crude residue was purified by column chromatography (SiO$_2$, 0 to 24% acetone in hexanes) to afford 2a, 12a-25a as white to slightly off-white solids in good yields (45-88%). Final analogues were subsequently sonicated in pentanes (10-30 min) to remove a "grease-like" impurity (observed in $^1$H NMRs at 0.88, 1.31 ppm) and collected for purity analysis and biological evaluation following filtration on a fine-fritted glass Buchner style filter funnel.

4-(4-(4-(4-((2-((1H-1,2,4-triazol-1-yl)methyl)-2-(2,4-dichlorophenyl)-1,3-dioxolan-4-yl)methoxy)phenyl)piperazin-1-yl)phenyl)-2-(sec-butyl)-2,4-dihydro-3H-1,2,4-triazol-3-one (12a). $^1$H NMR (500 MHz, CDCl$_3$) δ 7.62 (m, 2H), 7.42 (m, 3H), 7.23 (m, 1H), 7.03 (m, 2H), 6.92 (m, 2H), 4.31 (m, 2H), 4.11 (m, 1H), 4.01 (m, 1H), 3.97 (m, 1H), 3.84 (m, 1H), 3.36 (m, 4H), 3.24 (m, 4H), 1.87 (m, 1H), 1.81 (s, 3H), 1.72 (m, 1H), 1.39 (d, J=6.7 Hz, 3H), 0.91 (t, J=7.4 Hz, 3H). $^{13}$C NMR (126 MHz, CDCl$_3$) δ 152.7, 152.0, 150.5, 145.8, 139.2, 134.2, 133.8, 132.7, 130.9, 128.5, 126.6, 125.9, 123.5, 118.3, 116.6, 115.2, 109.1, 73.9, 69.3, 66.9, 52.6, 50.6, 49.2, 28.4, 25.6, 19.2, 10.7. DART-HRMS: m/z calcd. for $C_{33}H_{38}Cl_2N_5O_4$ [MH]$^+$, 638.2301. Found: 638.2328. IR (solid) vmax 2961, 2918, 2849, 1694, 1584, 1556, 1509, 1449, 1374, 1329, 1294, 1224, 1186, 1149, 1094, 1035, 1017, 942, 873, 821, 802, 734. Purity: 97.0% (Method B).

4-(4-(4-(4-((2-((1H-1,2,4-triazol-1-yl)methyl)-2-(2,4-dichlorophenyl)-1,3-dioxolan-4-yl)methoxy)phenyl)piperazin-1-yl)phenyl)-2-(sec-butyl)-2,4-dihydro-3H-1,2,4-triazol-3-one (13a). $^1$H NMR (500 MHz, CDCl$_3$) δ 7.63 (d, J=8.5 Hz, 1H), 7.61 (s, 1H), 7.42 (m, 2H), 7.38 (d, J=2.1 Hz, 1H), 7.19 (m, 1H), 7.01 (m, 2H), 6.89 (m, 2H), 6.73 (m, 2H), 4.60 (m, 1H), 4.29 (m, 2H), 3.94 (m, 1H), 3.73 (m, 1H), 3.35 (m, 4H), 3.21 (m, 4H), 1.85 (m, 1H), 1.77 (s, 3H), 1.71 (m, 1H), 1.39 (d, J=6.7 Hz, 3H), 0.90 (t, J=7.4 Hz, 3H). $^{13}$C NMR (126 MHz, CDCl$_3$) δ 152.7, 152.0, 150.5, 145.8, 139.2, 134.2, 133.8, 132.7, 130.9, 128.5, 126.6, 125.9, 123.5, 118.3, 116.6, 115.2, 109.1, 75.0, 68.3, 67.3, 52.6, 50.5, 49.2, 28.4, 25.8, 19.2, 10.7. HRMS: m/z calcd. for C$_{33}$H$_{38}$Cl$_2$N$_5$O$_4$ [MH]$^+$, 638.2301. Found: 638.2325. IR (solid) vmax 3102, 3008, 2961, 2918, 2899, 2849, 1699, 1597, 1538, 1515, 1411, 1355, 1337, 1254, 1236, 1189 1159, 1106, 1064, 1036, 1024, 999, 936, 896, 831, 807, 741. Purity: 95.1% (Method B).

2-((S)-sec-butyl)-4-(4-(4-(4-(((2S,4S)-2-(2,4-dichlorophenyl)-2-methyl-1,3-dioxolan-4-yl)methoxy)phenyl)piperazin-1-yl)phenyl)-2,4-dihydro-3H-1,2,4-triazol-3-one (14a). $^1$H NMR (500 MHz, CDCl$_3$) δ 7.61 (m, 3H), 7.42 (m, 2H), 7.40 (m, 1H), 7.23 (m, 1H), 7.02 (m, 2H), 6.94 (m, 2H), 6.88 (m, 2H), 4.31 (m, 2H), 4.11 (m, 1H), 4.00 (m, 1H), 3.96 (m, 1H), 3.36 (m, 4H), 3.23 (m, 4H), 1.85 (m, 1H), 1.81 (s, 3H), 1.72 (m, 1H), 1.39 (d, J=6.7 Hz, 3H), 0.91 (t, J=7.4 Hz, 3H). $^{13}$C NMR (126 MHz, CDCl$_3$) δ 152.9, 152.0, 150.5, 145.9, 138.1, 134.5, 133.8, 132.8, 131.1, 128.8, 126.7, 125.9, 123.5, 118.4, 116.6, 115.4, 109.0, 73.9, 69.2, 66.9, 52.6, 50.6, 49.2, 28.4, 25.7, 19.2, 10.7. DART-HRMS: m/z calcd. for C$_{33}$H$_{38}$Cl$_2$N$_5$O$_4$ [MH]$^+$, 638.2301. Found: 638.2282. IR (solid) vmax 2962, 2875, 2826, 1694, 1555, 1509, 1448, 1374, 1224, 1186, 1149, 1035, 942, 824, 735. Purity: 97.4% (Method A).

2-((S)-sec-butyl)-4-(4-(4-(4-(((2R,4S)-2-(2,4-dichlorophenyl)-2-methyl-1,3-dioxolan-4-yl)methoxy)phenyl)piperazin-1-yl)phenyl)-2,4-dihydro-3H-1,2,4-triazol-3-one (15a). $^1$H NMR (500 MHz, CDCl$_3$) δ 7.64 (d, J=8.4 Hz, 2H), 7.61 (s, 1H), 7.42 (d, J=8.5 Hz, 2H), 7.38 (d, J=2.2 Hz, 2H), 7.19 (m, 1H), 7.02 (d, J=8.5 Hz, 2H), 6.90 (d, J=8.5 Hz, 2H), 6.73 (d, J=8.5 Hz, 2H), 4.60 (m, 1H), 4.30 (m, 2H), 3.94 (m, 1H), 3.73 (m, 2H), 3.35 (m, 4H), 3.21 (m, 4H), 1.86 (m, 1H), 1.78 (s, 3H), 1.72 (m, 1H), 1.39 (d, J=6.7 Hz, 3H), 0.91 (t, J=7.4 Hz, 3H). $^{13}$C NMR (126 MHz, CDCl$_3$) δ 152.8, 152.0, 150.5, 145.8, 139.3, 134.3, 133.8, 132.7, 130.9, 128.5, 126.6, 125.9, 123.5, 118.4, 116.6, 115.2, 109.1, 75.0, 68.4, 67.3, 52.6, 50.6, 49.2, 28.4, 25.8, 19.2, 10.7. DART-HRMS: m/z calcd. for C$_{33}$H$_{38}$Cl$_2$N$_5$O$_4$ [MH]$^+$, 638.2301. Found: 638.2288. IR (solid) vmax 2923, 2851, 1714, 1703, 1683, 1613, 1548, 1509, 1452, 1374, 1271, 1226, 1188, 1150, 1094, 1035, 965, 942, 817, 735. Purity: 95.5% (Method A).

2-((S)-sec-butyl)-4-(4-(4-(4-(((2R,4R)-2-(2,4-dichlorophenyl)-2-methyl-1,3-dioxolan-4-yl)methoxy)phenyl)piperazin-1-yl)phenyl)-2,4-dihydro-3H-1,2,4-triazol-3-one (16a). $^1$H NMR (500 MHz, CDCl$_3$) δ 7.61 (m, 2H), 7.41 (m, 3H), 7.23 (m, 1H), 7.02 (m, 2H), 6.94 (m, 2H), 6.89 (m, 2H), 4.31 (m, 2H), 4.11 (m, 1H), 4.00 (m, 1H), 3.96 (m, 1H), 3.84 (m, 1H), 3.36 (m, 4H), 3.23 (m, 4H), 1.86 (m, 1H), 1.81 (s, 3H), 1.72 (m, 1H), 1.39 (d, J=6.7 Hz, 3H), 0.91 (t, J=7.4 Hz, 3H). $^{13}$C NMR (126 MHz, CDCl$_3$) δ 152.9, 152.0, 150.5, 145.9, 138.1, 134.5, 133.8, 132.8, 131.1, 128.8, 126.7, 125.9, 123.5, 118.4, 116.6, 115.4, 109.0, 73.9, 69.2, 66.9, 52.6, 50.6, 49.2, 28.4, 25.7, 19.2, 10.7. DART-HRMS: m/z calcd. for C$_{33}$H$_{38}$Cl$_2$N$_5$O$_4$ [MH]$^+$, 638.2301. Found: 638.2284. IR (solid) vmax 2966, 2935, 2874, 2824, 1693, 1584, 1555, 1508, 1464, 1447, 1373, 1293, 1223, 1186, 1149, 1095, 1035, 942, 875, 824, 734. Purity: 97.3% (Method A).

2-((S)-sec-butyl)-4-(4-(4-(4-(((2S,4R)-2-(2,4-dichlorophenyl)-2-methyl-1,3-dioxolan-4-yl)methoxy)phenyl)piperazin-1-yl)phenyl)-2,4-dihydro-3H-1,2,4-triazol-3-one (17a). $^1$H NMR (500 MHz, CDCl$_3$) δ 7.64 (d, J=8.5 Hz, 1H), 7.61 (s, 1H), 7.42 (m, 2H), 7.38 (d, J=2.1 Hz, 1H), 7.19 (m, 1H), 7.02 (m, 2H), 6.89 (m, 2H), 6.73 (m, 2H), 4.60 (m, 1H), 4.30 (m, 2H), 3.94 (m, 1H), 3.73 (m, 2H), 3.35 (m, 4H), 3.21 (m, 4H), 1.85 (m, 1H), 1.78 (s, 3H), 1.72 (m, 1H), 1.39 (d, J=6.7 Hz, 3H), 0.91 (t, J=7.4 Hz, 3H). $^{13}$C NMR (126 MHz, CDCl$_3$) δ 152.8, 152.0, 150.5, 145.8, 139.3, 134.3, 133.8, 132.7, 130.9, 128.5, 126.6, 125.9, 123.5, 118.4, 116.6, 115.2, 109.1, 75.0, 68.4, 67.3, 52.6, 50.6, 49.2, 28.4, 25.8, 19.2, 10.7. DART-HRMS: m/z calcd. for C$_{33}$H$_{38}$Cl$_2$N$_5$O$_4$ [MH]$^+$, 638.2301. Found: 638.2281. IR (solid) vmax 2919, 2876, 2849, 1693, 1585, 1555, 1509, 1450, 1375, 1329, 1295, 1225, 1188, 1149, 1095, 1034, 934, 872, 819, 734. Purity: 98.4% (Method A).

2-((R)-sec-butyl)-4-(4-(4-(4-(((2S,4S)-2-(2,4-dichlorophenyl)-2-methyl-1,3-dioxolan-4-yl)methoxy)phenyl)piperazin-1-yl)phenyl)-2,4-dihydro-3H-1,2,4-triazol-3-one (18a). $^1$H NMR (500 MHz, CDCl$_3$) δ 7.61 (m, 2H), 7.42 (m, 2H), 7.41 (m, 1H), 7.23 (m, 1H), 7.03 (m, 2H), 6.94 (m, 2H), 6.89 (m, 2H), 4.31 (m, 2H), 4.11 (m, 1H), 4.01 (m, 1H), 3.96 (m, 1H), 3.84 (m, 1H), 3.36 (m, 4H), 3.23 (m, 4H), 1.87 (m, 1H), 1.81 (s, 3H), 1.72 (m, 1H), 1.39 (d, J=6.7 Hz, 3H), 0.91 (t, J=7.4 Hz, 3H). $^{13}$C NMR (126 MHz, CDCl$_3$) δ 152.9, 152.0, 150.5, 145.9, 138.1, 134.5, 133.8, 132.8, 131.1, 128.8, 126.7, 125.9, 123.5, 118.4, 116.6, 115.4, 109.0, 73.9, 69.2, 66.9, 52.6, 50.6, 49.2, 28.4, 25.7, 19.2, 10.7. DART-HRMS: m/z calcd. for C$_{33}$H$_{38}$Cl$_2$N$_5$O$_4$ [MH]$^+$, 638.2301. Found: 638.2282. IR (solid) vmax 2967, 2932, 2878, 2827, 1695, 1612, 1586, 1552, 1510, 1460, 1377, 1292, 1253, 1225, 1187, 1147, 1096, 1036, 940, 827, 735. Purity: 95.0% (Method B).

2-((R)-sec-butyl)-4-(4-(4-(4-(((2R,4S)-2-(2,4-dichlorophenyl)-2-methyl-1,3-dioxolan-4-yl)methoxy)phenyl)piperazin-1-yl)phenyl)-2,4-dihydro-3H-1,2,4-triazol-3-one (19a). $^1$H NMR (500 MHz, CDCl$_3$) δ 7.64 (d, J=8.5 Hz, 1H), 7.61 (s, 1H), 7.42 (m, 2H), 7.38 (m, 1H), 7.20 (m, 1H), 7.02 (m, 2H), 6.90 (m, 2H), 6.73 (m, 2H), 4.60 (m, 1H), 4.30 (m, 1H), 3.94 (m, 1H), 3.73 (m, 1H), 3.35 (m, 4H), 3.21 (m, 4H), 1.86 (m, 1H), 1.78 (s, 3H), 1.71 (m, 1H), 1.39 (d, J=6.7 Hz, 3H), 0.91 (t, J=7.4 Hz, 3H). $^{13}$C NMR (126 MHz, CDCl$_3$) δ 152.9, 152.0, 150.5, 145.9, 138.1, 134.5, 133.8, 132.8, 131.1, 128.7, 126.7, 125.9, 123.5, 118.4, 116.6, 115.4, 109.0, 73.9, 69.2, 66.9, 52.6, 50.6, 49.2, 28.4, 25.7, 19.2, 10.7. DART-HRMS: m/z calcd. for C$_{33}$H$_{38}$Cl$_2$N$_5$O$_4$ [MH]$^+$, 638.2301. Found: 638.2287. IR (solid) vmax 3060, 2967, 2932, 2830, 1698, 1611, 1586, 1550, 1512, 1461, 1384, 1296, 1252, 1225, 1189, 1149, 1098, 1036, 940, 896, 824, 735. Purity: 95.0% (Method B).

2-((R)-sec-butyl)-4-(4-(4-(4-(((2R,4R)-2-(2,4-dichlorophenyl)-2-methyl-1,3-dioxolan-4-yl)methoxy)phenyl)piperazin-1-yl)phenyl)-2,4-dihydro-3H-1,2,4-triazol-3-one (20a). $^1$H NMR (500 MHz, CDCl$_3$) δ 7.61 (m, 2H), 7.43 (m, 2H), 7.41 (m, 1H), 7.23 (m, 1H), 7.03 (m, 2H), 6.94 (m, 2H), 6.89 (m, 2H), 4.31 (m, 2H), 4.11 (m, 1H), 4.01 (m, 1H), 3.96 (m, 1H), 3.84 (m, 1H), 3.36 (m, 4H), 3.23 (m, 4H), 1.86 (m, 1H), 1.81 (s, 3H), 1.72 (m, 1H), 1.39 (d, J=6.7 Hz, 3H), 0.91 (t, J=7.4 Hz, 3H). $^{13}$C NMR (126 MHz, CDCl$_3$) δ 153.0, 152.0, 150.5, 145.9, 138.1, 134.5, 133.8, 132.8, 131.1, 128.8, 126.7, 125.9, 123.5, 118.4, 116.6, 115.4, 109.0, 73.9, 69.2, 67.0, 52.6, 50.6, 49.2, 28.4, 25.7, 19.2, 10.7. DART-HRMS: m/z calcd. for C$_{33}$H$_{38}$Cl$_2$N$_5$O$_4$ [MH]$^+$, 638.2301. Found: 638.2285. IR (solid) vmax 2971, 2937, 2879, 2827, 1697, 1509, 1451, 1376, 1296, 1225, 1194, 1147, 1073, 1035, 942, 819, 734. Purity: 97.5% (Method B).

2-((R)-sec-butyl)-4-(4-(4-(4-(((2S,4R)-2-(2,4-dichlorophenyl)-2-methyl-1,3-dioxolan-4-yl)methoxy)phenyl)piperazin-1-yl)phenyl)-2,4-dihydro-3H-1,2,4-triazol-3-one (21a). $^1$H NMR (500 MHz, CDCl$_3$) δ 7.64 (d, J=8.5 Hz, 2H), 7.61 (s, 1H), 7.42 (m, 2H), 7.37 (m, 1H), 7.19 (m, 1H), 7.02 (m, 2H), 6.90 (m, 2H), 6.73 (m, 2H), 4.60 (m, 1H), 4.30 (m, 2H), 3.95 (m, 1H), 3.73 (m, 2H), 3.35 (m, 4H), 3.22 (m, 4H), 1.86 (m, 1H), 1.78 (s, 3H), 1.72 (m, 1H), 1.39 (d, J=6.7 Hz, 3H), 0.91 (t, J=7.4 Hz, 3H). $^{13}$C NMR (126 MHz, CDCl$_3$) δ

152.8, 152.0, 150.5, 145.9, 139.3, 134.3, 133.8, 132.7, 130.9, 128.5, 126.6, 125.9, 123.5, 118.4, 116.4, 115.2, 109.1, 75.0, 68.4, 67.3, 52.6, 50.6, 49.2, 28.4, 25.8, 19.2, 10.7. DART-HRMS: m/z calcd. for $C_{33}H_{38}Cl_2N_5O_4$ [MH]+, 638.2301. Found: 638.2284. IR (solid) vmax 2966, 2932, 2904, 2829, 1695, 1553, 1512, 1460, 1444, 1399, 1382, 1254, 1224, 1187, 1148, 1063, 1036, 939, 827, 735. Purity: 96.4% (Method A).

4-(4-(4-(4-(((2R,4R)-2-(2,4-dichlorophenyl)-2-methyl-1,3-dioxolan-4-yl)methoxy)phenyl)piperazin-1-yl)phenyl)-2-propyl-2,4-dihydro-3H-1,2,4-triazol-3-one (22a). $^1$H NMR (500 MHz, CDCl$_3$) δ 7.61 (m, 2H), 7.41 (m, 3H), 7.23 (m, 1H), 7.02 (m, 2H), 6.94 (m, 2H), 6.89 (m, 2H), 4.32 (m, 1H), 4.11 (m, 1H), 4.01 (m, 1H), 3.96 (m, 1H), 3.82 (m, 3H), 3.36 (m, 4H), 3.23 (m, 4H), 1.84 (m, 2H), 1.81 (s, 3H), 0.98 (t, J=7.4 Hz, 3H). $^{13}$C NMR (126 MHz, CDCl$_3$) δ 153.0, 152.1, 150.6, 145.9, 138.1, 134.5, 133.8, 132.8, 131.1, 128.8, 126.7, 125.8, 123.5, 118.4, 116.6, 115.4, 109.0, 73.9, 69.2, 66.9, 50.6, 49.2, 47.2, 25.7, 22.0, 11.1. DART-HRMS: m/z calcd. for $C_{32}H_{36}Cl_2N_5O_4$ [MH]+, 624.2144. Found: 624.2143. IR (solid) vmax 3125, 3059, 2935, 2876, 2829, 1703, 1686, 1614, 1585, 1551, 1510, 1454, 1405, 1375, 1336, 1297, 1225, 1194, 1143, 1094, 1035, 944, 869, 814, 733. Purity: 96.6% (Method B).

4-(4-(4-(4-(((2S,4R)-2-(2,4-dichlorophenyl)-2-methyl-1,3-dioxolan-4-yl)methoxy)phenyl)piperazin-1-yl)phenyl)-2-propyl-2,4-dihydro-3H-1,2,4-triazol-3-one (23a). $^1$H NMR (500 MHz, CDCl$_3$) δ 7.64 (d, J=8.4 Hz, 1H), 7.60 (s, 1H), 7.41 (m, 2H), 7.38 (d, J=2.1 Hz, 1H), 7.20 (m, 1H), 7.02 (d, J=8.9 Hz, 2H), 6.90 (d, J=8.9 Hz, 2H), 6.73 (d, J=8.9 Hz, 2H), 4.64 (m, 1H), 4.30 (m, 1H), 3.94 (m, 1H), 3.82 (t, J=7.2 Hz, 2H), 3.73 (m, 2H), 3.35 (m, 4H), 3.21 (m, 4H), 1.83 (m, 2H), 1.78 (s, 3H), 0.98 (t, J=7.4 Hz, 3H). $^{13}$C NMR (126 MHz, CDCl$_3$) δ 152.8, 152.1, 150.5, 145.8, 139.3, 134.3, 133.8, 132.7, 130.9, 128.5, 126.6, 125.8, 123.5, 118.4, 116.6, 115.2, 109.1, 99.9, 75.0, 68.3, 67.3, 50.6, 49.2, 47.2, 25.8, 22.0, 11.1. HRMS: m/z calcd. for $C_{32}H_{36}Cl_2N_5O_4$ [MH]+, 624.2144. Found: 624.2142. IR (solid) vmax 2966, 2932, 2904, 2830, 1698, 1609, 1585, 1550, 1511, 1461, 1402, 1385, 1336, 1296, 1224, 1189, 1148, 1097, 1036, 940, 875, 824, 735. Purity: 96.5% (Method B).

4-(4-(4-(4-(((2S,4S)-2-(2,4-dichlorophenyl)-2-methyl-1,3-dioxolan-4-yl)methoxy)phenyl)piperazin-1-yl)phenyl)-2-propyl-2,4-dihydro-3H-1,2,4-triazol-3-one (24a). $^1$H NMR (500 MHz, CDCl$_3$) δ 7.64 (d, J=8.4 Hz, 1H), 7.60 (s, 1H), 7.41 (d, J=8.8 Hz, 2H), 7.38 (d, J=2.1 Hz, 1H), 7.02 (m, 2H), 6.90 (d, J=8.5 Hz, 2H), 6.73 (m, 2H), 4.60 (m, 1H), 4.30 (m, 1H), 3.94 (m, 1H), 3.81 (t, J=7.2 Hz, 2H), 3.73 (m, 2H), 3.35 (m, 4H), 3.22 (m, 4H), 1.83 (m, 2H), 1.78 (s, 3H), 0.98 (t, J=7.4 Hz, 3H). $^{13}$C NMR (126 MHz, CDCl$_3$) δ 153.0, 152.1, 150.6, 145.9, 138.1, 134.5, 133.8, 132.8, 131.1, 128.8, 126.7, 125.8, 123.5, 118.4, 116.6, 115.4, 109.0, 73.9, 69.2, 66.9, 50.6, 49.2, 47.2, 25.7, 22.0, 11.1. DART-HRMS: m/z calcd. for $C_{32}H_{36}Cl_2N_5O_4$ [MH]+, 624.2144. Found: 624.2140. IR (solid) vmax 2919, 2876, 2849, 1693, 1601, 1585, 1555, 1509, 1450, 1403, 1375, 1331, 1295, 1225, 1188, 1149, 1095, 1032, 1017, 943, 871, 814, 734. Purity: 95.4% (Method B).

4-(4-(4-(4-(((2R,4S)-2-(2,4-dichlorophenyl)-2-methyl-1,3-dioxolan-4-yl)methoxy)phenyl)piperazin-1-yl)phenyl)-2-propyl-2,4-dihydro-3H-1,2,4-triazol-3-one (25a). $^1$H NMR (500 MHz, CDCl$_3$) δ 7.61 (m, 2H), 7.41 (m, 3H), 7.23 (m, 1H), 7.03 (m, 2H), 6.95 (m, 2H), 6.89 (m, 2H), 4.32 (m, 1H), 4.11 (m, 1H), 4.00 (m, 1H), 3.94 (m, 1H), 3.82 (m, 3H), 3.37 (m, 4H), 3.24 (m, 4H), 1.83 (m, 2H), 1.81 (s, 3H), 0.98 (t, J=7.4 Hz, 3H). $^{13}$C NMR (126 MHz, CDCl$_3$) δ 153.0, 152.1, 150.5, 145.9, 138.0, 134.5, 133.8, 132.7, 131.1, 128.8, 126.7, 125.9, 123.5, 118.4, 116.6, 115.4, 109.0, 73.9, 69.2, 66.9, 50.6, 49.1, 47.2, 25.7, 22.0, 11.0. DART-HRMS: m/z calcd. for $C_{32}H_{36}Cl_2N_5O_4$ [MH]+, 624.2144. Found: 624.2105. IR (solid) vmax 2918, 2876, 2849, 1693, 1585, 1555, 1509, 1464, 1449, 1374, 1330, 1294, 1224, 1187, 1149, 1095, 1035, 964, 942, 872, 817, 734. Purity: 97.8% (Method B).

Biological Assay Protocols.

General Information. Protocols for general cell culture, qPCR and Hh inhibition in C3H10T1/2 and ASZ cells are as previously described.[28] Protocols for the initiation and growth of Math1-Cre-ER; Ptc$^{fl/fl}$ medulloblastoma tumors, isolation and in vitro culture of MERP MB cells, as wells as the anti-proliferation and qPCR studies performed in these cells were as previously described.[a] Sonic Hedgehog (C25II) recombinant mouse protein was purchased from Life Technologies. aData was analyzed using GraphPad Prism 5 and reported values represent mean±SEM for at least two separate experiments performed in triplicate.

HUVEC Cell Viability and Proliferation. HUVEC cell proliferation was assessed by measuring cellular metabolic activity using standard MTS/PMS protocols according to manufacturer's instructions. Briefly, HUVECs (3,000 cells/well) were seeded in a 96-well plate and allowed to attach overnight. Cells were treated with varying concentrations of drug as indicated and proliferation was assessed after 72 h with MTS.

Tube Formation Assay. Matrigel (BD Biosciences) was diluted 1:1 with DMEM (matrigel protein concentration no less than 3 mg/ml) and used to coat the wells of a 24-well tissue culture dish (280 uL per well). Plates were incubated at 37° C. for no more than 1 h until the matrigel solidified. HUVECs were suspended in M199 media with 1% FBS and penicillin/streptomycin and 50,000 cells were added to each well. Plates were incubated at 37° C. for 20-30 min to allow HUVECs to attach to the matrigel. Cells were treated with control (DMSO), known angiogenic inhibitor suramin (10 uM), or varying doses (10, 1, 0.1 μM) of drug and incubated for 16 h. Phase contrast images were taken from multiple locations in each well (8/well) on an inverted microscope and tube formation parameters quantified using Image J software (NIH).

Results

A first generation series of ITZ analogues that systematically truncates the ITZ scaffold from both the left- and right-hand side to identify key structural features required for inhibition of both Hh signaling and angiogenesis (Table 1a) has been prepared.

| Compound | R$_1$ | R$_2$ | R$_3$ |
|---|---|---|---|
| 1a, ITZ | | | |

-continued
| Compound | R₁ | R₂ | R₃ |
|---|---|---|---|
| 2a | —CH₃ | 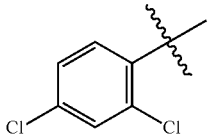 [SMILES: *c1ccc(Cl)cc1Cl] | 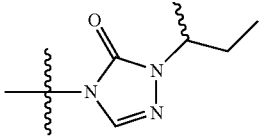 [SMILES: *n1cnn(C(C)CC)c1=O] |
| 3a | 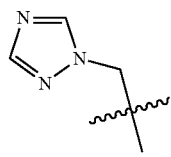 [SMILES: *Cn1cncn1] | 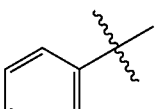 | 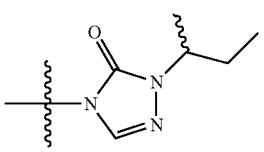 [SMILES: *n1cnn(C(C)CC)c1=O] |
| 4a | 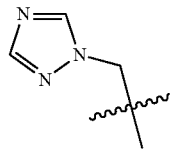 [SMILES: *Cn1cncn1] | —CH₃ | 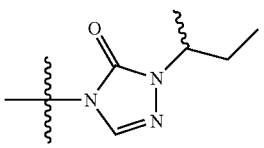 [SMILES: *n1cnn(C(C)CC)c1=O] |
| 5a | —CH₃ | —CH₃ | 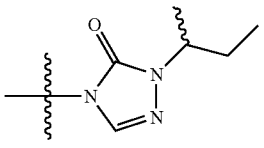 [SMILES: *n1cnn(C(C)CC)c1=O] |
| 6a | 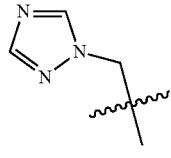 [SMILES: *Cn1cncn1] | 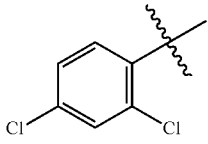 [SMILES: *c1ccc(Cl)cc1Cl] | 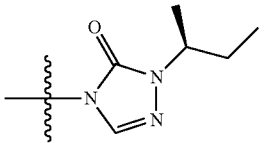 [SMILES: *n1cnn([C@@H](C)CC)c1=O] |
| 7a | 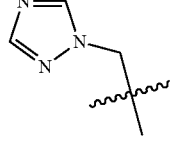 | 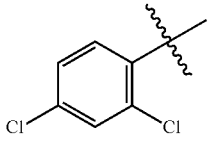 [SMILES: *c1ccc(Cl)cc1Cl] | 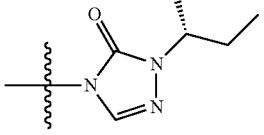 |
| 8a | 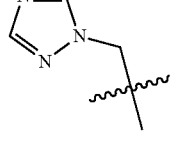 | 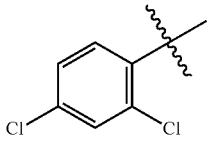 | 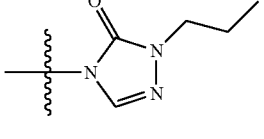 |
| 9a | 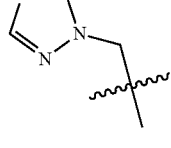 | 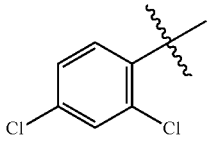 | 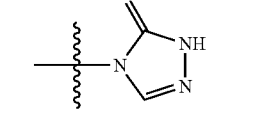 |
| 10a | 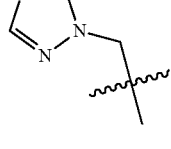 | 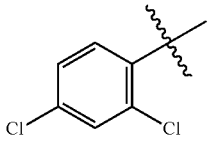 [SMILES: *c1ccc(Cl)cc1Cl] | —NO₂ |

-continued

| Compound | R₁ | R₂ | R₃ |
|---|---|---|---|
| 11a | [1,2,4-triazol-1-ylmethyl group] | [2,4-dichlorophenyl group] | —NH₂ |

Evaluation of this first generation series provided key structure-activity relationship (SAR) data that was subsequently utilized for the design of a second generation of stereo chemically defined ITZ derivatives based on analogue 2a (Table 2). The second generation series was designed to determine whether a specific stereoisomer of key ITZ analogue 2a was responsible for its anti-Hh and/or anti-angiogenic properties.

TABLE 2

Second generation, stereochemically defined analogues of 2.

$$R_1-O-\text{C}_6\text{H}_4-N\underbrace{\phantom{xx}}_{\text{piperazine}}N-\text{C}_6\text{H}_4-R_2$$

| Compound | R₁ | R₂ | Final Stereochemistry |
|---|---|---|---|
| 12a | [2-(2,4-dichlorophenyl)-1,3-dioxolan-4-yl, Trans] | [4-ethyl-3-oxo-1,2,4-triazol-1-yl, 2′] | Trans-2,4 |
| 13a | [2-(2,4-dichlorophenyl)-1,3-dioxolan-4-yl, Cis] | [4-ethyl-3-oxo-1,2,4-triazol-1-yl, 2′] | Cis-2,4 |
| 14a | [2S-(2,4-dichlorophenyl)-1,3-dioxolan-4S-yl] | [4-(2′S)-butyl-3-oxo-1,2,4-triazol-1-yl] | Trans-2S,4S,2′S |
| 15a | [2R-(2,4-dichlorophenyl)-1,3-dioxolan-4S-yl] | [4-(2′S)-butyl-3-oxo-1,2,4-triazol-1-yl] | Cis-2R,4S,2′S |
| 16a | [2R-(2,4-dichlorophenyl)-1,3-dioxolan-4R-yl] | [4-(2′S)-butyl-3-oxo-1,2,4-triazol-1-yl] | Trans-2R,4R,2′S |
| 17a | [2S-(2,4-dichlorophenyl)-1,3-dioxolan-4R-yl] | [4-(2′S)-butyl-3-oxo-1,2,4-triazol-1-yl] | Cis-2S,4R,2′S |

TABLE 2-continued

Second generation, stereochemically defined analogues of 2.

| Compound | R₁ | R₂ | Final Stereochemistry |
|---|---|---|---|
| 18a | 2,4-dichlorophenyl-2-methyl-1,3-dioxolane (2S,4S) | triazolone with sec-butyl (2'R) | Trans-2S,4S,2'R |
| 19a | 2,4-dichlorophenyl-2-methyl-1,3-dioxolane (2R,4S) | triazolone with sec-butyl (2'R) | Cis-2R,4S,2'R |
| 20a | 2,4-dichlorophenyl-2-methyl-1,3-dioxolane (2R,4R) | triazolone with sec-butyl (2'R) | Trans-2R,4R,2'R |
| 21a | 2,4-dichlorophenyl-2-methyl-1,3-dioxolane (2S,4R) | triazolone with sec-butyl (2'R) | Cis-2S,4R,2'R |
| 22a | 2,4-dichlorophenyl-2-methyl-1,3-dioxolane (2R,4R) | triazolone with propyl | Trans-2R,4R |
| 23a | 2,4-dichlorophenyl-2-methyl-1,3-dioxolane (2S,4R) | triazolone with propyl | Cis-2S,4R |
| 24a | 2,4-dichlorophenyl-2-methyl-1,3-dioxolane (2S,4S) | triazolone with propyl | Trans-2S,4S |
| 25a | 2,4-dichlorophenyl-2-methyl-1,3-dioxolane (2R,4S) | triazolone with propyl | Cis-2R,4S |

Analogues 1a-25a were synthesized following slightly modified literature procedures. All of these analogues contain the phenyl-piperazine-phenyl linker region of ITZ, which is initially constructed by a coupling step between commercially available N-(4-methoxyphenyl)-piperazine 26a and 1-chloro-4-nitrobenzene 27a to yield N-(4-hydroxylphenyl)-N'-(4-nitrophenyl)-piperazine 28a (Scheme 1a). The nitro moiety in 28a is reduced to the aniline 29a in the presence of hydrazine monohydrate and 10% palladium on charcoal. The aniline undergoes a series of well-characterized transformations to ultimately provide the key triazolone intermediate 32a. The methoxy substituent in starting material 26a serves as a protecting group throughout Scheme 1 and while other literature sources protect this phenol with a methoxymethyl (MOM) group, we found the synthetic scheme utilizing the MOM protection to be significantly less efficient in generating the corresponding key intermediate.

Scheme 1a. Synthesis of linker region intermediate.[a]

[a]Reagents and conditions: (a) K$_2$CO$_3$, reflux, 12 h, 82%; (b) Pd/C, NH$_2$NH$_2$•H$_2$O (10 eq), reflux, 3.5 h, 71%; (c) Pyr (17 eq), ClCOOPh (1.1 eq), 3 h, 90%; (d) NH$_2$NH$_2$•H$_2$O (5.5 eq), reflux, 3 h, quant; (e) formamidine acetate (4.5 eq), acetic acid, reflux, 3 h, 91%.

Triazolone 32a was alkylated with either commercially available alkyl bromides (37a-38a) or alkyl brosylates (35a-36a), which were prepared from the corresponding commercially available and stereochemically defined alcohols (33a-34a) (Scheme 2a). The methoxy group in the linker/triazolone/side chain intermediates (39a-42a) was removed with 48% hydrobromic acid in toluene to afford the phenols 43aa-46. It is important to note that alkylation of the triazolone results in an inversion of stereochemistry for the defined side chains; for example, (R)-brosylate 35a generates (S)-intermediates 39a and 43a.

Scheme 2a. Synthesis of linker/triazolone/side chain intermediates.[a]

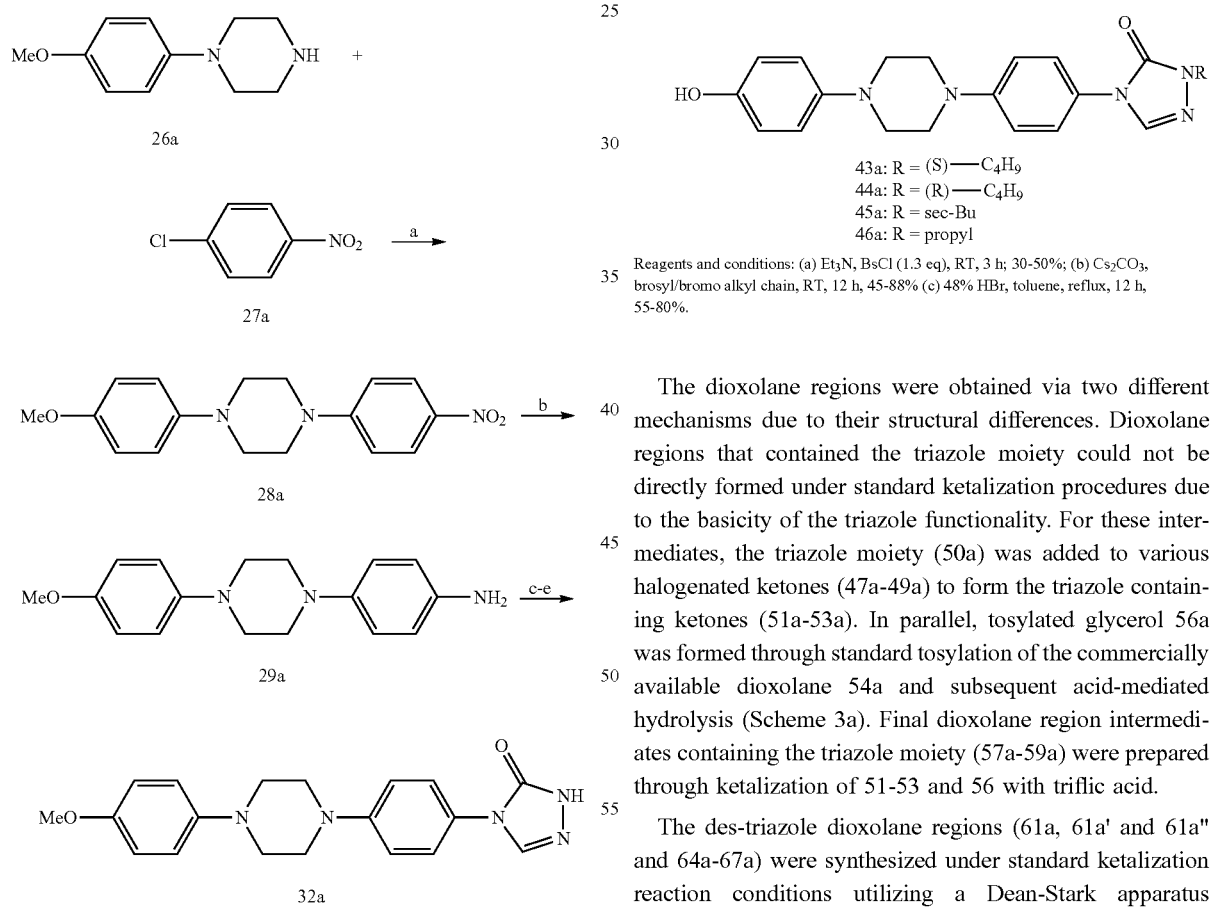

Reagents and conditions: (a) Et$_3$N, BsCl (1.3 eq), RT, 3 h; 30-50%; (b) Cs$_2$CO$_3$, brosyl/bromo alkyl chain, RT, 12 h, 45-88% (c) 48% HBr, toluene, reflux, 12 h, 55-80%.

The dioxolane regions were obtained via two different mechanisms due to their structural differences. Dioxolane regions that contained the triazole moiety could not be directly formed under standard ketalization procedures due to the basicity of the triazole functionality. For these intermediates, the triazole moiety (50a) was added to various halogenated ketones (47a-49a) to form the triazole containing ketones (51a-53a). In parallel, tosylated glycerol 56a was formed through standard tosylation of the commercially available dioxolane 54a and subsequent acid-mediated hydrolysis (Scheme 3a). Final dioxolane region intermediates containing the triazole moiety (57a-59a) were prepared through ketalization of 51-53 and 56 with triflic acid.

The des-triazole dioxolane regions (61a, 61a' and 61a" and 64a-67a) were synthesized under standard ketalization reaction conditions utilizing a Dean-Stark apparatus (Scheme 4a). Stereochemically defined tosylated glycerols 62a and 63a were prepared via the method described above for the racemic mixture and each of the protected glycerols was used to ketalize 2,4-dichloroacetophenone. For the stereochemically defined dioxolanes, the cis-isomer was predominantly formed (~3:1 cis:trans) and the isomers were easily separable via column chromatography.

Scheme 3a. Synthesis of triazole-containing dioxolane region intermediates.[a]

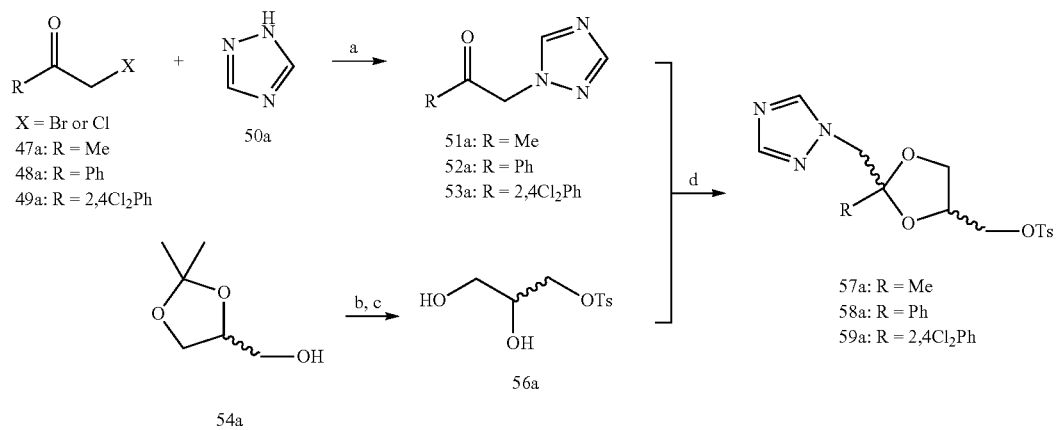

[a]Reagents and conditions: (a) NaHCO₃, toluene, reflux, 3 h, 25-65%; (b) Pyr, TsCl, 0° C.-RT, 12 h, 71%; (c) MeOH, 0.5N HCl, reflux, 5 h, 89%; (d) Triflic acid (3-4 eq), toluene, RT, 60 h 10-70%.

Scheme 4a. Synthesis des-triazole dioxolane region intermeditates.[a]

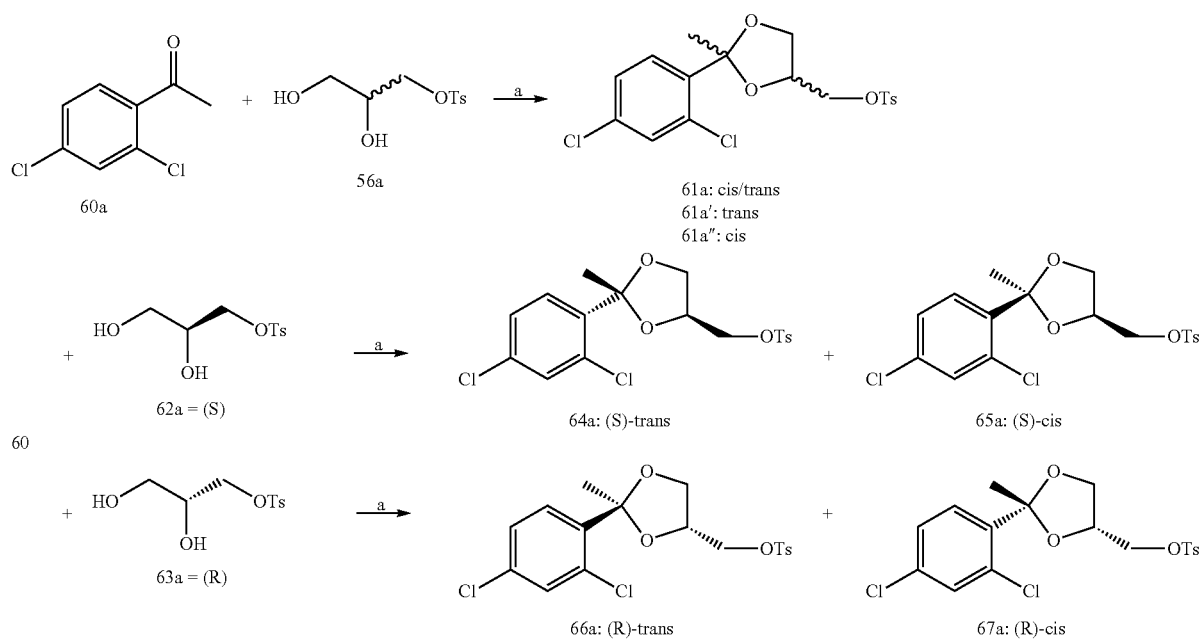

[a]Reagents and conditions: (a) p-TsOH (cat.), toluene, reflux (Dean Stark), 48 h, 70-90%.

Tosylated dioxolane regions were coupled with the linker/triazolone/side chain region phenols in anhydrous dimethyl sulfoxide with cesium carbonate to yield the final analogues 1a-8a and 12a-25a (Scheme 5aA). The truncated triazolone analogues (10a-11a) were synthesized in reverse order.[a] The unprotected linker region 68a was prepared in the same manner as 28a in Scheme 1a (Scheme 5aB). This linker region intermediate was then coupled with the tosylated dioxolane region 59a under similar conditions described above to afford truncated analogue 10a, which was reduced to the aniline with palladium on charcoal (10%) in the presence of hydrazine monohydrate to afford ITZ analogue 11a. Overall purification methods varied for each ITZ analogue, particularly amongst the first generation series that contained the triazole moiety. Purification methods for all compounds are listed in the experimental information.

Scheme 5a. Coupling reactions for final ITZ analogues.[a]

(A)

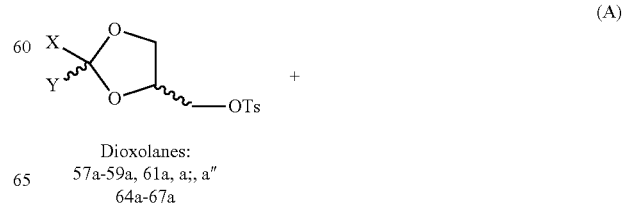

Dioxolanes:
57a-59a, 61a, a;, a''
64a-67a

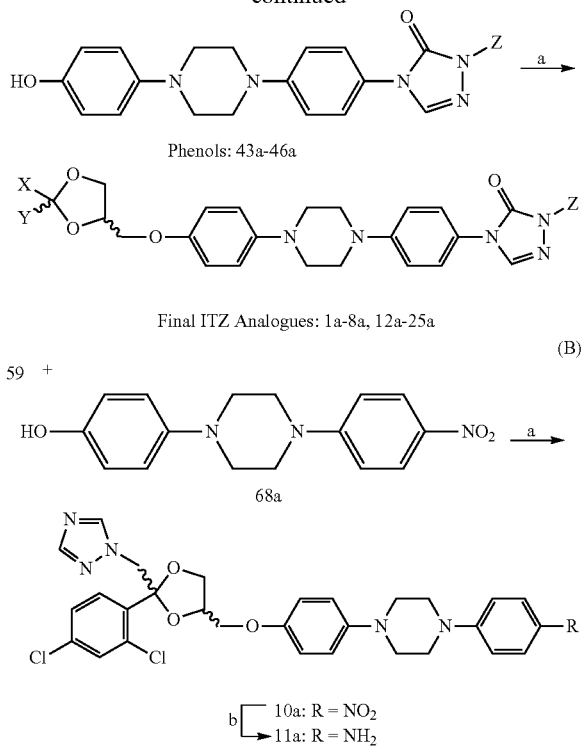

Phenols: 43a-46a

Final ITZ Analogues: 1a-8a, 12a-25a

68a

10a: R = NO$_2$
11a: R = NH$_2$

[a]Reagents and conditions: (a) Cs$_2$CO$_3$ (10 eq), DMSO, 90° C., 12 h, 45-88%; (b) Pd/C, NH$_2$NH$_2$·H$_2$O (10 eq), reflux, 3.5 h, 60-70%. The functional groups represented by X, Y, and Z above can also be found in Schemes 2-4.

Biological Evaluation: The initial evaluation of first generation ITZ analogues (1a-11a) as Hh pathway inhibitors was performed by monitoring endogenous Gli1 mRNA levels in C3H10T1/2 cells, an Hh-dependent mouse embryonic fibroblast (MEF) at a single concentration (1 μM). In this well-studied model system for evaluating small molecule inhibition of Hh signaling, addition of an exogenous Hh agonist (recombinant Hh ligand or small molecule) results in a characteristic increase in Gli1 mRNA expression. Concomitant incubation with a pathway inhibitor reduces Gli1 expression. Analogues that reduced Gli1 mRNA levels below 20% in this assay were subsequently evaluated for their ability to reduce Gli1 mRNA expression levels in a concentration-dependent fashion in these cells and the Hh-dependent murine BCC cell line ASZ. In addition, several compounds were evaluated for their anti-proliferative effects in primary Hh-dependent medulloblastoma cells isolated from conditional patched knockout (Math1-Cre-ER; Ptc$^{fl/fl}$, MERP) mice. Based on the primary nature of the MERP cells, only a small subset of $1^{st}$ and $2^{nd}$ generation ITZ analogues were chosen for evaluation in these cells. Finally, each of these analogues was evaluated for its ability to inhibit proliferation in human umbilical vein epithelial cells (HUVECs). In vivo angiogenesis is dependent on endothelial cell proliferation; therefore, the inhibition of HUVEC proliferation is commonly utilized as an early stage in vitro model of anti-angiogenic activity. In addition, the identification of ITZ as an anti-angiogenic compound was established via this assay. The results for these assays are given in Table 3a.

Evaluation of the first generation of ITZ analogues indicated several structural features that appear necessary for Hh pathway inhibition. While the absolute stereochemistry at the 2'-position of the sec-butyl side chain does not appear important, 6a and 7a are equipotent in the MEF and ASZ cell lines, removing the methyl moiety (8a) significantly reduces the overall activity of the scaffold. Interestingly, removing the side chain (9a) or the triazolone/side chain (10a-11a) did not affect the Hh inhibitory activity of the scaffold as each of these analogues also demonstrated potent inhibition of pathway signaling in each cell line with IC$_{50}$ levels comparable to ITZ. In regards to modifications to the dioxolane region, removal of the chlorine atoms on the phenyl ring had minimal effects (3a), while complete truncation of the phenyl ring (4a) resulted in a significant loss of anti-Hh activity. Removal of the triazole moiety (2a) had no effect on the ability of the scaffold to inhibit Hh signaling. Not surprisingly, removal of both the triazole and phenyl ring (5) or complete truncation to the phenol (45a), significantly reduced Hh inhibitory activity. Our synthesized ITZ (1a) demonstrated comparable activity to the ITZ purchased commercially in each of the cell lines evaluated. Finally, while each of the analogues evaluated was equipotent in its ability to down-regulate Gli1 mRNA expression in both the C3H10T1/2 and ASZ cells (Table 3), the ability of ITZ, 1a, and 11a to inhibit the proliferation of Hh-dependent murine MB cells was slightly reduced.

TABLE 3a

In vitro activity of first generation ITZ analogues.

| Compound | % Gli expression (1 μM)[a] | IC$_{50}$ (μM)[c] C3H10T1/2[a] | ASZ[d] | GI$_{50}$ (μM)[c] HUVEC | GI$_{50}$ (μM)[c] MERP MB[d] |
|---|---|---|---|---|---|
| ITZ | — | 0.074± | 0.14 ± 0.02 | 0.40 ± 0.03 | 0.44 ± 0.08 |
| 1a | 1.7 ± 0.3[b] | 0.063± | 0.17 ± 0.01 | 0.49 ± 0.09 | 0.6 ± 0.1 |
| 2a | 17.8 ± 0.5 | 0.14 ± 0.04 | 0.17 ± 0.04 | 23.8 ± 6.7 | ND |
| 3a | 13.1 ± 1.2 | 0.42 ± 0.2 | 0.45 ± 0.06 | 8.3 ± 0.7 | ND |
| 4a | 61.4 ± 3.5 | ND | ND | 18.4 ± 4.5 | ND |
| 5a | 71.4 ± 5.5 | ND | ND | >100 | ND |
| 6a | 6.9 ± 3.1 | 0.16 ± 0.04 | 0.14 ± 0.008 | 2.5 ± 0.3 | ND |
| 7a | 3.0 ± 0.9 | 0.14 ± 0.04 | 0.16 ± 0.07 | 1.7 ± 0.4 | ND |
| 8a | 58.5 ± 6.4 | ND | ND | 4.7 ± 0.3 | ND |
| 9a | 1.1 ± 0.2 | 0.043± | 0.12 ± 0.03 | 5.8 ± 0.8 | ND |
| 10a | 1.5 ± 0.05 | 0.13 ± 0.03 | 0.09 ± 0.01 | 8.4 ± 0.7 | ND |
| 11a | 6.1 ± 1.6 | 0.16 ± 0.06 | 0.12 ± 0.05 | 42.7 ± 4.4 | 0.9 ± 0.7 |
| 45a | 45.7 ± 3.0 | ND | ND | >100 | ND |

[a]All analogues evaluated following 24 hr incubation.
[b]Values represent % Gli1 expression relative to recombinant Hh ligand control (set as 100%).
[c]IC$_{50}$ and GI$_{50}$ values represent the Mean ± SEM of at least two separate experiments performed in triplicate.
[d]All analogues evaluated following 48 hr incubation.

Figure 6:
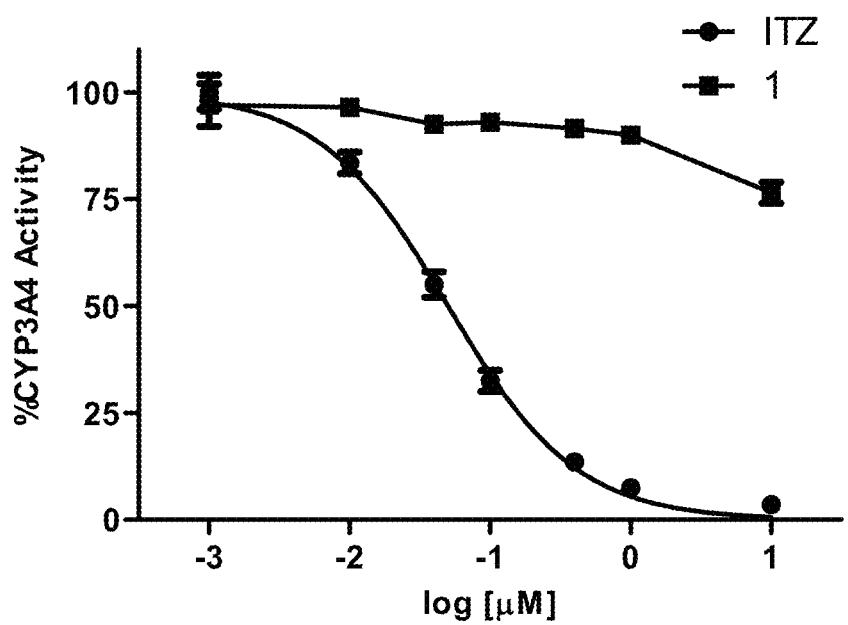
FIG. 6 shows the concentration-dependent inhibition of CYP3A4 by itraconazole and Analogue 1. These data are from a representative experiment performed in triplicate.
Figure 7:
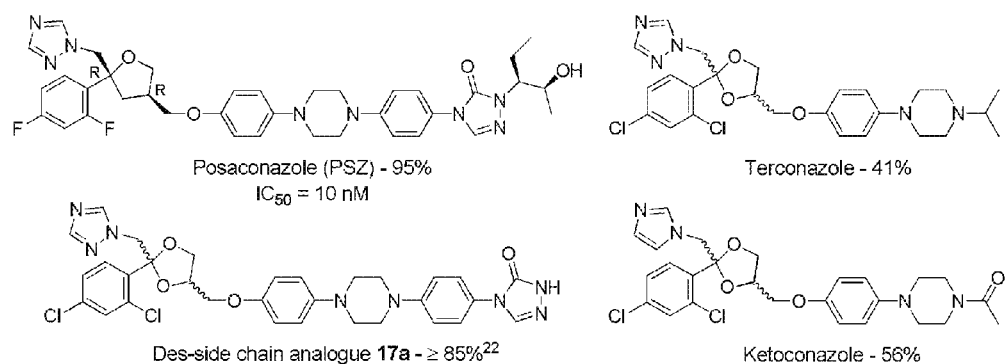
FIG. 7 shows Hh inhibitory activity of related azole antifungals. Values reported are percent inhibition of Hh signaling at 1 μM. Itraconazole inhibition of Hh signaling at 1 μM=96%. Data from analogue 17a represent percent inhibition of Hh signaling in an Hh-dependent MB at the $IC_{90}$ ($IC_{90}$ value not reported).

In addition to exploring Hh pathway inhibition, this first generation of ITZ analogues was evaluated for their ability to inhibit VEGF-induced proliferation in HUVECs, an initial step towards determining their ability to inhibit angiogenesis. The ITZ synthesized in the lab (1) demonstrated anti-proliferative activity comparable to the commercially purchased ITZ ($GI_{50}$ values=0.49 and 0.40 µM, respectively). The remaining ITZ analogues were significantly less active than ITZ in this assay. Several analogues were moderately active ($GI_{50}$ values, 1.7-8.4 µM), but none were comparable to ITZ. Finally, we compared ITZ and 2a for their ability to inhibit CYP3A4. Not surprisingly, removal of the triazole moiety completely abolished the ability of 2a to inhibit CYP3A4 ($IC_{50}$ values=50.4 nM and >10 µM, respectively, FIG. 6).

As noted above, the synthetic route primarily utilized to access ITZ results in a 1:1:1:1 ratio of four stereoisomers that share the cis configuration for the triazole and ether linker around the dioxolane ring. As a means to optimize our time and efforts related to the synthesis and evaluation of our first generation series of ITZ analogues, we did not fully characterize the ratio of stereoisomers present in each of the analogues. Instead they were evaluated as the stereoisomeric mixtures produced via the synthetic route(s) described. In order to more fully probe the absolute structural requirements of the scaffold for potent inhibition of Hh signaling and angiogenesis, we synthesized and evaluated a second generation series of stereochemically defined ITZ analogues based on the des-triazole ITZ analogue 2a. It is important to note that the nomenclature of the stereochemistry regarding the dioxolane region differs between ITZ and des-triazole ITZ analogues. The triazole moiety receives priority within the fully intact ITZ dioxolane region; therefore, the cis-orientation is in reference to the triazole and ether linkage (Chart 1). By contrast, removal of the triazole shifts priority to the phenyl ring and a cis-des-triazole analogue has the opposite absolute configuration between the phenyl ring and ether linker as ITZ. In addition, coupling of the dioxolane region intermediates to the linker/side chain phenol results in the opposite nomenclature assignment for the final ITZ analogue, for example, final analogues that have the 4R stereochemistry were prepared from the (S) tosylate 62a.

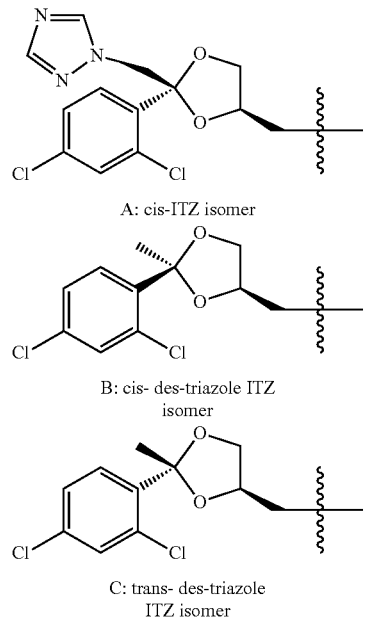

A: cis-ITZ isomer

B: cis- des-triazole ITZ isomer

C: trans- des-triazole ITZ isomer

Chart 1. Cis- and Trans-Nomenclature of Dioxolane Region: (A) Representative Cis-ITZ Isomer, (B) Cis- and (C) Trans-Des-Triazole Analogues.

Evaluation of our stereochemically defined analogues for their ability to inhibit Hh signaling in the C3H10T1/2 and ASZ cell lines provided both interesting and confounding results. Overall, the majority of the compounds evaluated (12a-25a, Table 4) were more active in the ASZ cells, with numerous analogues exhibiting 100- to 1000-fold improvement in activity in these cells when compared to the MEFs. Several analogues that were inactive in the C3H10T1/2 MEFs at concentrations up to 10 µM (15a, 24a-25a) induced potent down-regulation of Gli1 ($IC_{50}$ values=0.55, 0.2, and 0.54 µM, respectively). In addition, several other compounds with modest inhibitory effects in the MEF cell line (13a, 17a, and 21a) exhibited low nanomolar $IC_{50}$ values in the ASZ cells.

Even with the conflicting results between cell lines, several interesting SAR developments with respect to optimal configuration were identified for our second generation ITZ analogues. First, these results reiterated that the orientation of the methyl moiety in the sec-butyl side chain is less important, as long as it is present (Table 4a). Compounds that included a propyl moiety were significantly less active than analogues maintaining the same orientation around the dioxolane ring (i.e. 17a and 23a; 18a and 24a) and incorporating the sec-butyl moiety. ITZ analogues with the trans-orientation around the dioxolane generally demonstrated enhanced down-regulation of Gli1 mRNA expression in both cell lines when compared to the corresponding cis analogues. Finally, compounds containing the 4R configuration were generally more active than corresponding analogues with the 4S configuration and des-triazole analogues with the trans 2R,4R configuration (16a, 20a, and 22a) demonstrated the most comparable activity between the two cell lines.

TABLE 4a

In vitro activity of second generation ITZ analogues.

| Compound | $IC_{50}$ (µM)[a] C3H10T1/2[b] | $IC_{50}$ (µM)[a] ASZ[c] | $GI_{50}$ (µM)[a] HUVEC | $GI_{50}$ (µM)[a] MERP MB[c] |
|---|---|---|---|---|
| 12a | 0.091 ± 0.02 | 0.077 ± 0.01 | 3.32 ± 0.55 | 2.0 ± 1.3 |
| 13a | 0.85 ± 0.1 | 0.071 ± 0.02 | 3.69 ± 1.1 | 2.9 ± 1.9 |
| 14a | 1.1 ± 0.17 | 2.5 ± 0.7 | 7.7 ± 4.4 | ND |
| 15a | >10 | 0.55 ± 0.07 | 78.3 ± 17.3 | ND |
| 16a | 0.47 ± 0.001 | 0.38 ± 0.07 | 18.3 ± 11.8 | ND |
| 17a | 1.85 ± 0.09 | 0.15 ± 0.038 | 2.5 ± 0.7 | 0.39 ± 0.2 |
| 18a | 0.54 ± 0.24 | 0.13 ± 0.04 | 12.1 ± 4.7 | ND |
| 19a | 6.6 ± 0.3 | 2.8 ± 0.9 | 65.0 ± 11.5 | ND |
| 20a | 0.19 ± 0.04 | 0.022 ± 0.01 | 53.2 ± 25.2 | 0.6 ± 0.2 |
| 21a | 2.4 ± 0.6 | 0.024 ± 0.02 | 12.8 ± 2.9 | 1.0 ± 0.5 |
| 22a | 4.1 ± 1.5 | 1.3 ± 0.65 | 26.5 ± 3.5 | ND |
| 23a | >10 | 1.4 ± 0.5 | 49.9 ± 15.9 | ND |
| 24a | >10 | 0.2 ± 0.08 | 84.1 ± 33.5 | 22.4 ± 12 |
| 25a | >10 | 0.54 ± 0.06 | 24.9 ± 2.2 | ND |
| PSZ | 0.14 ± 0.02 | 0.54 ± 0.05 | 1.6 ± 0.02 | 1.5 ± 0.3 |

[a]$IC_{50}$ and $GI_{50}$ values represent the Mean ± SEM of at least two separate experiments performed in triplicate.
[b]All analogues evaluated following 24 hr incubation.
[c]All analogues evaluated following 48 hr incubation.

Based on the anti-Hh activity of the stereochemically defined compounds in the C3H10T1/2 and ASZ cells, we evaluated several of these ITZ analogues in the primary MB cell line. The specific analogues selected for the anti-proliferative studies were chosen either because they were potent in both cell lines (12a and 20a) or because they were significantly less active in the MEFs (13a, 17a, 21a, 24a). Measuring the anti-proliferative effects of these analogues in the Hh-dependent primary cell culture would not only provide additional in vitro data for the most active trans analogues, but might also serve to clarify the discrepancies in anti-Hh activity between the two immortalized cell lines. Not surprisingly, the mixtures of trans-(12a) and cis-(13a) stereoisomers were less active than the single stereochemically defined analogues. The most active analogue in this assay was 17a ($GI_{50}=0.39$ μM), which has the cis 2R,4R configuration around the dioxolane moiety. Finally, the reduced anti-proliferative activity demonstrated for analogue 24a further highlights the importance of the methyl group on the side chain for Hh inhibition. Based on the anti-proliferative results in the MB cells, we chose to evaluate ITZ and three analogues (17a, 20a, and 21a) for their ability to down-regulate endogenous Gli1 mRNA expression in the MERP MB cell line. Along with ITZ, each of these compounds exhibited potent down-regulation of mRNA expression in this assay further demonstrating their ability to inhibit Hh signaling (Table 5a). It is important to note that the anti-Hh activity of the ITZ analogues in the MERP MB cells more closely correlated with the data obtained in the ASZ cells, suggesting that the immortalized BCC cell line may be a more appropriate early stage in vitro cellular model of Hh signaling for evaluating analogues based on the ITZ scaffold.

TABLE 5a

Down-regulation of Gli1 mRNA in MERP MB cells.

| Compound[a] | $IC_{50}$ (μM)[b] |
|---|---|
| ITZ | 0.39 ± 0.06 |
| 17a | 0.26 ± 0.12 |
| 20a | 0.19 ± 0.07 |
| 21a | 0.29 ± 0.08 |

[a]All analogues evaluated following 48 hr incubation.
[b]$IC_{50}$ values represent the Mean ± SEM of two separate experiments.

Following the initial identification of ITZ as an Hh pathway inhibitor, several additional azole anti-fungals were evaluated for their anti-Hh properties. Interestingly, the closely related, stereochemically defined triazole anti-fungal posaconazole was not explored in these early studies. Based on our findings that ITZ analogue 20a was the most consistent in its ability to inhibit pathway activity across multiple Hh-dependent cell lines, we also evaluated PSZ, which shares the same orientation around its tetrahydrofuran (THF) ring, in each of these assays. PSZ demonstrated potent down-regulation of Gli1 expression in the MEF and ASZ cell lines; however, it was significantly less active in the MERP cells. Taken together, these data strongly suggesting that the dioxolane and hydrophobic side chain of ITZ are more active than the corresponding THF and hydroxylated side chains of PSZ.

The second generation of ITZ analogues was also evaluated in the HUVECs for their anti-angiogenic activity. In a fashion similar to our initial series, each analogue evaluated in this assay was significantly less active than the commercially purchased ITZ. Interestingly, the trans-(12a) and cis-(13a) dioxolane mixtures were both more potent than the complete mixture (2a). Our results did not yield a clear SAR pattern that distinguished one stereo-defined dioxolane region to be more potent against HUVEC anti-proliferation he stereoisomer that had the lowest $IC_{50}$, 17a, contains the (R)-cis-dioxolane region and the (S)-sec-butyl group ($IC_{50}=2.5\pm0.7$ μM). When only the stereochemistry of the sec-butyl moiety is inverted (21a), activity is attenuated ($IC_{50}=12.8\pm2.9$ μM). Overall, the (S)-sec-butyl analogues have lower $IC_{50}$ values than the corresponding (R)-sec-butyl analogues. The same trend held true for the (R)-trans-dioxolane analogues (16a and 20a); this was the most potent orientation determined from the Hh pathway evaluation. These results differ from the Hh pathway inhibitory activity of the scaffold in that the stereochemistry of the side chain region did not play a significant role in achieving potent inhibition. Taken together, there is not one dioxolane region that can be readily determined as the most potent across the second generation of ITZ analogues for inhibiting proliferation of HUVEC cells.

Based on the lack of clear SAR in the HUVEC cells, we sought to further explore the anti-angiogenic properties of ITZ and our analogues by evaluating their ability to inhibit tube formation in HUVECs grown on Matrigel. Under normal conditions, HUVECs plated and grown on Matrigel migrate towards each other, align, and form tubes that resemble in vivo capillary beds. This assay is generally considered a more robust model of angiogenesis as it requires several aspects of proper vessel formation, including adhesion, migration, and tube formation. As tube formation assays are inherently lower-throughput, we chose to evaluate only a few select compounds, including, ITZ, 2a, 18a, 21a, and the well-characterized angiogenesis inhibitor suramin (positive control). These analogues were chosen for evaluation based on both their activity in the anti-proliferation assays and their overall structure in an attempt to provide the most relevant preliminary information with respect to the ability of this scaffold to inhibit angiogenesis.

Inhibition of tube formation (as measured by overall tube length and total tube junctions) by ITZ and 2a were comparable to that of the positive control suramin at 10 μM; however, neither of the stereochemically defined analogues (18a and 21a) were active at this concentration (FIGS. 12 and 13). ITZ also demonstrated significant inhibition of tube formation at 1 μM. A decrease in activity was observed at 1 μM for analogue 2a, highlighting the importance of the triazole moiety for optimal anti-angiogenic activity of the scaffold. Interestingly, there was minimal correlation between the ability of a compound to inhibit anti-proliferation and tube formation in the HUVEC cells. ITZ was most active in both assay systems; however, analogues 18a and 21a were two-fold more active in the anti-proliferation assay than 2a, yet they were essentially inactive in the tube formation assay. Taken together, these data suggest that the triazole of ITZ is important for the anti-angiogenic activity of the scaffold.

Discussion and Conclusions: Significant modifications to multiple regions of the ITZ scaffold resulted in compounds that retained the ability to inhibit Hh signaling in Hh-dependent MEFs, murine BCC cells, and murine MB cells. By contrast, every analogue evaluated was significantly less active than ITZ in the anti-angiogenic assays performed in HUVECs. Preliminary data provides strong evidence that ITZ inhibits the Hh pathway through Smoothened (Smo), a key regulator of this signaling cascade. As neither Smo nor Hh signaling are known to play a role in angiogenesis, it is reasonable to hypothesize that the anti-angiogenic properties of ITZ are mediated through a distinct, as yet unidentified, cellular target not associated with this developmental pathway; however, further studies are needed to definitively characterize Smo/ITZ binding interactions and identify the cellular protein(s) responsible for its ability to inhibit cellular angiogenesis.

A key goal for our initial ITZ analogue series was to determine whether the triazole moiety was essential for the anti-cancer properties of the scaffold. Removal of the triazole from the dioxolane region (2a) had no effect on the ability to inhibit Hh signaling in either cell line; however, it did significantly affect the anti-angiogenic properties of the scaffold. This also provides further evidence that the anti-cancer activities of ITZ are mediated through distinct cellular mechanisms and highlights the importance of the triazole for the ability of ITZ to inhibit angiogenesis. Not surprisingly, removal of the triazole completely abolished inhibition of CYP3A4, the main detrimental side effect of ITZ, providing an improved lead scaffold for further development as an inhibitor of Hh signaling.

After establishing that the triazole functionality is not required for Hh inhibition, we prepared and evaluated two additional series of analogues to (1) determine whether truncation at other locations affected the anti-Hh properties of the scaffold and (2) identify the optimal stereochemical orientation of our new lead 2. The truncated analogues were not only designed to identify the pharmacophore for ITZ inhibition of Hh signaling, but also to reduce the overall size of ITZ (molecular weight=705.6 g/mol) to improve both its drug-like properties and the overall synthetic efficiency of preparing these compounds. Overall, the dioxolane region was not amenable to further truncation; however, removing the triazolone/side chain region did not affect the ability of the scaffold to inhibit Hh signaling in any of the Hh-dependent cell lines (analogue 11a). For the stereochemically defined analogues of 2a, the trans orientation was preferred for the dioxolane region and more specifically the trans 2R,4R analogues were consistently more active than other analogues with their respective side chain orientation in the immortalized cell lines. In the primary murine MB cells, a cis analogue (17a) with the 4R orientation also demonstrated potent anti-proliferative effects, suggesting that the (R)-configuration at the 4-position of the dioxolane ring might be more important for Hh inhibition than the overall cis- or trans-orientation. This is further highlighted by the significant reduction in anti-proliferative activity for analogue 24a (trans-2S,4S).

While the active first generation ITZ analogues demonstrated comparable Hh inhibition in both the C3H10T1/2 and ASZ cell lines, the second generation, stereochemically defined analogues were generally more active in the ASZs. Several possibilities exist to explain the differential activity identified for the second generation analogues. First, it is possible that decreased permeability for the stereochemically defined compounds in the C3H10T1/2 cells prevents their intracellular accumulation at concentrations required for potent activity. Second, the cellular target that mediates the anti-Hh activity of the ITZ scaffold (presumably Smo) may be more responsive to the stereochemically defined analogues in the ASZ cells. In addition, Hh signaling in the C3H10T1/2 cells must be activated through the addition of an exogenous agonist (for these assays, recombinant sonic Hh ligand), while Hh signaling and Gli1 overexpression are constitutively active in the ASZ cells due to a heterozygous mutation in the PTCH1 allele. Up-regulation of pathway signaling with the Hh ligand in the MEFs may result in a level of Gli1 overexpression that cannot be fully overcome by the ITZ analogue(s). Finally, complete inhibition of Hh signaling for the ITZ scaffold may rely on the presence of multiple stereoisomers to fully inhibit its target, which could explain why the isomeric mixtures in the first generation demonstrated comparable activity across both cell lines. These discrepancies are currently being addressed in ongoing studies to more fully understand the mechanisms that govern ITZ-mediated inhibition of both cell lines.

A consideration for the further development of these and other ITZ analogues as potential Smo antagonists is that multiple forms of mutant Smo have been identified in both BCC and MB patients receiving a small molecule Smo antagonists. These mutations in Smo oftentimes render patients insensitive to further treatment with the Smo antagonists that have been approved by the FDA. A key rationale for developing ITZ analogues as Hh pathway inhibitors is that ITZ has previously demonstrated the ability to inhibit several resistant forms of Smo in vitro and in vivo, however, any further development of these analogues as Hh inhibitors must demonstrate that they also prevent pathway signaling in the presence of mutant Smo. Attempts to circumvent mutant Smo by Developing small molecule Hh pathway inhibitors that function downstream of Smo at the level of the Gli transcription factors has emerged as a potential strategy to circumvent mutant Smo; however, all of the Gli inhibitors reported to date demonstrate only modest inhibition of Hh signaling, suggesting more studies are necessary to determine whether directly targeting Gli(s) is a valid therapeutic strategy.

In conclusion, we have synthesized and evaluated two series of ITZ analogues for their ability to inhibit both Hh signaling and angiogenesis.

Certain compounds have duplicate numbers as indicated below.

| Name 1 | Name 2 |
| --- | --- |
| ITZ itraconazole | 1, ITZ (Table 1a) |
| Analogue 1 and 95 | 2a (Table 1a) |
| 93 | 3a (Table 1a) |
| 94 | 4a (Table 1a) |
| 96 | 5a (Table 1a) |
| 27-30 | 14a-17a (Table 2a) |
| 23-26 | 18a-21a (Table 2a) |
| 31-34 | 22a-25a (Table 2a) |

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A compound having the structure of Formula (I)

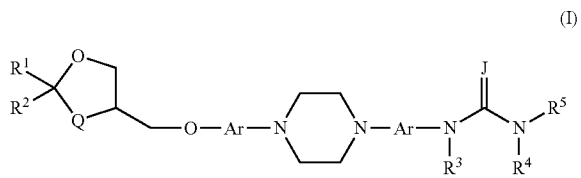

(I)

wherein

Q is O or $CH_2$;

each Ar is independently unsubstituted or substituted aryl or heteroaryl;

J is O or S;

$R^1$ is $C_{1-6}$ alkyl optionally substituted with an amino, a $C_{1-6}$ alkylamino, a $C_{1-6}$ dialkylamino, an N-acylamino, —COOH, an aryl, a heterocycloalkyl, pyrrolidine or pyrrole, group;

$R^2$ is $C_{1-6}$ alkyl or unsubstituted or substituted aryl;

$R^3$ is H or unsubstituted or substituted $C_{1-6}$ alkyl;

$R^4$ is H or unsubstituted or substituted $C_{1-6}$ alkyl; or $R^3$ and $R^4$ join to form an unsubstituted or substituted 5- or 6-membered ring with the —N-(=J)-N— moiety where $R^3$ and $R^4$ form a unsubstituted or substituted $C_{2-3}$ carbohydryl group or a unsubstituted or substituted $C_{1-2}$ carbohydryl group linked via a nitrogen to a nitrogen of the —N-(=J)-N— moiety;

$R^5$ is H, substituted or unsubstituted $C_{1-6}$ alkyl, $C_{1-6}$ alkoxy, $C_{2-6}$ alkanoyl, $C_{1-6}$ alkoxcarbonyl, $C_{1-6}$ haloalkyl, wherein the substituted $C_{1-6}$alkyl is substituted with 1, 2, or 3 substituents, each substituent is independently $C_{1-6}$ alkyl, —OH, —COOH, cyano, nitro, $C_{1-6}$ monoalkylamine, $C_{1-6}$ dialkylamine, $C_{1-6}$ haloalkyl, $C_{1-6}$ haloalkoxy;

a pharmaceutically acceptable salt, a stereoisomeric form thereof, or a combination thereof.

2. The compound of claim 1, wherein Q is O; each Ar is phenyl, pyridine, pyrazine, or pyridazine; and J is O.

3. The compound of claim 1, wherein each Ar is phenyl.

4. The compound of claim 1, wherein $R^1$ is methyl optionally substituted with, 1-pyrrole, phenyl, m-aminophenyl, p-aminophenyl, acetylamine, 1-pyrrolidine, amino, or dimethylamino; and $R^2$ is unsubstituted or substituted phenyl.

5. The compound of claim 1, wherein $R^1$ is methyl and $R^2$ is 2,4-dichlorophenyl or 2,4-difluorophenyl.

6. The compound of claim 1, wherein $R^3$ and $R^4$ join to form an unsubstituted or substituted 5- or 6-membered ring with the —N-(=J)-N— moiety where $R^3$ and $R^4$ form a unsubstituted or substituted $C_{2-3}$ carbohydryl group or a unsubstituted or substituted $C_{1-2}$ carbohydryl group linked via a nitrogen to a nitrogen of the —N-(=J)-N— moiety.

7. The compound of claim 1, wherein $R^5$ is propyl; 2'-sec-butyl, the R isomer, the S isomer, a racemate or any enantiomerically enriched form; 2-hydroxypentan-3-yl, the 2R,3R-isomer, the 2S,3S, isomer, the 2R,3S, isomer, the 2S,3R isomer, or any diastereomerically enriched form; 2-hydroxyprop-2-yl; or 2-hydroxyprop-1-yl, the R isomer, the S isomer, a racemate, or any enantiomerically enriched form.

8. The compound of claim 1, having the Formula (Ia)

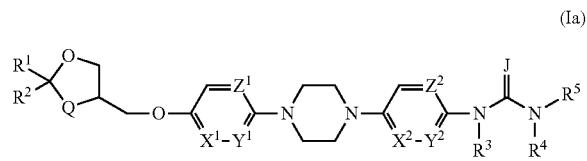

(Ia)

wherein each one of $X^1$, $X^2$, $Y^1$, $Y^2$, $Z^1$, and $Z^2$ independently is CH, $CCH_3$, or N.

9. The compound of claim 8, wherein in Formula (Ia)

$X^1$ is N and $Y^1$, $Z^1$, $X^2$, $Y^2$, and $Z^2$ are CH;

$Y^1$ is N and $X^1$, $Z^1$, $X^2$, $Y^2$, and $Z^2$ are CH;

$X^1$ and $Y^1$ are N and $Z^1$, $X^2$, $Y^2$, and $Z^2$ are CH;

$X^1$ and $Z^1$ are N and $Y^1$, $X^2$, $Y^2$, and $Z^2$ are CH;

$X^2$ is N and $X^1$, $Y^1$, $Z^1$, $Y^2$, and $Z^2$ are CH;

$Y^2$ is N and $X^1$, $Y^1$, $Z^1$, $X^2$, and $Z^2$ are CH;

$X^2$ and $Y^2$ are N and $X^1$, $Y^1$, $Z^1$, and $Z^2$ are CH; or $X^2$ and $Z^2$ are N and $X^1$, $Y^1$, $Z^1$, and $Y^2$ are CH.

10. The compound of claim 1, having Formula (Ib)

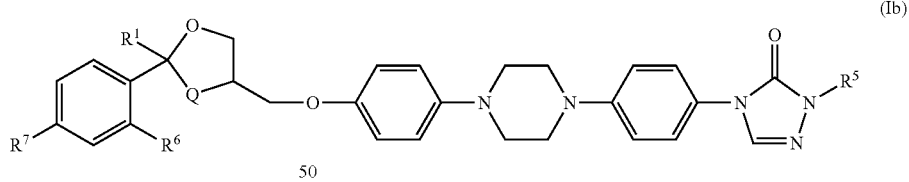

(Ib)

wherein $R^6$ and $R^7$ are each independently H, halo, $C_{1-6}$ alkyl, $C_{1-6}$ alkoxy, $C_{2-6}$ alkanoyl, $C_{1-6}$ alkoxcarbonyl, —$NH_2$, —OH, —COOH, cyano, nitro, $C_{1-6}$ monoalkylamine, $C_{1-6}$ dialkylamine, $C_{1-6}$ haloalkyl, or $C_{1-6}$ haloalkoxy.

11. The compound of claim 10, wherein $R^6$ and $R^7$ are each independently Cl or F.

12. The compound of claim 1, which is

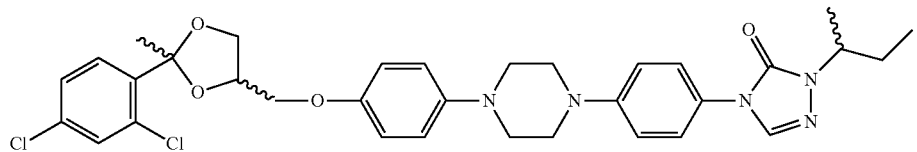

13. A pharmaceutical composition comprising the compound of claim 1 and a pharmaceutically acceptable excipient.

\* \* \* \* \*